US008793522B2

(12) United States Patent
Rahman et al.

(10) Patent No.: US 8,793,522 B2
(45) Date of Patent: Jul. 29, 2014

(54) POWER MANAGEMENT IN A DATA-CAPABLE STRAPBAND

(75) Inventors: Hosain Sadequr Rahman, San Francisco, CA (US); Richard Lee Drysdale, Santa Cruz, CA (US); Michael Edward Smith Luna, San Jose, CA (US); Scott Fullam, Palo Alto, CA (US); Travis Austin Bogard, San Francisco, CA (US); Jeremiah Robison, San Francisco, CA (US); Max Everett Utter, II, San Francisco, CA (US); Thomas Alan Donaldson, London (GB)

(73) Assignee: AliphCom, San Francisco, CA (US)

( * ) Notice: Subject to any disclaimer, the term of this patent is extended or adjusted under 35 U.S.C. 154(b) by 331 days.

(21) Appl. No.: 13/180,320

(22) Filed: Jul. 11, 2011

(65) Prior Publication Data
US 2012/0317430 A1 Dec. 13, 2012

Related U.S. Application Data

(60) Provisional application No. 61/495,995, filed on Jun. 11, 2011, provisional application No. 61/495,994, filed on Jun. 11, 2011, provisional application No. 61/495,997, filed on Jun. 11, 2011, provisional application No. 61/495,996, filed on Jun. 11, 2011.

(51) Int. Cl.
*G06F 1/00* (2006.01)
*G06F 1/32* (2006.01)

(52) U.S. Cl.
USPC ............................ 713/323; 713/320; 713/324

(58) Field of Classification Search
USPC ........................................................ 713/323
See application file for complete search history.

(56) References Cited

U.S. PATENT DOCUMENTS

| 5,795,301 | A | * | 8/1998 | Yasukawa et al. ............ 600/500 |
| 5,974,262 | A | | 10/1999 | Fuller et al. |
| D439,981 | S | | 4/2001 | Kasabach et al. |
| D451,604 | S | | 12/2001 | Kasabach et al. |
| 6,356,940 | B1 | | 3/2002 | Short |
| D460,971 | S | | 7/2002 | Sica et al. |

(Continued)

FOREIGN PATENT DOCUMENTS

| WO | PCT/US01/40958 | 12/2001 |
| WO | PCT/US01/20014 | 1/2002 |

(Continued)

OTHER PUBLICATIONS

U.S. Appl. No. 61/516,479, filed Apr. 4, 2011, Fish et al.

(Continued)

*Primary Examiner* — Suresh Suryawanshi
(74) *Attorney, Agent, or Firm* — Kokka & Backus, PC

(57) ABSTRACT

Embodiments of the invention relates generally to electrical and electronic hardware, computer software, wired and wireless network communications, and computing devices, and more specifically to structures and techniques for managing power generation, power consumption, and other power-related functions in a data-capable strapband. Embodiments relate to a band including sensors, a controller coupled to the sensors, an energy storage device, a connector configured to receive power and control signals, and a power manager. The power manager includes at least a transitory power manager configured to manage power consumption of the band during a first power mode and a second mode. The band can be configured as a wearable communications device and sensor platform.

20 Claims, 42 Drawing Sheets

(56) References Cited

U.S. PATENT DOCUMENTS

| | | | |
|---|---|---|---|
| 6,486,801 | B1 | 11/2002 | Jones |
| 6,527,711 | B1 | 3/2003 | Stivoric et al. |
| 6,595,929 | B2 | 7/2003 | Stivoric et al. |
| 6,605,038 | B1 | 8/2003 | Teller et al. |
| 6,714,859 | B2 | 3/2004 | Jones |
| 6,904,359 | B2 | 6/2005 | Jones |
| 6,952,645 | B1 | 10/2005 | Jones |
| 7,020,508 | B2 | 3/2006 | Stivoric et al. |
| 7,030,781 | B2 | 4/2006 | Jones |
| 7,153,262 | B2 | 12/2006 | Stivoric et al. |
| 7,260,732 | B1 * | 8/2007 | Bittner, Jr. .......... 713/324 |
| 7,261,690 | B2 | 8/2007 | Teller et al. |
| 7,285,090 | B2 | 10/2007 | Stivoric et al. |
| 7,343,260 | B1 | 3/2008 | Kahn et al. |
| 7,400,970 | B2 | 7/2008 | Jones |
| 7,457,719 | B1 | 11/2008 | Kahn et al. |
| 7,502,643 | B2 | 3/2009 | Farringdon et al. |
| 7,623,406 | B2 * | 11/2009 | Park et al. .......... 365/230.06 |
| 7,647,195 | B1 | 1/2010 | Kahn et al. |
| 7,647,196 | B2 | 1/2010 | Kahn et al. |
| 7,653,508 | B1 | 1/2010 | Kahn et al. |
| 7,662,065 | B1 | 2/2010 | Kahn et al. |
| 7,689,437 | B1 | 3/2010 | Teller et al. |
| 7,690,556 | B1 | 4/2010 | Kahn et al. |
| 7,705,723 | B2 | 4/2010 | Kahn et al. |
| 7,747,735 | B1 | 6/2010 | Kahn et al. |
| 7,753,861 | B1 | 7/2010 | Kahn et al. |
| 7,788,059 | B1 | 8/2010 | Kahn et al. |
| 7,800,044 | B1 | 9/2010 | Kahn et al. |
| 7,839,279 | B2 | 11/2010 | Kahn et al. |
| 7,849,184 | B1 | 12/2010 | Kahn et al. |
| D631,552 | S | 1/2011 | Kasabach et al. |
| D632,396 | S | 2/2011 | Kasabach et al. |
| 7,881,902 | B1 | 2/2011 | Kahn et al. |
| 7,907,901 | B1 | 3/2011 | Kahn et al. |
| 7,917,768 | B2 | 3/2011 | Kahn et al. |
| 7,959,567 | B2 | 6/2011 | Stivoric et al. |
| 7,970,586 | B1 | 6/2011 | Kahn et al. |
| 7,982,770 | B1 | 7/2011 | Kahn et al. |
| 7,987,070 | B2 | 7/2011 | Kahn et al. |
| 7,993,276 | B2 | 8/2011 | Nazarian et al. |
| D645,968 | S | 9/2011 | Kasabach et al. |
| 8,040,382 | B2 | 10/2011 | Kahn et al. |
| 8,047,966 | B2 | 11/2011 | Dorogusker et al. |
| 8,049,614 | B2 | 11/2011 | Kahn et al. |
| 8,064,759 | B1 | 11/2011 | Kahn et al. |
| 8,073,707 | B2 | 12/2011 | Teller et al. |
| 8,083,643 | B2 | 12/2011 | Ng et al. |
| 8,423,643 | B2 * | 4/2013 | Bouknight et al. .......... 709/226 |
| 8,451,710 | B2 * | 5/2013 | Lee et al. .......... 370/212 |
| 8,527,016 | B2 * | 9/2013 | Lee et al. .......... 455/574 |
| 2007/0258507 | A1 * | 11/2007 | Lee et al. .......... 375/138 |
| 2007/0259629 | A1 * | 11/2007 | Lee et al. .......... 455/127.1 |
| 2007/0259662 | A1 * | 11/2007 | Lee et al. .......... 455/433 |

FOREIGN PATENT DOCUMENTS

| | | |
|---|---|---|
| WO | PCT/US02/09972 | 10/2002 |
| WO | PCT/US02/24552 | 2/2003 |
| WO | PCT/US03/026261 | 3/2004 |
| WO | PCT/US2004/026187 | 2/2005 |
| WO | PCT/US2005/009476 | 10/2005 |
| WO | PCT/US2008/054312 | 8/2008 |
| WO | PCT/US2009/006234 | 6/2010 |

OTHER PUBLICATIONS

U.S. Appl. No. 61/404,379, filed Oct. 4, 2010, Fish et al.
U.S. Appl. No. 61/516,480, filed Apr. 4, 2011, Fish et al.
U.S. Appl. No. 61/404,381, filed Oct. 4, 2010, Ram David Adva Fish.
U.S. Appl. No. 12/684,881, filed Jul. 14, 2011, Kahn et al.
U.S. Appl. No. 12/472,361, filed Dec. 2, 2010, Kahn et al.
U.S. Appl. No. 12/247,950, filed Apr. 8, 2010, Kahn et al.
U.S. Appl. No. 12/202,206, filed Mar. 4, 2010, Kahn et al.
U.S. Appl. No. 12/469,633, filed Nov. 26, 2009, Kahn et al.
U.S. Appl. No. 12/113,110, filed Nov. 5, 2009, Kahn et al.
U.S. Appl. No. 11/871,151, filed Apr. 16, 2009, Kahn et al.
U.S. Appl. No. 12/490,304, filed Dec. 24, 2009, Kahn et al.
U.S. Appl. No. 11/582,896, filed May 3, 2007, Stivoric et al.
U.S. Appl. No. 10/638,588, filed Feb. 19, 2004, Teller et al.
U.S. Appl. No. 10/682,293, filed Jul. 8, 2004, Teller et al.
U.S. Appl. No. 10/940,214, filed May 26, 2005, Pacione et al.
U.S. Appl. No. 11/088,002, filed Nov. 3, 2005, Stivoric et al.
U.S. Appl. No. 11/239,748, filed Nov. 23, 2006, Stivoric et al.
U.S. Appl. No. 11/322,010, filed Jun. 8, 2006, Teller et al.
U.S. Appl. No. 11/434,949, filed Oct. 5, 2006, Teller et al.
U.S. Appl. No. 11/481,147, filed Feb. 15, 2007, Stivoric et al.
U.S. Appl. No. 11/724,373, filed Jul. 26, 2007, Teller et al.
U.S. Appl. No. 11/925,906, filed Jul. 31, 2008, Teller et al.
U.S. Appl. No. 11/925,965, filed Jul. 17, 2008, Stivoric et al.
U.S. Appl. No. 11/928,039, filed Jul. 10, 2008, Stivoric et al.
U.S. Appl. No. 11/928,302, filed Jul. 31, 2008, Farringdon et al.
U.S. Appl. No. 11/930,036, filed Jul. 10, 2008, Teller et al.
U.S. Appl. No. 11/930,053, filed Jul. 10, 2008, Teller et al.
U.S. Appl. No. 11/930,081, filed Jul. 3, 2008, Teller et al.
U.S. Appl. No. 11/930,091, filed Jul. 3, 2008, Teller et al.
U.S. Appl. No. 11/930,092, filed Jul. 17, 2008, Teller et al.
U.S. Appl. No. 11/930,094, filed Jul. 17, 2008, Teller et al.
U.S. Appl. No. 12/033,728, filed Jan. 1, 2009, Stivoric et al.
U.S. Appl. No. 12/033,722, filed Jan. 1, 2009, Stivoric et al.
U.S. Appl. No. 12/033,731, filed Dec. 25, 2008, Stivoric et al.
U.S. Appl. No. 12/033,737, filed Dec. 25, 2008, Stivoric et al.
U.S. Appl. No. 12/033,741, filed Dec. 25, 2008, Stivoric et al.
U.S. Appl. No. 12/033,746, filed Dec. 25, 2008, Stivoric et al.
U.S. Appl. No. 12/033,751, filed Dec. 25, 2008, Stivoric et al.
U.S. Appl. No. 12/033,753, filed Dec. 25, 2008, Stivoric et al.
U.S. Appl. No. 12/033,760, filed Dec. 25, 2008, Stivoric et al.
U.S. Appl. No. 12/033,766, filed Dec. 25, 2008, Stivoric et al.
U.S. Appl. No. 12/217,299, filed Jul. 9, 2009, Stivoric et al.
U.S. Appl. No. 12/840,109, filed Nov. 11, 2010, Farringdon et al.
U.S. Appl. No. 60/729,663, filed Oct. 24, 2005, Donald G. Stein.
U.S. Appl. No. 60/727,357, filed Oct. 17, 2005, Pacione et al.
U.S. Appl. No. 60/555,280, filed Mar. 22, 2004, Pacione et al.
U.S. Appl. No. 60/502,746, filed Sep. 12, 2003, Bucher et al.
U.S. Appl. No. 60/417,163, filed Oct. 9, 2002, Andre et al.
U.S. Appl. No. 60/729,683, filed Oct. 24, 2005, Stivoric et al.
U.S. Appl. No. 60/958,516, filed Jul. 6, 2007, Andre et al.
U.S. Appl. No. 60/510,013, filed Oct. 9, 2003, Farringdon et al.
U.S. Appl. No. 60/502,764, filed Sep. 12, 2003, Stivoric et al.
U.S. Appl. No. 60/901,952, filed Feb. 16, 2007, Stivoric et al.
U.S. Appl. No. 11/925,902, filed May 7, 2009, Teller et al.
U.S. Appl. No. 11/925,903, filed Jul. 31, 2008, Teller et al.
U.S. Appl. No. 11/925,908, filed Jul. 17, 2008, Teller et al.
U.S. Appl. No. 11/876,601, filed Oct. 22, 2007, Stivoric et al.
U.S. Appl. No. 11/930,405, filed Jul. 24, 2008, Teller et al.
U.S. Appl. No. 11/928,059, filed Sep. 4, 2008, Stivoric et al.
U.S. Appl. No. 11/928,027, filed Jul. 3, 2008, Stivoric et al.
U.S. Appl. No. 11/928,051, filed Jul. 10, 2008, Stivoric et al.
U.S. Appl. No. 11/930,100, filed Jul. 17, 2008, Teller et al.
U.S. Appl. No. 11/930,048, filed Jul. 10, 2008, Teller et al.
U.S. Appl. No. 11/930,101, filed Jul. 10, 2008, Teller et al.
U.S. Appl. No. 11/927,365, filed Nov. 20, 2008, Stivoric et al.
U.S. Appl. No. 11/927,276, filed Nov. 20, 2008, Stivoric et al.
U.S. Appl. No. 13/253,000, filed Oct. 4, 2011, Ram David Adva Fish.
U.S. Appl. No. 13/182,352, filed Jan. 5, 2012, Nazarian et al.
U.S. Appl. No. 12/560,069, filed Aug. 26, 2010, Nadkarni et al.
U.S. Appl. No. 12/621,099, filed Sep. 30, 2010, Nadkarni et al.
U.S. Appl. No. 12/823,280, filed Jan. 6, 2011, Bentley et al.
U.S. Appl. No. 12/883,304, filed Mar. 17, 2011, Jangle et al.
U.S. Appl. No. 12/891,108, filed Mar. 17, 2011, Jangle et al.
U.S. Appl. No. 13/204,658, filed Nov. 24, 2011, Jangle et al.
U.S. Appl. No. 61/210,821, filed Mar. 24, 2009, Ram David Adva Fish.
U.S. Appl. No. 61/210,862, filed Mar. 24, 2009, Ram David Adva Fish.
U.S. Appl. No. 12/730,194, filed Sep. 23, 2010, Ram David Adva Fish.

(56) References Cited

OTHER PUBLICATIONS

U.S. Appl. No. 12/730,199, filed Sep. 23, 2010, Ram David Adva Fish.
U.S. Appl. No. 61/630,064, filed Dec. 5, 2011, Ram David Adva Fish.
U.S. Appl. No. 61/627,891, filed Oct. 13, 2011, Ram David Adva Fish.
U.S. Appl. No. 61/516,478, filed Apr. 5, 2011, Fish et al.
U.S. Appl. No. 61/516,477, filed Apr. 4, 2011, Ram David Adva Fish.
U.S. Appl. No. 13/405,241, filed Feb. 25, 2012, Rahman et al.
U.S. Appl. No. 13/158,372, filed Jun. 10, 2011, Fullam et al.
U.S. Appl. No. 13/158,416, filed Jun. 11, 2011, Drysdale et al.
U.S. Appl. No. 61/495,995, filed Jun. 11, 2011, Drysdale et al.
U.S. Appl. No. 13/135,728, filed Jul. 12, 2011, Drysdale et al.
U.S. Appl. No. 61/495,994, filed Jun. 11, 2011, Drysdale et al.
U.S. Appl. No. 13/181,512, filed Jun. 2, 2011, Rahman et al.
U.S. Appl. No. 61/495,997, filed Jun. 11, 2011, Drysdale et al.
U.S. Appl. No. 61/495,996, filed Jun. 11, 2011, Drysdale et al.
U.S. Appl. No. 61/511,541, filed Jul. 25, 2011, Jeffery Miao.
U.S. Appl. No. 13/247,975, filed Sep. 28, 2011, Sashittal et al.
U.S. Appl. No. 13/180,000, filed Jul. 11, 2011, Rahman et al.
U.S. Appl. No. 61/507,091, filed Jul. 21, 2011, Rahman et al.
U.S. Appl. No. 61/572,204, filed Jul. 12, 2011, Rahman et al.
U.S. Appl. No. 61/572,206, filed Jul. 12, 2011, Rahman et al.
U.S. Appl. No. 13/181,485, filed Jul. 12, 2011, Rahman et al.
U.S. Appl. No. 13/181,511, filed Jul. 12, 2011, Rahman et al.
U.S. Appl. No. 13/181,486, filed Jul. 12, 2011, Rahman et al.
U.S. Appl. No. 13/181,500, filed Jul. 12, 2011, Rahman et al.
U.S. Appl. No. 13/181,498, filed Jul. 12, 2011, Rahman et al.
U.S. Appl. No. 13/181,153, filed Jul. 12, 2011, Rahman et al.
U.S. Appl. No. 13/361,919, filed Jan. 30, 2012, Rahman et al.
U.S. Appl. No. 13/405,240, filed Feb. 25, 2012, Drysdale et al.

\* cited by examiner

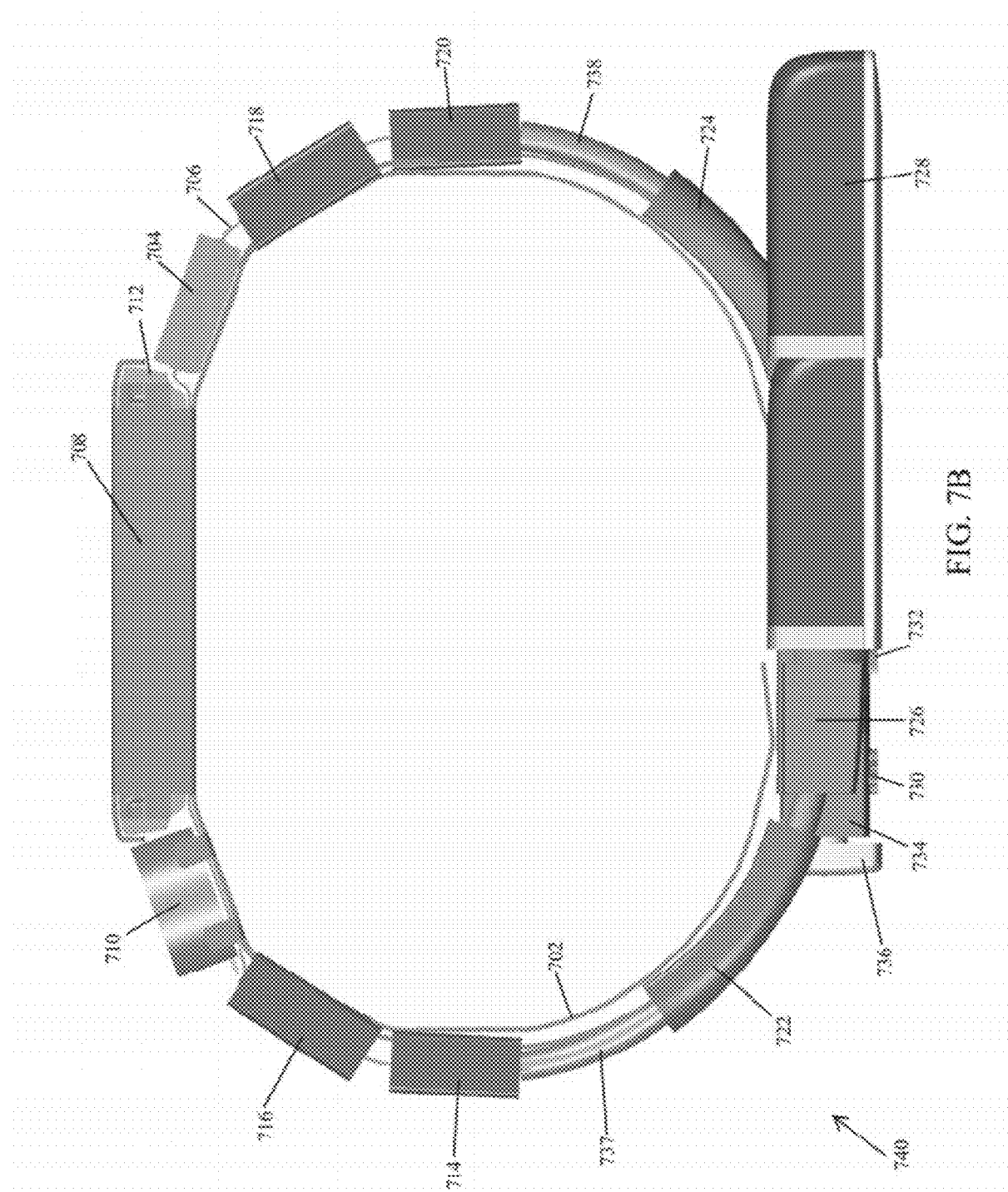

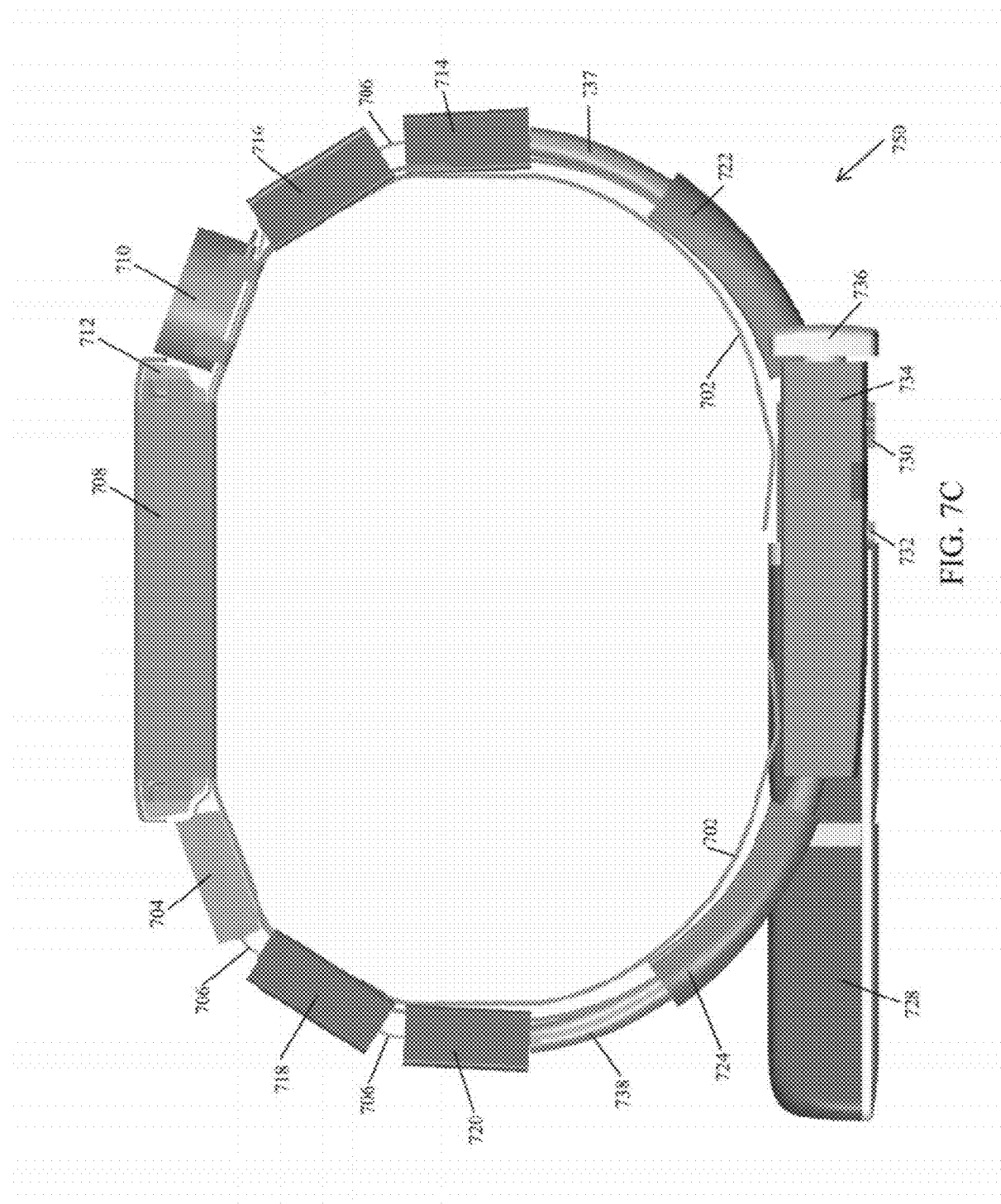

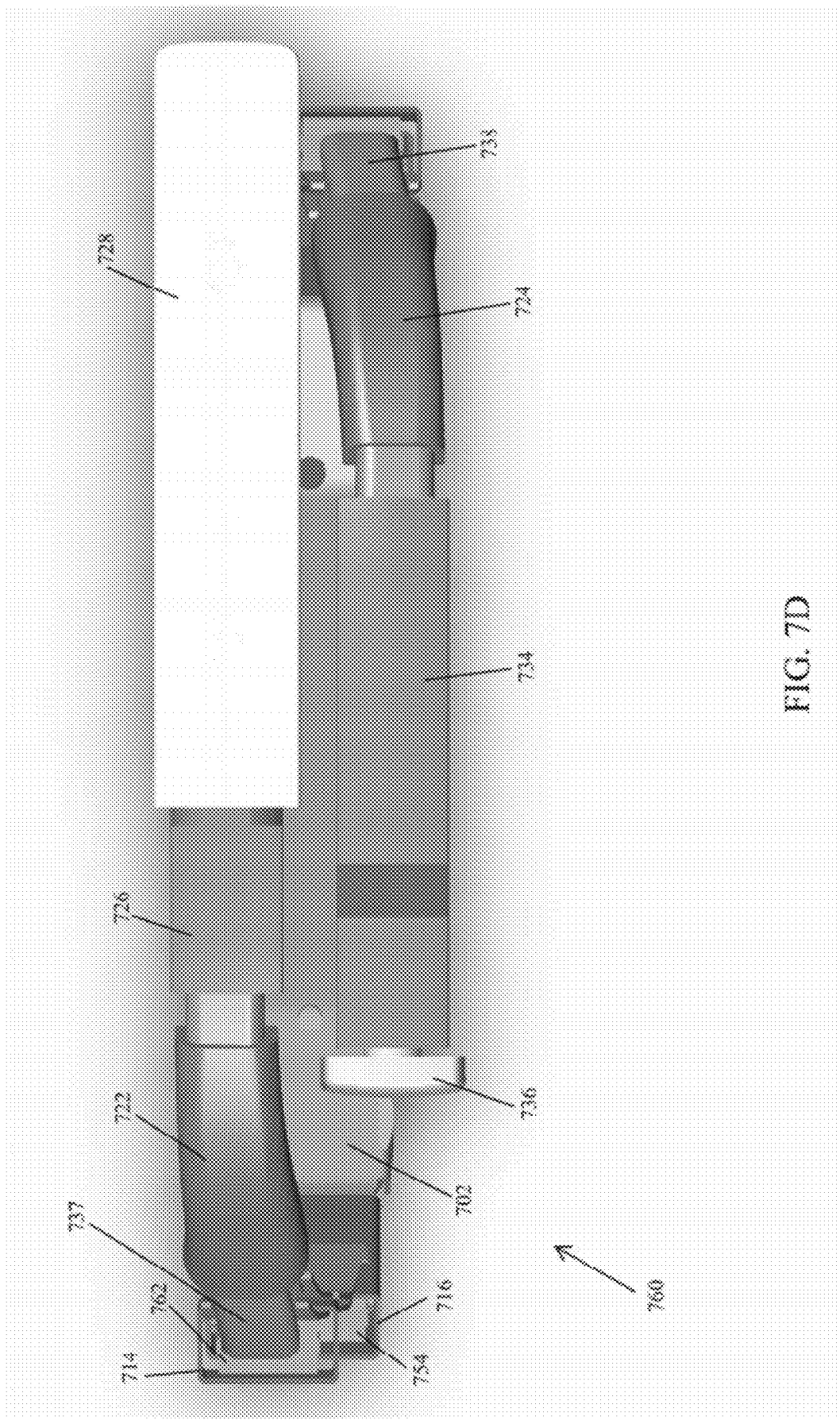

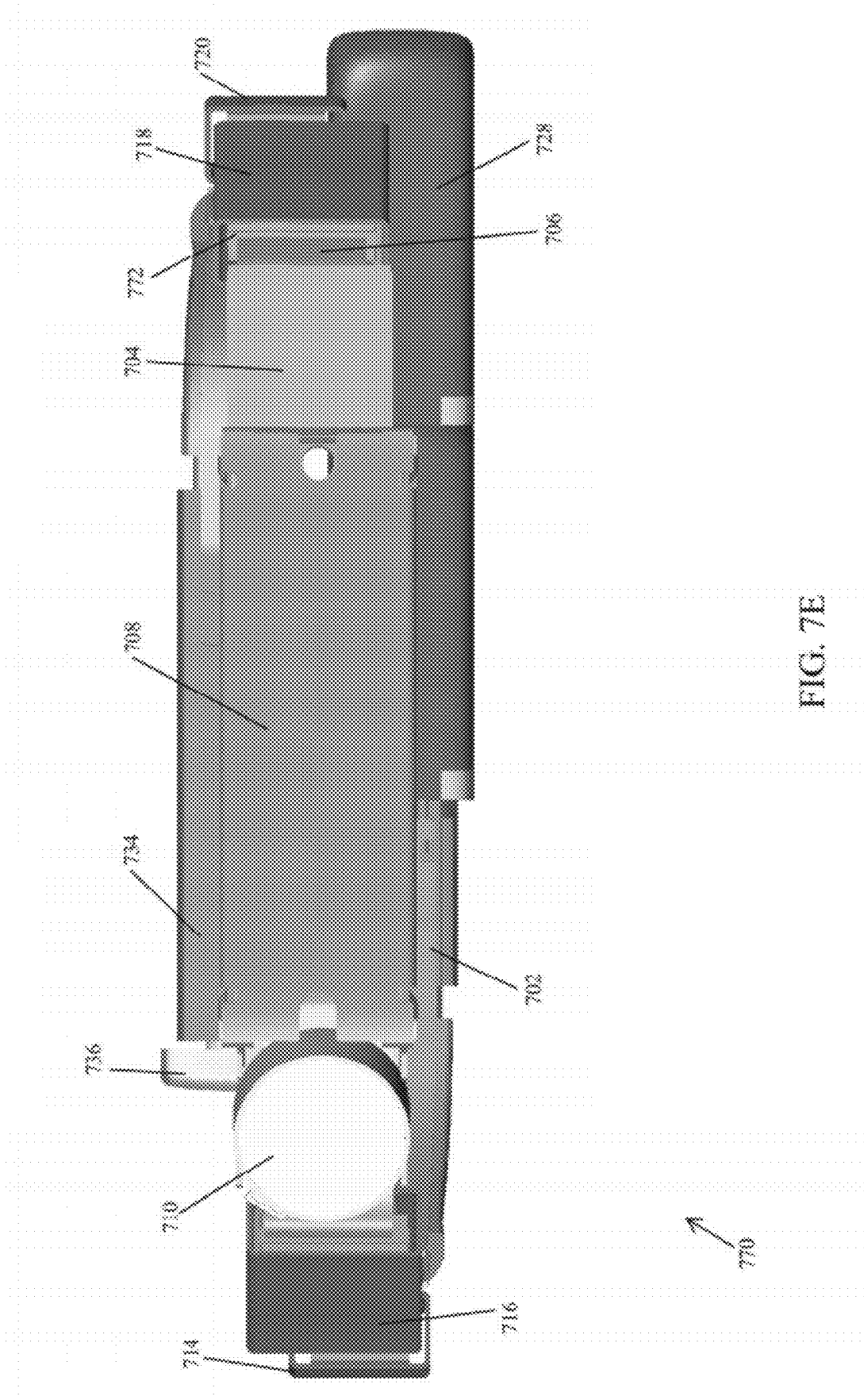

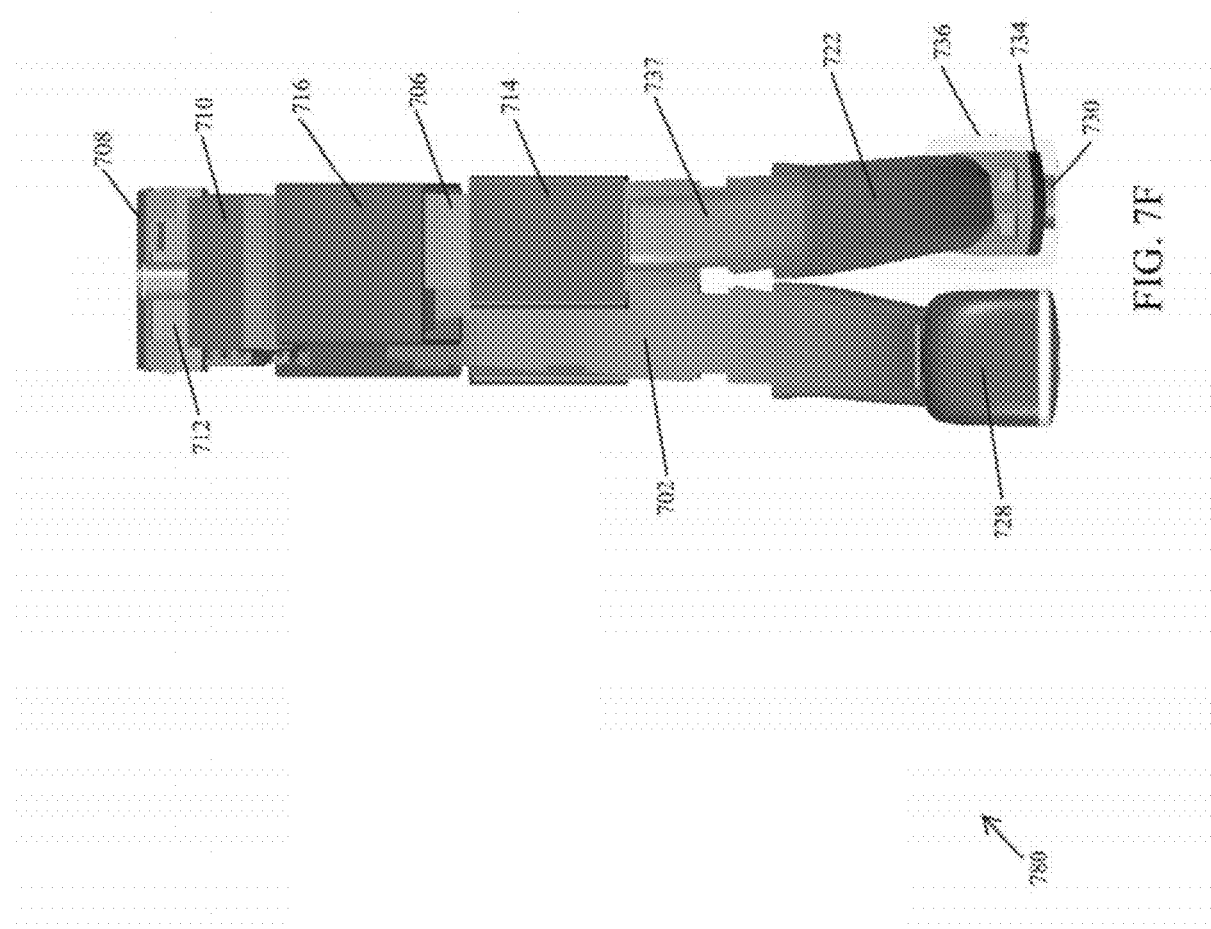

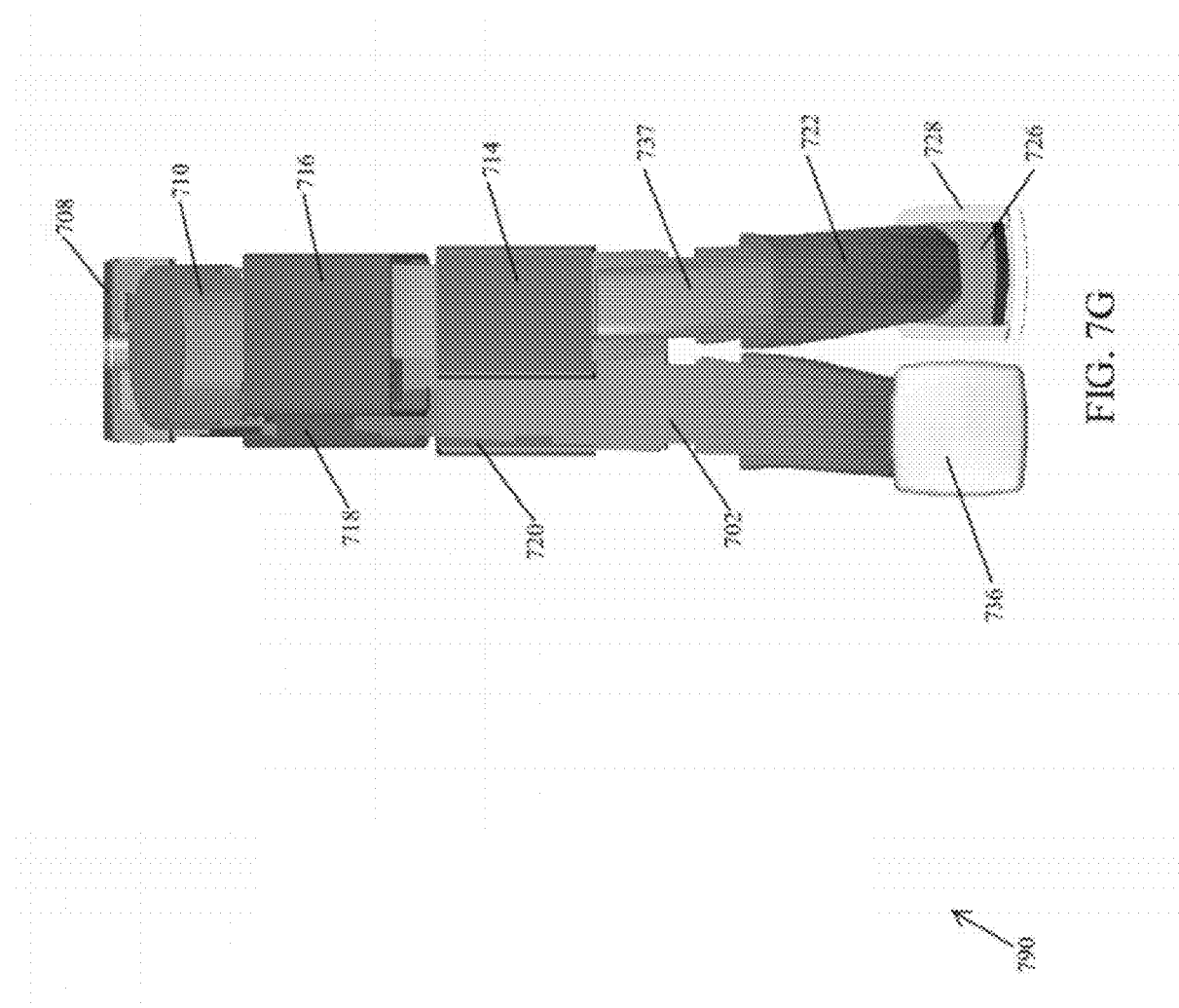

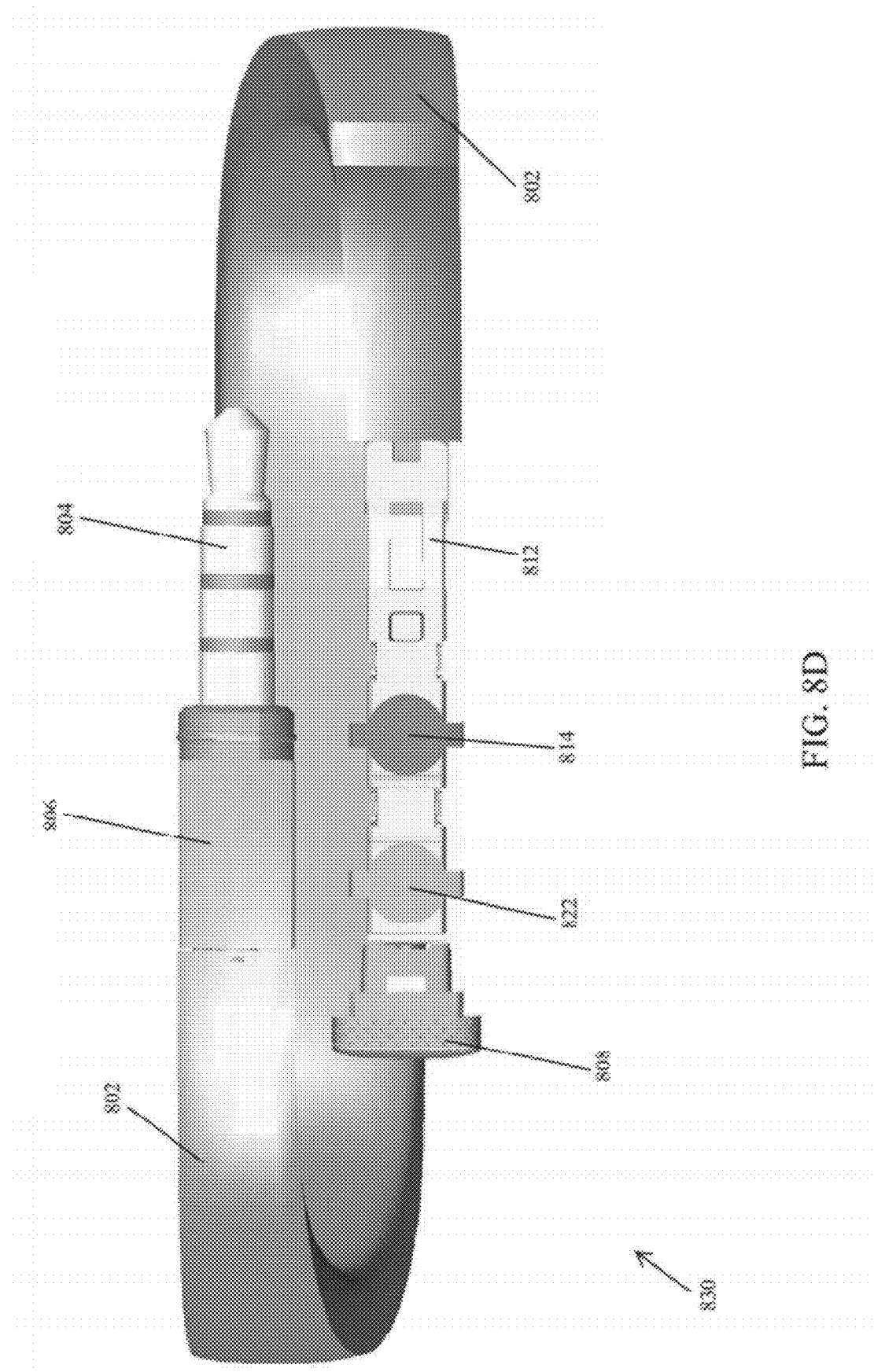

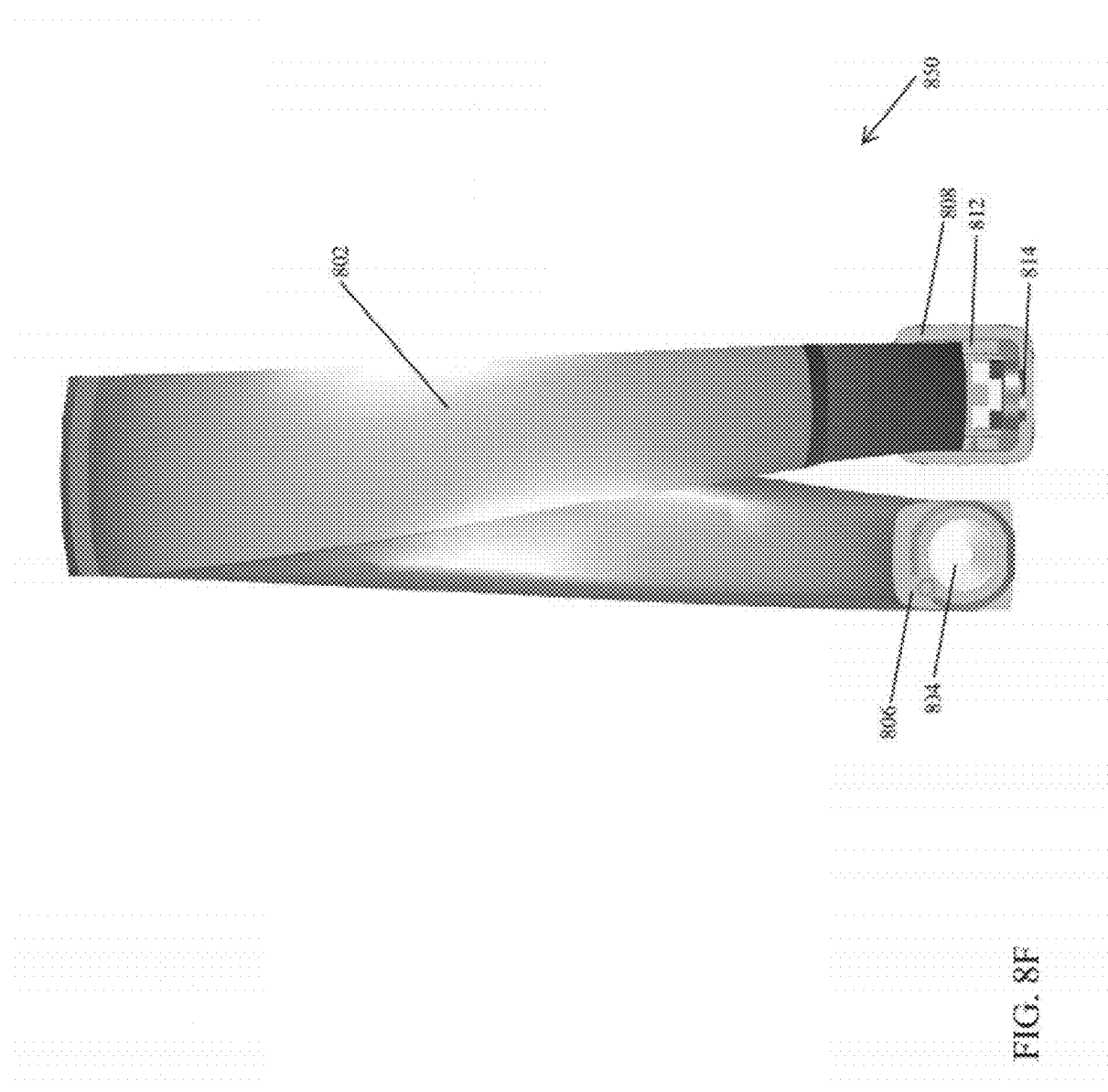

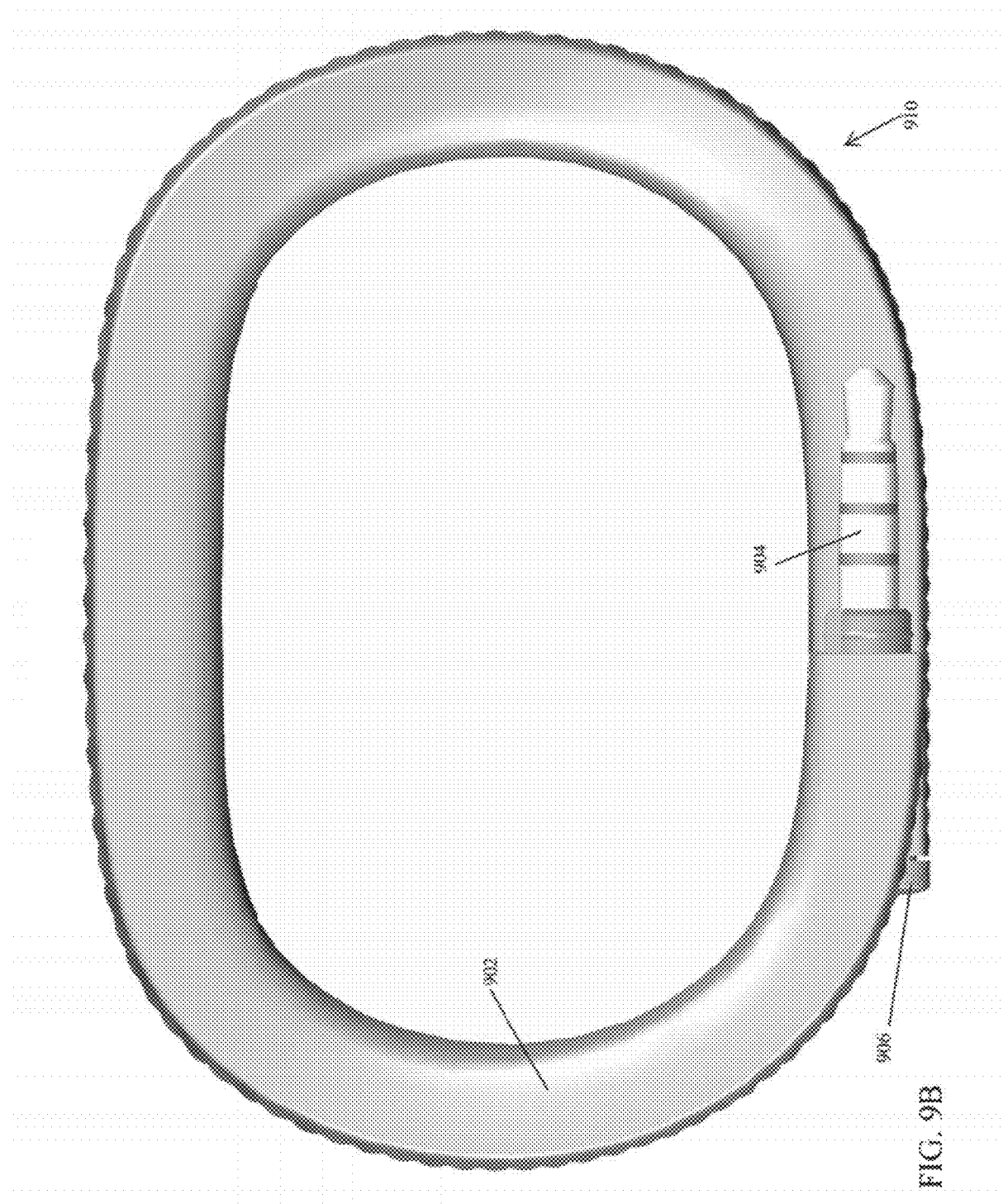

POWER MANAGEMENT IN A DATA-CAPABLE STRAPBAND

CROSS-REFERENCE TO RELATED APPLICATIONS

This application is a continuation-in-part of prior U.S. patent application Ser. No. 13/158,416, filed Jun. 11, 2011, which is a continuation-in-part of U.S. patent application Ser. No. 13/158,372, filed Jun. 10, 2011; this application claims the benefit of U.S. Provisional Patent Application No. 61/495,995, filed Jun. 11, 2011, U.S. Provisional Patent Application No. 61/495,994, U.S. Provisional Patent Application No. 61/495,997, filed Jun. 11, 2011, and U.S. Provisional Patent Application No. 61/495,996, filed Jun. 11, 2011; this application is related to U.S. patent application Ser. No. 13/180,000, filed Jul. 11, 2011, all of which are herein incorporated by reference for all purposes.

FIELD

Embodiments of the invention relates generally to electrical and electronic hardware, computer software, wired and wireless network communications, and computing devices. More specifically, structures and techniques for managing power generation, power consumption, and other power-related functions in a data-capable wearable or carried device that can be, for example, worn on or carried by a user's person.

BACKGROUND

With the advent of greater computing capabilities in smaller personal and/or portable form factors and an increasing number of applications (i.e., computer and Internet software or programs) for different uses, consumers (i.e., users) have access to large amounts of personal data. Information and data are often readily available, but poorly captured using conventional data capture devices. Conventional devices typically lack capabilities that can capture, analyze, communicate, or use data in a contextually-meaningful, comprehensive, and efficient manner. Further, conventional solutions are often limited to specific individual purposes or uses, demanding that users invest in multiple devices in order to perform different activities (e.g., a sports watch for tracking time and distance, a GPS receiver for monitoring a hike or run, a cyclometer for gathering cycling data, and others). Although a wide range of data and information is available, conventional devices and applications fail to provide effective solutions that comprehensively capture data for a given user across numerous disparate activities.

Some conventional solutions combine a small number of discrete functions. Functionality for data capture, processing, storage, or communication in conventional devices such as a watch or timer with a heart rate monitor or global positioning system ("GPS") receiver are available conventionally, but are expensive to manufacture and purchase. Other conventional solutions for combining personal data capture facilities often present numerous design and manufacturing problems such as size restrictions, specialized materials requirements, lowered tolerances for defects such as pits or holes in coverings for water-resistant or waterproof devices, unreliability, higher failure rates, increased manufacturing time, and expense. Subsequently, conventional devices such as fitness watches, heart rate monitors, GPS-enabled fitness monitors, health monitors (e.g., diabetic blood sugar testing units), digital voice recorders, pedometers, altimeters, and other conventional personal data capture devices are generally manufactured for conditions that occur in a single or small groupings of activities.

Generally, if the number of activities performed by conventional personal data capture devices increases, there is a corresponding rise in design and manufacturing requirements that results in significant consumer expense, which eventually becomes prohibitive to both investment and commercialization. Further, conventional personal data capture devices are not well-suited to address issues of power management, such as power issues related to transitioning from manufacture to operation by a user, and operating in various modes or during various activities in which a user is engaged.

Thus, what is needed is a solution for data capture devices without the limitations of conventional techniques to manage power in wearable communications devices and/or wearable devices with an array of sensors.

BRIEF DESCRIPTION OF THE DRAWINGS

Various embodiments or examples ("examples") are disclosed in the following detailed description and the accompanying drawings:

FIG. 7B illustrates a side view of an exemplary data-capable strapband;

FIG. 7C illustrates another side view of an exemplary data-capable strapband;

FIG. 7D illustrates a top view of an exemplary data-capable strapband;

FIG. 7E illustrates a bottom view of an exemplary data-capable strapband;

FIG. 7F illustrates a front view of an exemplary data-capable strapband;

FIG. 7G illustrates a rear view of an exemplary data-capable strapband;

FIG. 8D illustrates a top view of an exemplary data-capable strapband;

FIG. 8F illustrates a front view of an exemplary data-capable strapband;

FIG. 9B illustrates a side view of an exemplary data-capable strapband;

DETAILED DESCRIPTION

Various embodiments or examples may be implemented in numerous ways, including as a system, a process, an apparatus, a user interface, or a series of program instructions on a computer readable medium such as a computer readable storage medium or a computer network where the program instructions are sent over optical, electronic, or wireless communication links. In general, operations of disclosed processes may be performed in an arbitrary order, unless otherwise provided in the claims.

A detailed description of one or more examples is provided below along with accompanying figures. The detailed description is provided in connection with such examples, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description.

Figure 1:
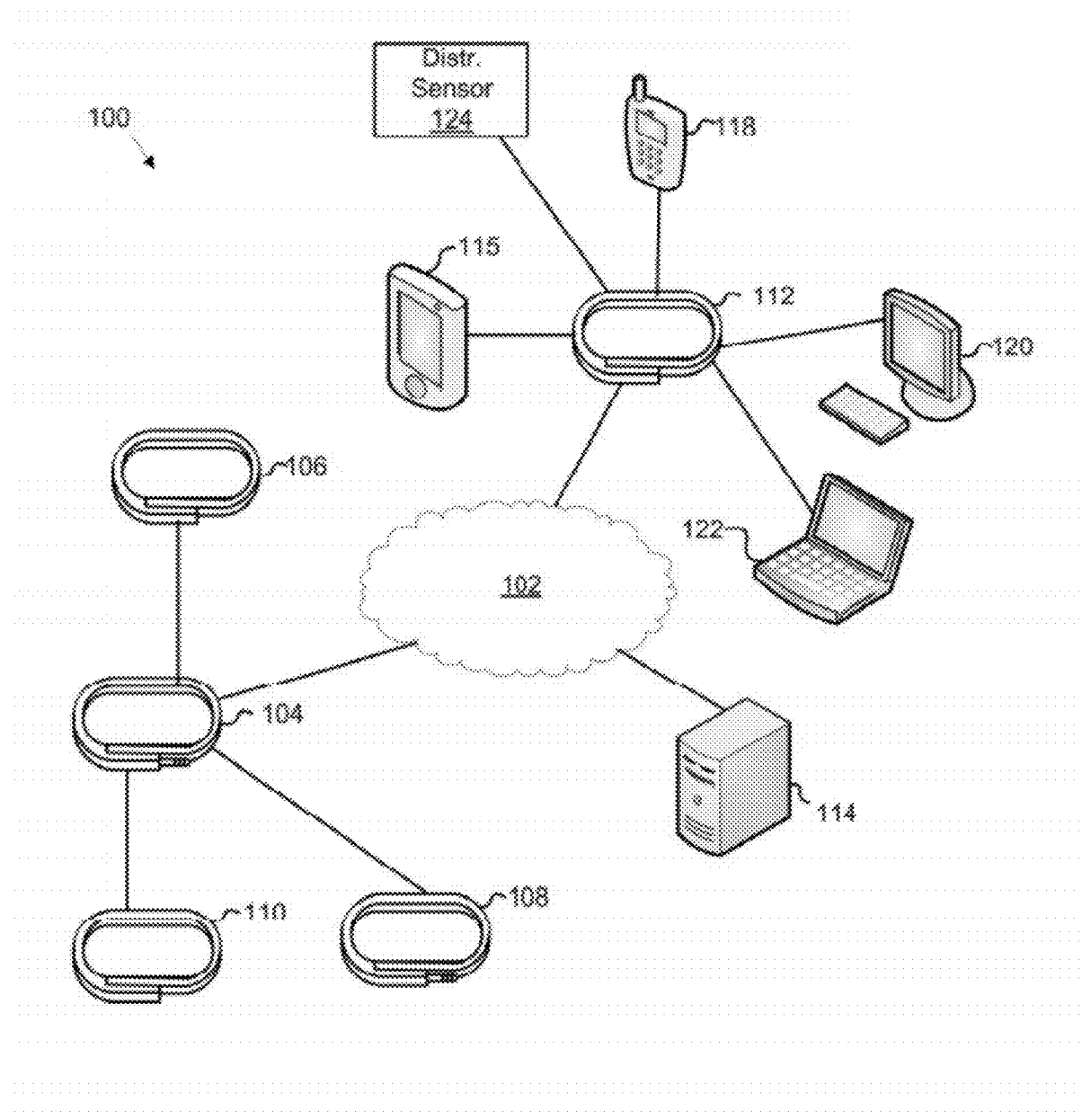
FIG. 1 illustrates an exemplary data-capable strapband system.

FIG. 1 illustrates an exemplary data-capable strapband system. Here, system 100 includes network 102, strapbands (hereafter "bands") 104-112, server 114, mobile computing device 115, mobile communications device 118, computer 120, laptop 122, and distributed sensor 124. Although used interchangeably, "strapband" and "band" may be used to refer to the same or substantially similar data-capable device that may be worn as a strap or band around an arm, leg, ankle, or other bodily appendage or feature. In other examples, bands 104-112 may be attached directly or indirectly to other items, organic or inorganic, animate, or static. In still other examples, bands 104-112 may be used differently.

As described above, bands 104-112 may be implemented as wearable personal data or data capture devices (e.g., data-capable devices) that are worn by a user around a wrist, ankle, arm, ear, or other appendage. Any of bands 104-112 can be attached to the body or affixed to clothing, or otherwise disposed at a relatively predetermined distance from a user's person. One or more facilities, sensing elements, or sensors, both active and passive, may be implemented as part of bands 104-112 in order to capture various types of data from different sources. Temperature, environmental, temporal, motion, electronic, electrical, chemical, or other types of sensors (including those described below in connection with FIG. 3) may be used in order to gather varying amounts of data, which may be configurable by a user, locally (e.g., using user interface facilities such as buttons, switches, motion-activated/detected command structures (e.g., accelerometer-gathered data from user-initiated motion of bands 104-112), and others) or remotely (e.g., entering rules or parameters in a website or graphical user interface ("GUI") that may be used to modify control systems or signals in firmware, circuitry, hardware, and software implemented (i.e., installed) on bands 104-112). Bands 104-112 may also be implemented as data-capable devices that are configured for data communication using various types of communications infrastructure and media, as described in greater detail below. Bands 104-112 may also be wearable, personal, non-intrusive, lightweight devices that are configured to gather large amounts of personally relevant data that can be used to improve user health, fitness levels, medical conditions, athletic performance, sleeping physiology, and physiological conditions, or used as a sensory-based user interface ("UI") to signal social-related notifications specifying the state of the user through vibration, heat, lights or other sensory based notifications. For example, a social-related notification signal indicating a user is on-line can be transmitted to a recipient, who in turn, receives the notification as, for instance, a vibration.

Using data gathered by bands 104-112, applications may be used to perform various analyses and evaluations that can generate information as to a person's physical (e.g., healthy, sick, weakened, activity level or other states), emotional, or mental state (e.g., an elevated body temperature or heart rate may indicate stress, a lowered heart rate and skin temperature, reduced movement (e.g., excessive sleeping or other abnormally/unexpectedly reduced amount of motion resulting from, for example, physical incapacitation or an inability to provide for sufficient motion) may indicate physiological depression caused by exertion or other factors, chemical data gathered from evaluating outgassing from the skin's surface may be analyzed to determine whether a person's diet is balanced or if various nutrients are lacking, salinity detectors may be evaluated to determine if high, lower, or proper blood sugar levels are present for diabetes management, and others). Generally, bands 104-112 may be configured to gather from sensors locally and remotely.

As an example, band 104 may capture (i.e., record, store, communicate (i.e., send or receive), process, or the like) data from various sources (i.e., sensors that are organic (i.e., installed, integrated, or otherwise implemented with band 104) or distributed (e.g., microphones on mobile computing device 115, mobile communications device 118, computer 120, laptop 122, distributed sensor 124, global positioning system ("GPS") satellites, or others, without limitation)) and exchange data with one or more of bands 106-112, server 114, mobile computing device 115, mobile communications device 118, computer 120, laptop 122, and distributed sensor 124. As shown here, a local sensor may be one that is incorporated, integrated, or otherwise implemented with hands 104-112. A remote or distributed sensor (e.g., mobile computing device 115, mobile communications device 118, computer 120, laptop 122, or, generally, distributed sensor 124) may be sensors that can be accessed, controlled, or otherwise used by bands 104-112. For example, band 112 may be configured to control devices that are also controlled by a given user (e.g. mobile computing device 115, mobile communications device 118, computer 120, laptop 122, and distributed sensor 124). For example, a microphone in mobile communications device 118 may be used to detect, for example, ambient audio data that is used to help identify a person's location or an ear clip, for example, can be affixed to the earlobe to record pulse or blood oxygen saturation levels. Additionally, a sensor implemented with a screen on mobile computing device 115 may be used to read a user's temperature or obtain a biometric signature while a user is interacting with data. A further example may include using data that is observed on computer 120 or laptop 122 that provides information as to a user's online behavior and the type of content that she is viewing, which may be used by bands 104-112. Regardless of the type or location of sensor used, data may be transferred to bands 104-112 by using, for example, an analog audio jack, digital adapter (e.g., USB, mini-USB), or other, without limitation, plug, or other type of connector that may be used to physically couple bands 104-112 to another device or system for transferring data and, in some examples, to provide power to recharge a battery (not shown). Alternatively, a wireless data communication interface or facility (e.g., a wireless radio that is configured to communicate data from bands 104-112 using one or more data communication protocols (e.g., IEEE 802.11a/b/g/n (WiFi), WiMax, ANT™, ZigBee®, Bluetooth®, Near Field Communications ("NFC"), and others)) may be used to receive or transfer data. Further, bands 104-112 may be configured to analyze, evaluate, modify, or otherwise use data gathered, either directly or indirectly.

In some examples, bands 104-112 may be configured to share data with each other or with an intermediary facility, such as a database, website, web service, or the like, which may be implemented by server 114. In some embodiments, server 114 can be operated by a third party providing, for example, social media-related services. Bands 104-112 and other related devices may exchange data with each other directly, or bands 104-112 may exchange data via a third party server, such as a third party like Facebook®, to provide social-media related services. Examples of other third party servers include those implemented by social networking services, including, but not limited to, services such as Yahoo! IM™, GTalk™, MSN Messenger™, Twitter® and other private or public social networks. The exchanged data may include personal physiological data and data derived from sensory-based user interfaces ("UI"). Server 114, in some examples, may be implemented using one or more processor-based computing devices or networks, including computing clouds, storage area networks ("SAN"), or the like. As shown, bands 104-112 may be used as a personal data or area network (e.g., "PDN" or "PAN") in which data relevant to a given user or band (e.g., one or more or bands 104-112) may be shared. As shown here, bands 104 and 112 may be configured to exchange data with each other over network 102 or indirectly using server 114. Users of bands 104 and 112 may direct a web browser hosted on a computer (e.g., computer 120, laptop 122, or the like) in order to access, view, modify, or perform other operations with data captured by bands 104 and 112. For example, two runners using bands 104 and 112 may be geographically remote (e.g., users are not geographically in close proximity locally such that bands being used by each user are in direct data communication), but wish to share data regarding their race times (pre, post, or in-race), personal records (i.e., "PR"), target split times, results, performance characteristics (e.g., target heart rate, target $VO_2$ max, and others), and other information. If both runners (i.e., bands 104 and 112) are engaged in a race on the same day, data can be gathered for comparative analysis and other uses. Further, data can be shared in substantially real-time (taking into account any latencies incurred by data transfer rates, network topologies, or other data network factors) as well as uploaded after a given activity or event has been performed. In other words, data can be captured by the user as it is worn and configured to transfer data using, for example, a wireless network connection (e.g., a wireless network interface card, wireless local area network ("LAN") card, connected through a cellular phone or other communications device, or the like. Data may also be shared in a temporally asynchronous manner in which a wired data connection (e.g., an analog audio plug (and associated software or firmware) configured to transfer digitally encoded data to encoded audio data that may be transferred between bands 104-112 and a plug configured to receive, encode/decode, and process data exchanged) may be used to transfer data from one or more hands 104-112 to various destinations (e.g., another of bands 104-112, server 114, mobile computing device 115, mobile communications device 118, computer 120, laptop 122, and distributed sensor 124). Bands 104-112 may be implemented with various types of wired and/or wireless communication facilities and are not intended to be limited to any specific technology. For example, data may be transferred from bands 104-112 using an analog audio plug (e.g., TRRS, TRS, or others). In other examples, wireless communication facilities using various types of data communication protocols (e.g., WiFi, Bluetooth®, ZigBee®, ANT™, and others) may be implemented as part of bands 104-112, which may include circuitry, firmware, hardware, radios, antennas, processors, microprocessors, memories, or other electrical, electronic, mechanical, or physical elements configured to enable data communication capabilities of various types and characteristics.

As data-capable devices, bands 104-112 may be configured to collect data from a wide range of sources, including onboard (not shown) and distributed sensors (e.g., server 114, mobile computing device 115, mobile communications device 118, computer 120, laptop 122, and distributed sensor 124) or other bands. Some or all data captured may be personal, sensitive, or confidential and various techniques for providing secure storage and access may be implemented. For example, various types of security protocols and algorithms may be used to encode data stored or accessed by bands 104-112. Examples of security protocols and algorithms include authentication, encryption, encoding, private and public key infrastructure, passwords, checksums, hash codes and hash functions (e.g., SHA, SHA-1, MD-5, and the like), or others may be used to prevent undesired access to data captured by bands 104-112. In other examples, data security for bands 104-112 may be implemented differently'

Bands 104-112 may be used as personal wearable, data capture devices that, when worn, are configured to identify a specific, individual user. By evaluating captured data, such as motion data from an accelerometer, or biometric data, such as heart-rate, skin galvanic response, or other biometric data, and using analysis techniques, both long and short-term (e.g., software packages or modules of any type, without limitation), a user may have a unique pattern of behavior or motion and/or biometric responses that can be used as a signature for identification. For example, bands 104-112 may gather data regarding an individual person's gait or other unique biometric, physiological or behavioral characteristics. Using, for example, distributed sensor 124, a biometric signature (e.g., fingerprint, retinal or iris vascular pattern, or others) may be gathered and transmitted to bands 104-112 that, when combined with other data, determines that a given user has been properly identified and, as such, authenticated. When bands 104-112 are worn, a user may be identified and authenticated to enable a variety of other functions such as accessing or modifying data, enabling wired or wireless data transmission facilities (i.e., allowing the transfer of data from bands 104-112), modifying functionality or functions of bands 104-112, authenticating financial transactions using stored data and information (e.g., credit card, PIN, card security numbers, and the like), running applications that allow for various operations to be performed (e.g., controlling physical security and access by transmitting a security code to a reader that, when authenticated, unlocks a door by turning off current to an electromagnetic lock, and others), and others. Different functions and operations beyond those described may be performed using bands 104-112, which can act as secure, personal, wearable, data-capable devices. The number, type, function, configuration, specifications, structure, or other features of system 100 and the above-described elements may be varied and are not limited to the examples provided.

Figure 2:
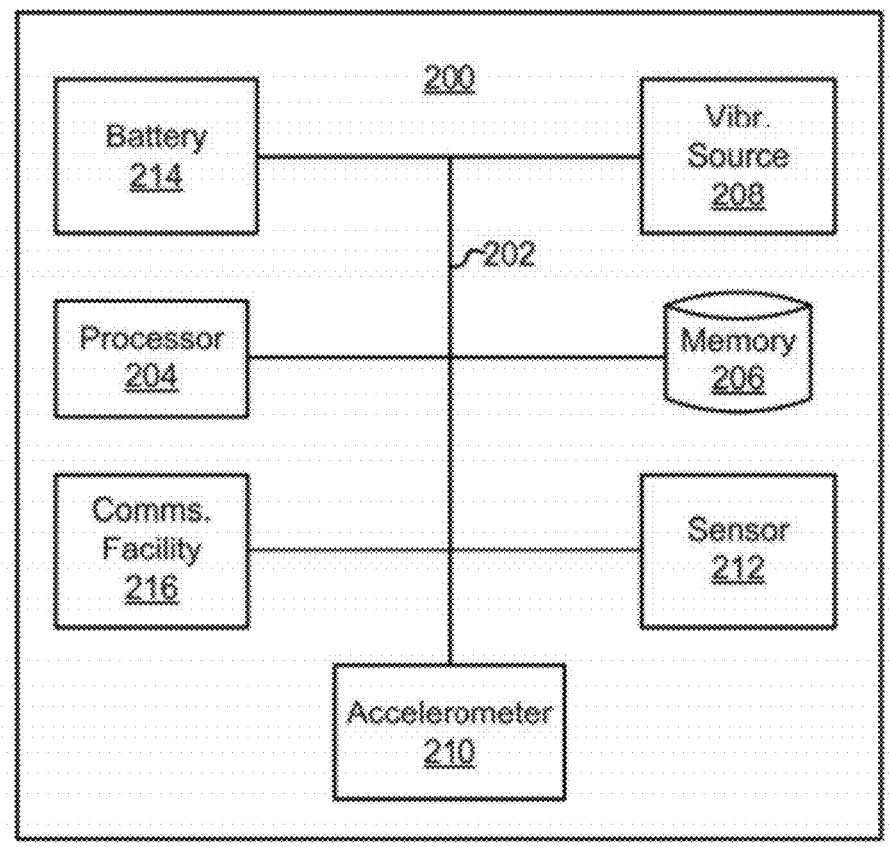
FIG. 2 illustrates a block diagram of an exemplary data-capable strapband.

FIG. 2 illustrates a block diagram of an exemplary data-capable strapband. Here, band 200 includes bus 202, processor 204, memory 206, vibration source 208, accelerometer 210, sensor 212, battery 214, and communications facility 216. In some examples, the quantity, type, function, structure, and configuration of band 200 and the elements (e.g., bus 202, processor 204, memory 206, vibration source 208, accelerometer 210, sensor 212, battery 214, and communications facility 216) shown may be varied and are not limited to the examples provided. As shown, processor 204 may be implemented as logic to provide control functions and signals to memory 206, vibration source 208, accelerometer 210, sensor 212, battery 214, and communications facility 216. Processor 204 may be implemented using any type of processor or microprocessor suitable for packaging within bands 104-112 (FIG. 1). Various types of microprocessors may be used to provide data processing capabilities for band 200 and are not limited to any specific type or capability. For example, a MSP430F5528-type microprocessor manufactured by Texas Instruments of Dallas, Tex. may be configured for data communication using audio tones and enabling the use of an audio plug-and-jack system (e.g., TRRS, TRS, or others) for transferring data captured by band 200. Further, different processors may be desired if other functionality (e.g., the type and number of sensors (e.g., sensor 212)) are varied. Data processed by processor 204 may be stored using, for example, memory 206.

In some examples, memory 206 may be implemented using various types of data storage technologies and standards, including, without limitation, read-only memory ("ROM"), random access memory ("RAM"), dynamic random access memory ("DRAM"), static random access memory ("SRAM"), static/dynamic random access memory ("SDRAM"), magnetic random access memory ("MRAM"), solid state, two and three-dimensional memories, Flash®, and others. Memory 206 may also be implemented using one or more partitions that are configured for multiple types of data storage technologies to allow for non-modifiable (i.e., by a user) software to be installed (e.g., firmware installed on ROM) while also providing for storage of captured data and applications using, for example, RAM. Once captured and/or stored in memory 206, data may be subjected to various operations performed by other elements of band 200.

Vibration source 208, in some examples, may be implemented as a motor or other mechanical structure that functions to provide vibratory energy that is communicated through band 200. As an example, an application stored on memory 206 may be configured to monitor a clock signal from processor 204 in order to provide timekeeping functions to band 200. If an alarm is set for a desired time, vibration source 208 may be used to vibrate when the desired time occurs. As another example, vibration source 208 may be coupled to a framework (not shown) or other structure that is used to translate or communicate vibratory energy throughout the physical structure of band 200. In other examples, vibration source 208 may be implemented differently.

Power may be stored in battery 214, which may be implemented as a battery, battery module, power management module, or the like. Power may also be gathered from local power sources such as solar panels, thermo-electric generators, and kinetic energy generators, among others that are alternatives power sources to external power for a battery. These additional sources can either power the system directly or can charge a battery, which, in turn, is used to power the system (e.g., of a strapband). In other words, battery 214 may include a rechargeable, expendable, replaceable, or other type of battery, but also circuitry, hardware, or software that may be used in connection with in lieu of processor 204 in order to provide power management, charge/recharging, sleep, or other functions. Further, battery 214 may be implemented using various types of battery technologies, including Lithium Ion ("LI"), Nickel Metal Hydride ("NiMH"), or others, without limitation. Power drawn as electrical current may be distributed from battery via bus 202, the latter of which may be implemented as deposited or formed circuitry or using other forms of circuits or cabling, including flexible circuitry. Electrical current distributed from battery 204 and managed by processor 204 may be used by one or more of memory 206, vibration source 208, accelerometer 210, sensor 212, or communications facility 216.

As shown, various sensors may be used as input sources for data captured by band 200. For example, accelerometer 210 may be used to gather data measured across one, two, or three axes of motion. In addition to accelerometer 210, other sensors (i.e., sensor 212) may be implemented to provide temperature, environmental, physical, chemical, electrical, or other types of sensed inputs. As presented here, sensor 212 may include one or multiple sensors and is not intended to be limiting as to the quantity or type of sensor implemented. Data captured by hand 200 using accelerometer 210 and sensor 212 or data requested from another source (i.e., outside of band 200) may also be exchanged, transferred, or otherwise communicated using communications facility 216. As used herein, "facility" refers to any, some, or all of the features and structures that are used to implement a given set of functions. For example, communications facility 216 may include a wireless radio, control circuit or logic, antenna, transceiver, receiver, transmitter, resistors, diodes, transistors, or other elements that are used to transmit and receive data from band 200. In some examples, communications facility 216 may be implemented to provide a "wired" data communication capability such as an analog or digital attachment, plug, jack, or the like to allow for data to be transferred. In other examples, communications facility 216 may be implemented to provide a wireless data communication capability to transmit digitally encoded data across one or more frequencies using various types of data communication protocols, without limitation. In still other examples, band 200 and the above-described elements may be varied in function, structure, configuration, or implementation and are not limited to those shown and described.

Figure 3:
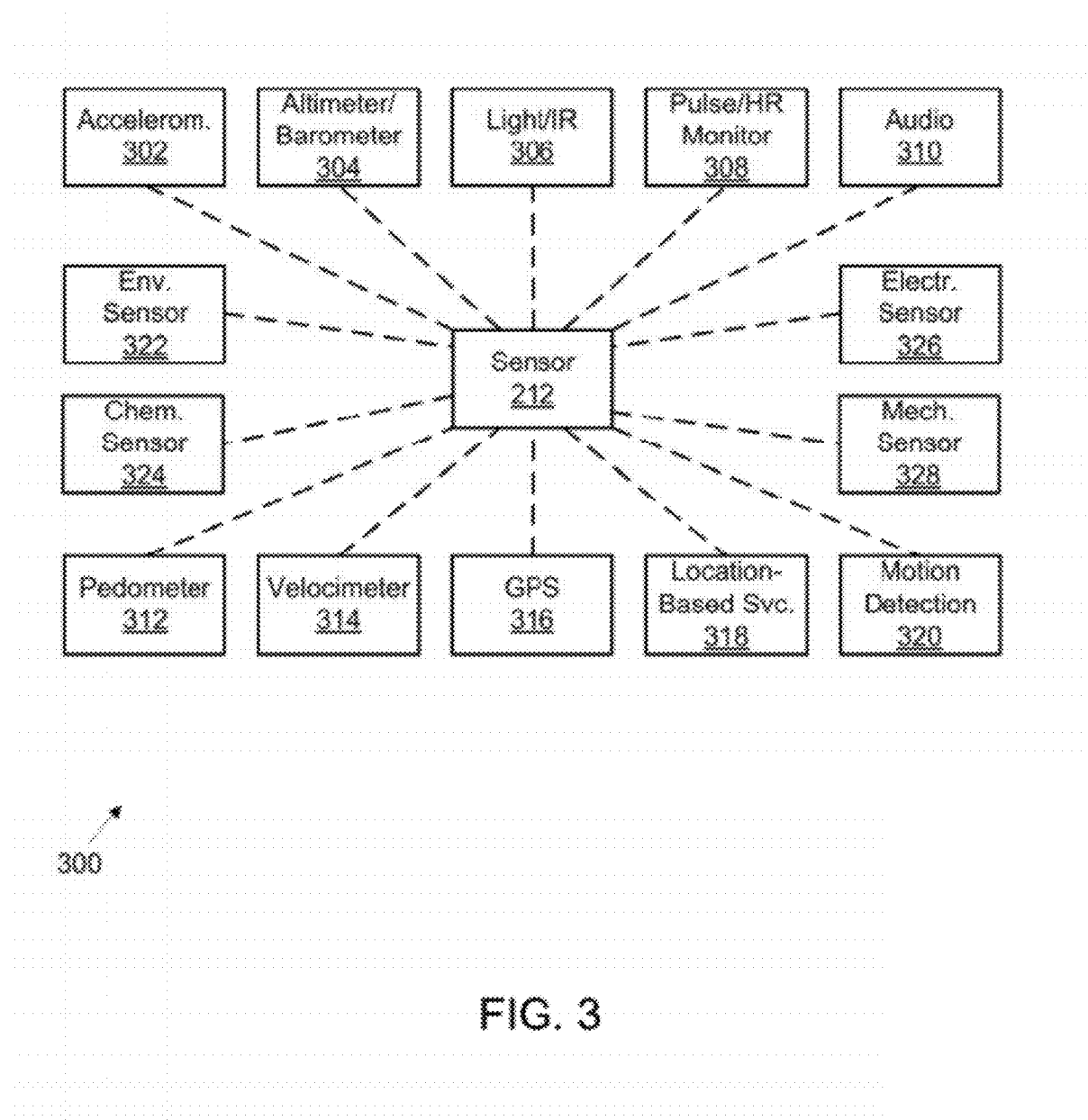
FIG. 3 illustrates sensors for use with an exemplary data-capable strapband.

FIG. 3 illustrates sensors for use with an exemplary data-capable strapband. Sensor 212 may be implemented using various types of sensors, some of which are shown. Like-numbered and named elements may describe the same or substantially similar element as those shown in other descriptions. Here, sensor 212 (FIG. 2) may be implemented as accelerometer 302, altimeter/barometer 304, light/infrared ("IR") sensor 306, pulse/heart rate ("HR") monitor 308, audio sensor (e.g., microphone, transducer, or others) 310, pedometer 312, velocimeter 314. GPS receiver 316, location-based service sensor (e.g., sensor for determining location within a cellular or micro-cellular network, which may or may not use GPS or other satellite constellations for fixing a position) 318, motion detection sensor 320, environmental sensor 322, chemical sensor 324, electrical sensor 326, or mechanical sensor 328.

As shown, accelerometer 302 may be used to capture data associated with motion detection along 1, 2, or 3-axes of measurement, without limitation to any specific type of specification of sensor. Accelerometer 302 may also be implemented to measure various types of user motion and may be configured based on the type of sensor, firmware, software, hardware, or circuitry used. As another example, altimeter/barometer 304 may be used to measure environment pressure, atmospheric or otherwise, and is not limited to any specification or type of pressure-reading device. In some examples, altimeter/barometer 304 may be an altimeter, a barometer, or a combination thereof. For example, altimeter/barometer 304 may be implemented as an altimeter for measuring above ground level ("AGL") pressure in hand 200, which has been configured for use by naval or military aviators. As another example, altimeter/barometer 304 may be implemented as a barometer for reading atmospheric pressure for marine-based applications. In other examples, altimeter/barometer 304 may be implemented differently.

Other types of sensors that may be used to measure light or photonic conditions include light/IR sensor 306, motion detection sensor 320, and environmental sensor 322, the latter of which may include any type of sensor for capturing data associated with environmental conditions beyond light. Further, motion detection sensor 320 may be configured to detect motion using a variety of techniques and technologies, including, but not limited to comparative or differential light analysis (e.g., comparing foreground and background lighting), sound monitoring, or others. Audio sensor 310 may be implemented using any type of device configured to record or capture sound.

In some examples, pedometer 312 may be implemented using devices to measure various types of data associated with pedestrian-oriented activities such as running or walking. Footstrikes, stride length, stride length or interval, time, and other data may be measured. Velocimeter 314 may be implemented, in some examples, to measure velocity (e.g., speed and directional vectors) without limitation to any particular activity. Further, additional sensors that may be used as sensor 212 include those configured to identify or obtain location-based data. For example. GPS receiver 316 may be used to obtain coordinates of the geographic location of band 200 using, for example, various types of signals transmitted by civilian and/or military satellite constellations in low, medium, or high earth orbit (e.g., "LEO," "MEO," or "GEO"). In other examples, differential GPS algorithms may also be implemented with GPS receiver 316, which may be used to generate more precise or accurate coordinates. Still further, location-based services sensor 318 may be implemented to obtain location-based data including, but not limited to location, nearby services or items of interest, and the like. As an example, location-based services sensor 318 may be configured to detect an electronic signal, encoded or otherwise, that provides information regarding a physical locale as band 200 passes. The electronic signal may include, in some examples, encoded data regarding the location and information associated therewith. Electrical sensor 326 and mechanical sensor 328 may be configured to include other types (e.g., haptic, kinetic, piezoelectric, piezomechanical, pressure, touch, thermal, and others) of sensors for data input to hand 200, without limitation. Other types of sensors apart from those shown may also be used, including magnetic flux sensors such as solid-state compasses and the like, including gyroscopic sensors. While the present illustration provides numerous examples of types of sensors that may be used with band 200 (FIG. 2), others not shown or described may be implemented with or as a substitute for any sensor shown or described.

Figure 4:
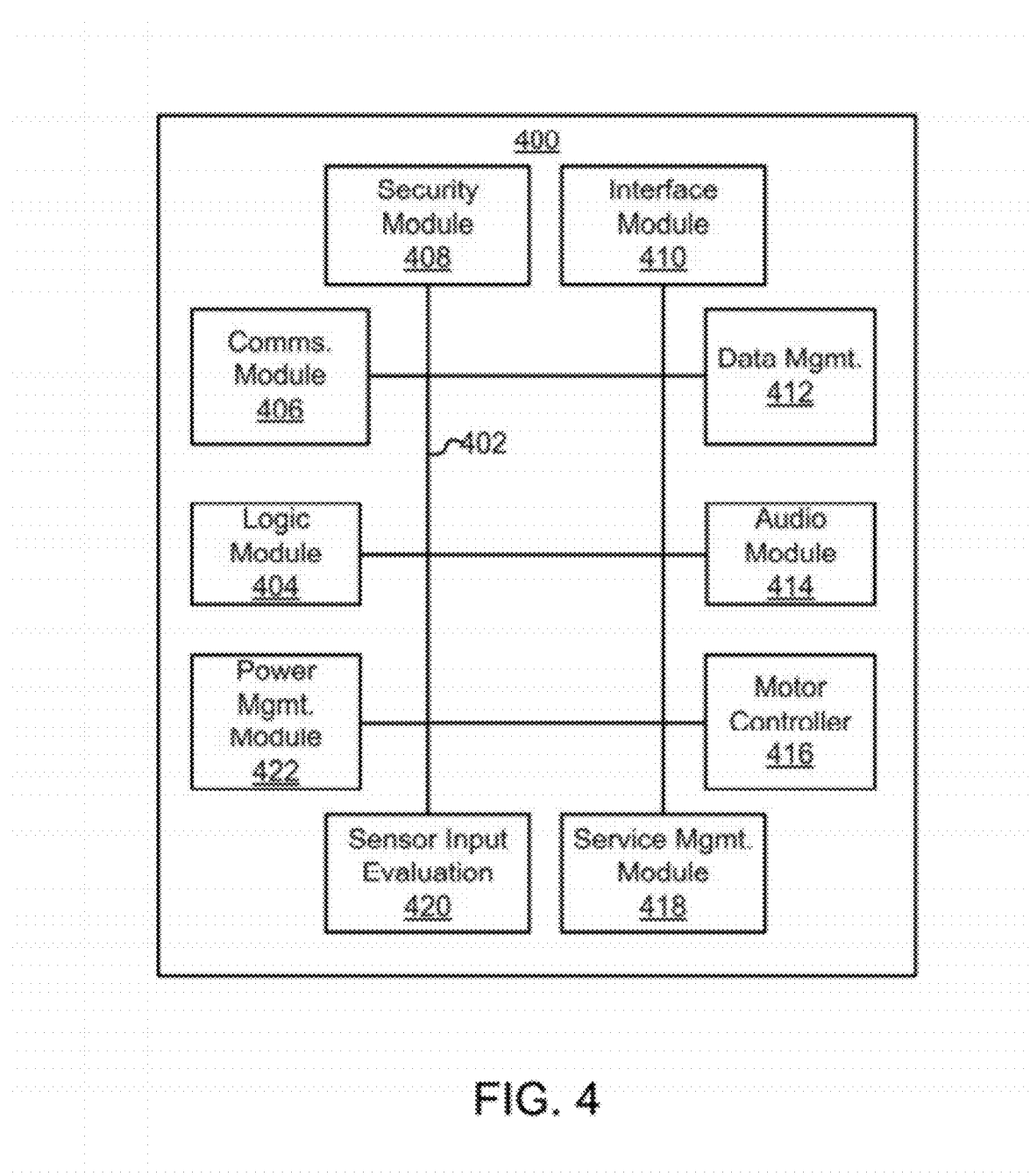
FIG. 4 illustrates an application architecture for an exemplary data-capable strapband.

FIG. 4 illustrates an application architecture for an exemplary data-capable strapband. Here, application architecture 400 includes bus 402, logic module 404, communications module 406, security module 408, interface module 410, data management 412, audio module 414, motor controller 416, service management module 418, sensor input evaluation module 420, and power management module 422. In some examples, application architecture 400 and the above-listed elements (e.g., bus 402, logic module 404, communications module 406, security module 408, interlace module 410, data management 412, audio module 414, motor controller 416, service management module 418, sensor input evaluation module 420, and power management module 422) may be implemented as software using various computer programming and formatting languages such as Java, C++, C, and others. As shown here, logic module 404 may be firmware or application software that is installed in memory 206 (FIG. 2) and executed by processor 204 (FIG. 2). Included with logic module 404 may be program instructions or code (e.g., source, object, binary executables, or others) that, when initiated, called, or instantiated, perform various functions.

For example, logic module 404 may be configured to send control signals to communications module 406 in order to transfer, transmit, or receive data stored in memory 206, the latter of which may be managed by a database management system ("DBMS") or utility in data management module 412. As another example, security module 408 may be controlled by logic module 404 to provide encoding, decoding, encryption, authentication, or other functions to band 200 (FIG. 2). Alternatively, security module 408 may also be implemented as an application that, using data captured from various sensors and stored in memory 206 (and accessed by data management module 412) may be used to provide identification functions that enable band 200 to passively identify a user or wearer of band 200. Still further, various types of security software and applications may be used and are not limited to those shown and described.

Interface module 410, in some examples, may be used to manage user interface controls such as switches, buttons, or other types of controls that enable a user to manage various functions of band 200. For example, a 4-position switch may be turned to a given position that is interpreted by interface module 410 to determine the proper signal or feedback to send to logic module 404 in order to generate a particular result. In other examples, a button (not shown) may be depressed that allows a user to trigger or initiate certain actions by sending another signal to logic module 404. Still further, interface module 410 may be used to interpret data from, for example, accelerometer 210 (FIG. 2) to identify specific movement or motion that initiates or triggers a given response. In other examples, interface module 410 may be implemented differently in function, structure, or configuration and is not limited to those shown and described.

As shown, audio module 414 may be configured to manage encoded or unencoded data gathered from various types of audio sensors. In some examples, audio module 414 may include one or more codecs that are used to encode or decode various types of audio waveforms. For example, analog audio input may be encoded by audio module 414 and, once encoded, sent as a signal or collection of data packets, messages, segments, frames, or the like to logic module 404 for transmission via communications module 406. In other examples, audio module 414 may be implemented differently in function, structure, configuration, or implementation and is not limited to those shown and described. Other elements that may be used by band 200 include motor controller 416, which may be firmware or an application to control a motor or other vibratory energy source (e.g., vibration source 208 (FIG. 2)). Power used for band 200 may be drawn from battery 214 (FIG. 2) and managed by power management module 422, which may be firmware or an application used to manage, with or without user input, how power is consumer, conserved, or otherwise used by band 200 and the above-described elements, including one or more sensors (e.g., sensor 212 (FIG. 2), sensors 302-328 (FIG. 3)). With regard to data captured, sensor input evaluation module 420 may be a software engine or module that is used to evaluate and analyze data received from one or more inputs (e.g., sensors 302-328) to band 200. When received, data may be analyzed by sensor input evaluation module 420, which may include custom or "off-the-shelf" analytics packages that are configured to provide application-specific analysis of data to determine trends, patterns, and other useful information. In other examples, sensor input module 420 may also include firmware or software that enables the generation of various types and formats of reports for presenting data and any analysis performed thereupon.

Another element of application architecture 400 that may be included is service management module 418. In some examples, service management module 418 may be firmware, software, or an application that is configured to manage various aspects and operations associated with executing software-related instructions for band 200. For example, libraries or classes that are used by software or applications on band 200 may be served from an online or networked source. Service management module 418 may be implemented to manage how and when these services are invoked in order to ensure that desired applications are executed properly within application architecture 400. As discrete sets, collections, or groupings of functions, services used by band 200 for various purposes ranging from communications to operating systems to call or document libraries may be managed by service management module 418. Alternatively, service management module 418 may be implemented differently and is not limited to the examples provided herein. Further, application architecture 400 is an example of a software/system/application-level architecture that may be used to implement various software-related aspects of band 200 and may be varied in the quantity, type, configuration, function, structure, or type of programming or formatting languages used, without limitation to any given example.

Figure 5A:
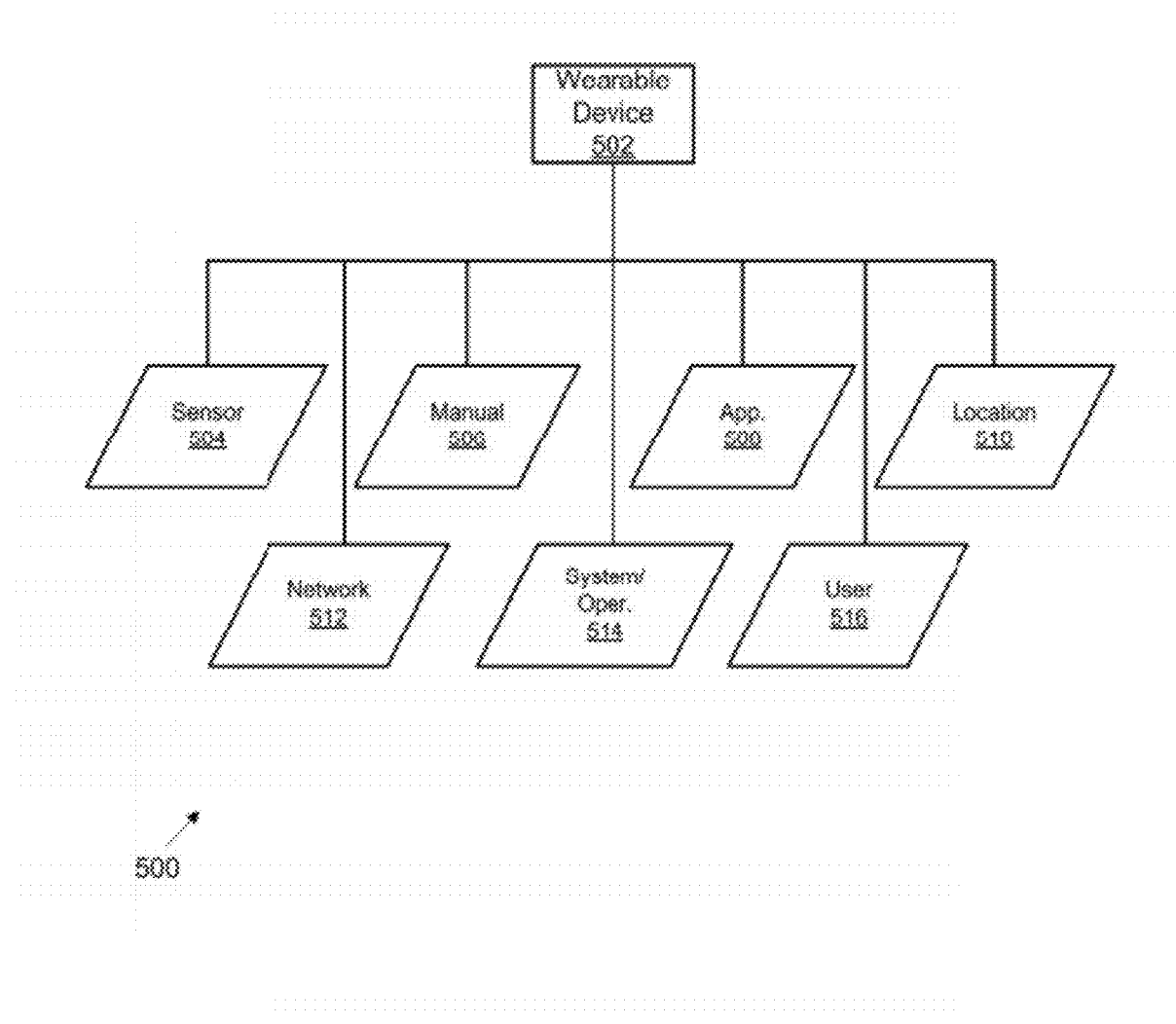
FIG. 5A illustrates representative data types for use with an exemplary data-capable strapband.

FIG. 5A illustrates representative data types for use with an exemplary data-capable strapband. Here, wearable device 502 may capture various types of data, including, but not limited to sensor data 504, manually-entered data 506, application data 508, location data 510, network data 512, system/operating data 514, and user data 516. Various types of data may be captured from sensors, such as those described above in connection with FIG. 3. Manually-entered data, in some examples, may be data or inputs received directly and locally by band 200 (FIG. 2). In other examples, manually-entered data may also be provided through a third-party website that stores the data in a database and may be synchronized from server 114 (FIG. 1) with one or more of bands 104-112. Other types of data that may be captured including application data 508 and system/operating data 514, which may be associated with firmware, software, or hardware installed or implemented on band 200. Further, location data 510 may be used by wearable device 502, as described above. User data 516, in some examples, may be data that include profile data, preferences, rules, or other information that has been previously entered by a given-user of wearable device 502. Further, network data 512 may be data is captured by wearable device with regard to routing tables, data paths, network or access availability (e.g., wireless network access availability), and the like. Other types of data may be captured by wearable device 502 and are not limited to the examples shown and described. Additional context-specific examples of types of data captured by bands 104-112 (FIG. 1) are provided below.

Figure 5B:
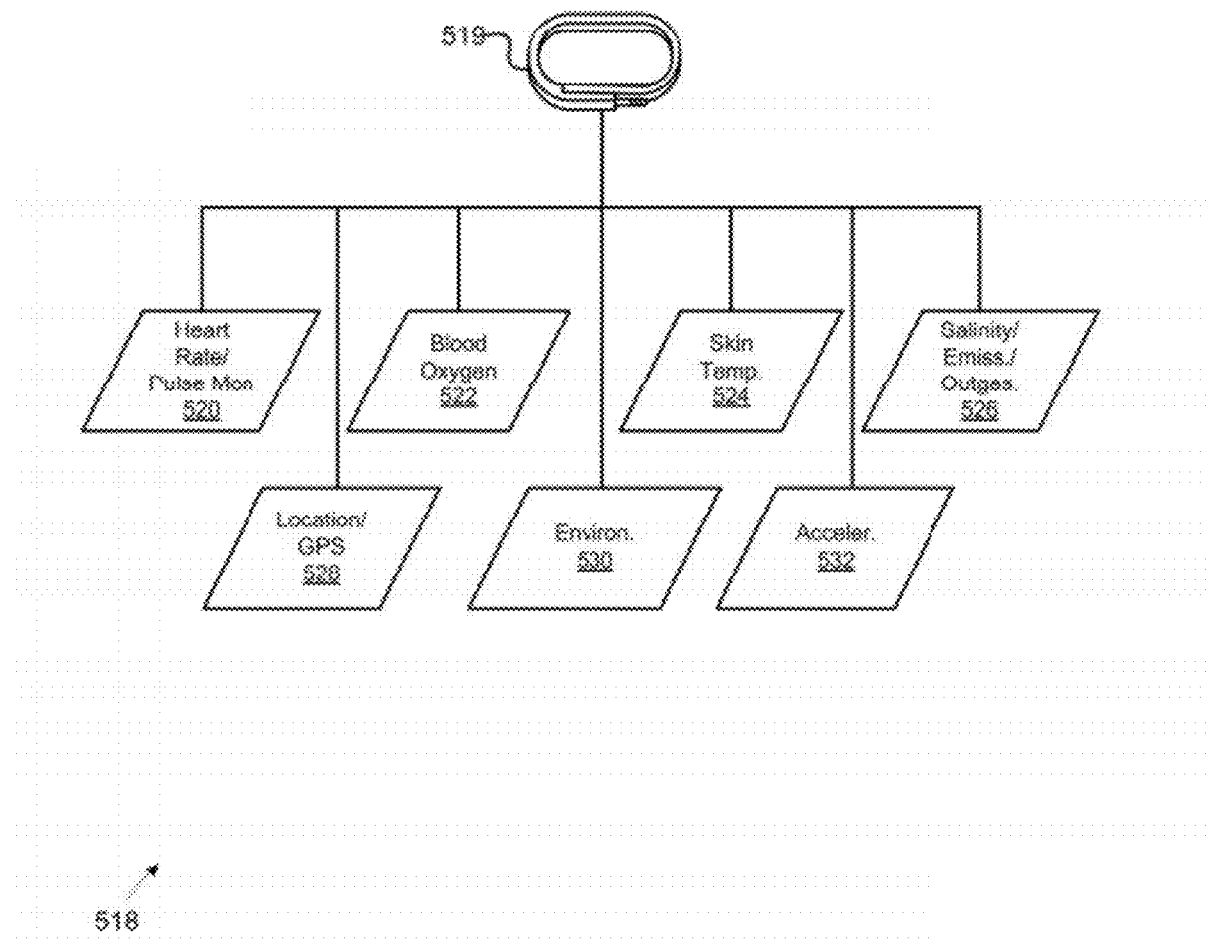
FIG. 5B illustrates representative data types for use with an exemplary data-capable strapband in fitness-related activities.

FIG. 5B illustrates representative data types for use with an exemplary data-capable strapband in fitness-related activities. Here, band 519 may be configured to capture types (i.e., categories) of data such as heart rate/pulse monitoring data 520, blood oxygen level data 522, skin temperature data 524, salinity/emission/outgassing data 526, location/GPS data 528, environmental data 530, and accelerometer data 532. As an example, a runner may use or wear band 519 to obtain data associated with his physiological condition (i.e., heart rate/pulse monitoring data 520, skin temperature, salinity/emission/outgassing data 526, among others), athletic efficiency (i.e., blood oxygen saturation data 522), and performance (i.e., location/GPS data 528 (e.g., distance or laps run), environmental data 530 (e.g., ambient temperature, humidity, pressure, and the like), accelerometer 532 (e.g., biomechanical information, including gait, stride, stride length, among others)). Other or different types of data may be captured by band 519, but the above-described examples are illustrative of some types of data that may be captured by band 519. Further, data captured may be uploaded to a website or online/networked destination for storage and other uses. For example, fitness-related data may be used by applications that are downloaded from a "fitness marketplace" where athletes may find, purchase, or download applications for various uses. Some applications may be activity-specific and thus may be used to modify or alter the data capture capabilities of band 519 accordingly. For example, a fitness marketplace may be a website accessible by various types of mobile and non-mobile clients to locate applications for different exercise or fitness categories such as running, swimming, tennis, golf, baseball, football, fencing, and many others. When downloaded, a fitness marketplace may also be used with user-specific accounts to manage the retrieved applications as well as usage with band 519 or to use the data to provide services such as online personal coaching, targeted advertisements, or other information provided to or on behalf of the user as a function of data generated in relation to hand 519. More, fewer, or different types of data may be captured for fitness-related activities.

Figure 5C:
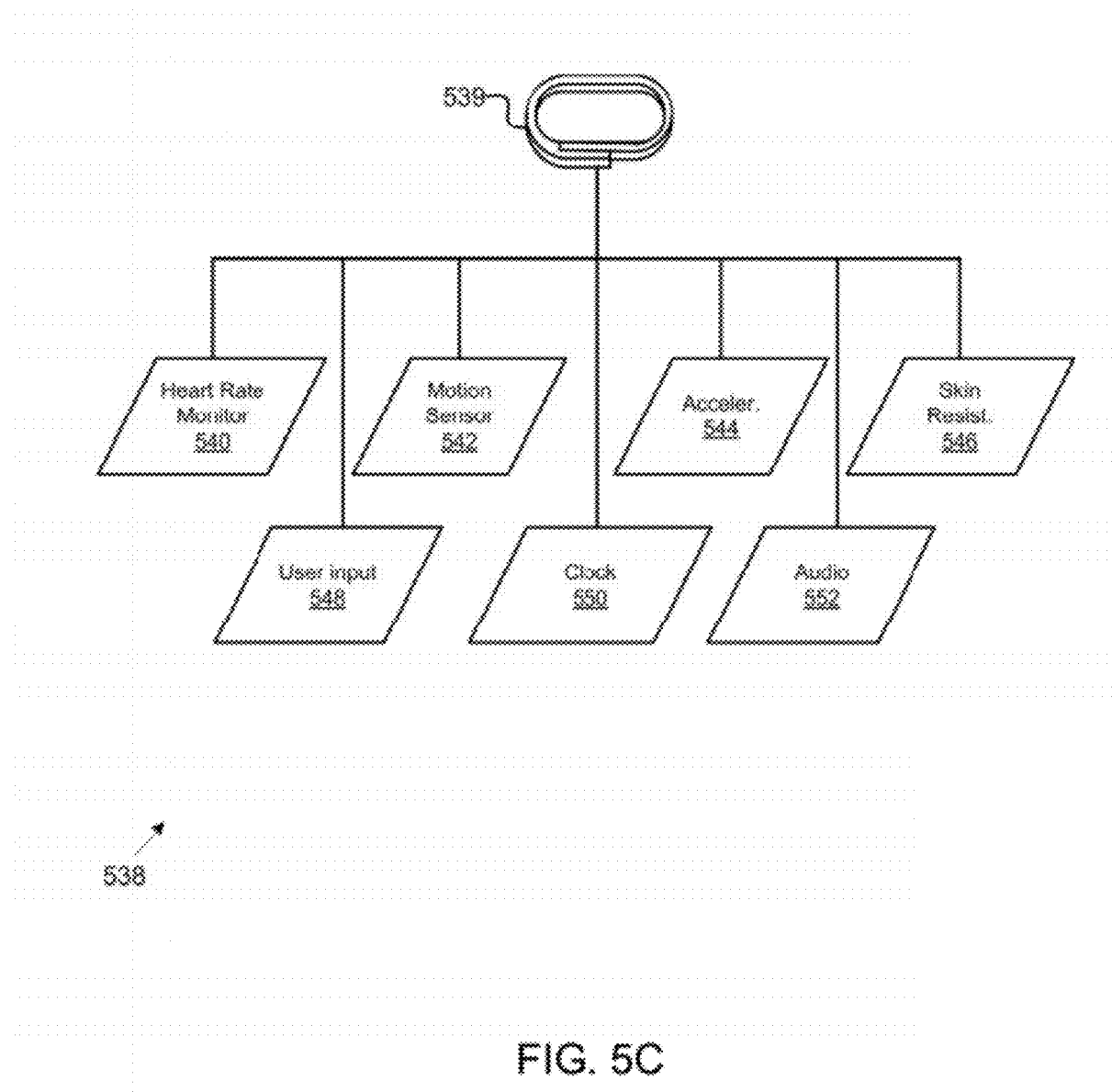
FIG. 5C illustrates representative data types for use with an exemplary data-capable strapband in sleep management activities.

FIG. 5C illustrates representative data types for use with an exemplary data-capable strapband in sleep management activities. Here, hand 539 may be used for sleep management purposes to track various types of data, including heart rate monitoring data 540, motion sensor data 542, accelerometer data 544, skin resistivity data 546, user input data 548, clock data 550, and audio data 552. In some examples, heart rate monitor data 540 may be captured to evaluate rest, waking, or various states of sleep. Motion sensor data 542 and accelerometer data 544 may be used to determine whether a user of band 539 is experiencing a restful or fitful sleep. For example, some motion sensor data 542 may be captured by a light sensor that measures ambient or differential light patterns in order to determine whether a user is sleeping on her front, side, or back. Accelerometer data 544 may also be captured to determine whether a user is experiencing gentle or violent disruptions when sleeping, such as those often found in afflictions of sleep apnea or other sleep disorders. Further, skin resistivity data 546 may be captured to determine whether a user is ill (e.g., running a temperature, sweating, experiencing chills, clammy skin, and others). Still further, user input data may include data input by a user as to how and whether band 539 should trigger vibration source 208 (FIG. 2) to wake a user at a given time or whether to use a series of increasing or decreasing vibrations to trigger a waking state. Clock data (550) may be used to measure the duration of sleep or a finite period of time in which a user is at rest. Audio data may also be captured to determine whether a user is snoring and, if so, the frequencies and amplitude therein may suggest physical conditions that a user may be interested in knowing (e.g., snoring, breathing interruptions, talking in one's sleep, and the like). More, fewer, or different types of data may be captured for sleep management-related activities.

Figure 5D:
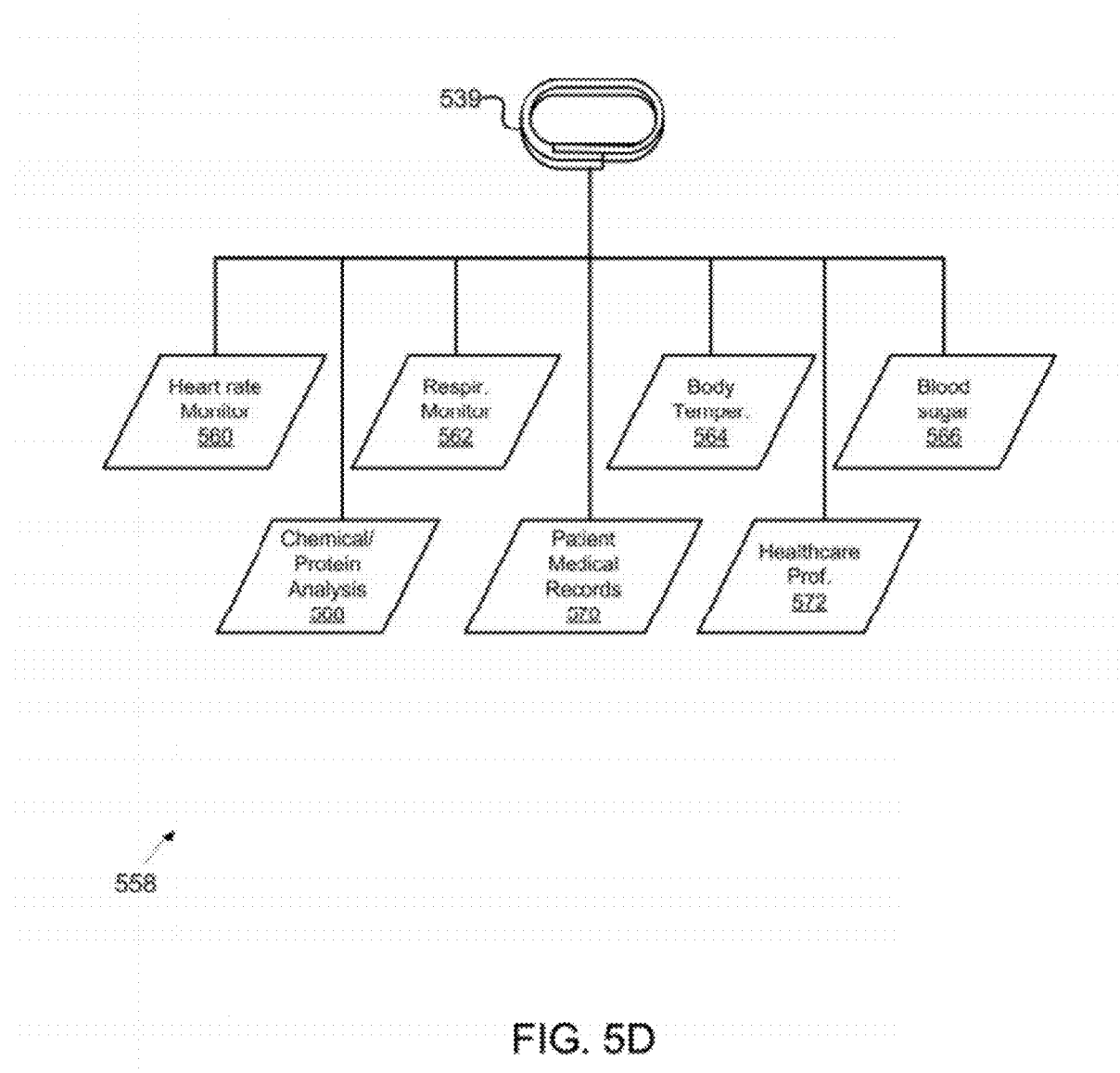
FIG. 5D illustrates representative data types for use with an exemplary data-capable strapband in medical-related activities.

FIG. 5D illustrates representative data types for use with an exemplary data-capable strapband in medical-related activities. Here, hand 539 may also be configured for medical purposes and related-types of data such as heart rate monitoring data 560, respiratory monitoring data 562, body temperature data 564, blood sugar data 566, chemical protein/analysis data 568, patient medical records data 570, and healthcare professional (e.g., doctor, physician, registered nurse, physician's assistant, dentist, orthopedist, surgeon, and others) data 572. In some examples, data may be captured by band 539 directly from wear by a user. For example, band 539 may be able to sample and analyze sweat through a salinity or moisture detector to identify whether any particular chemicals, proteins, hormones, or other organic or inorganic compounds are present, which can be analyzed by band 539 or communicated to server 114 to perform further analysis. If sent to server 114, further analyses may be performed by a hospital or other medical facility using data captured by band 539. In other examples, more, fewer, or different types of data may be captured for medical-related activities.

Figure 5E:
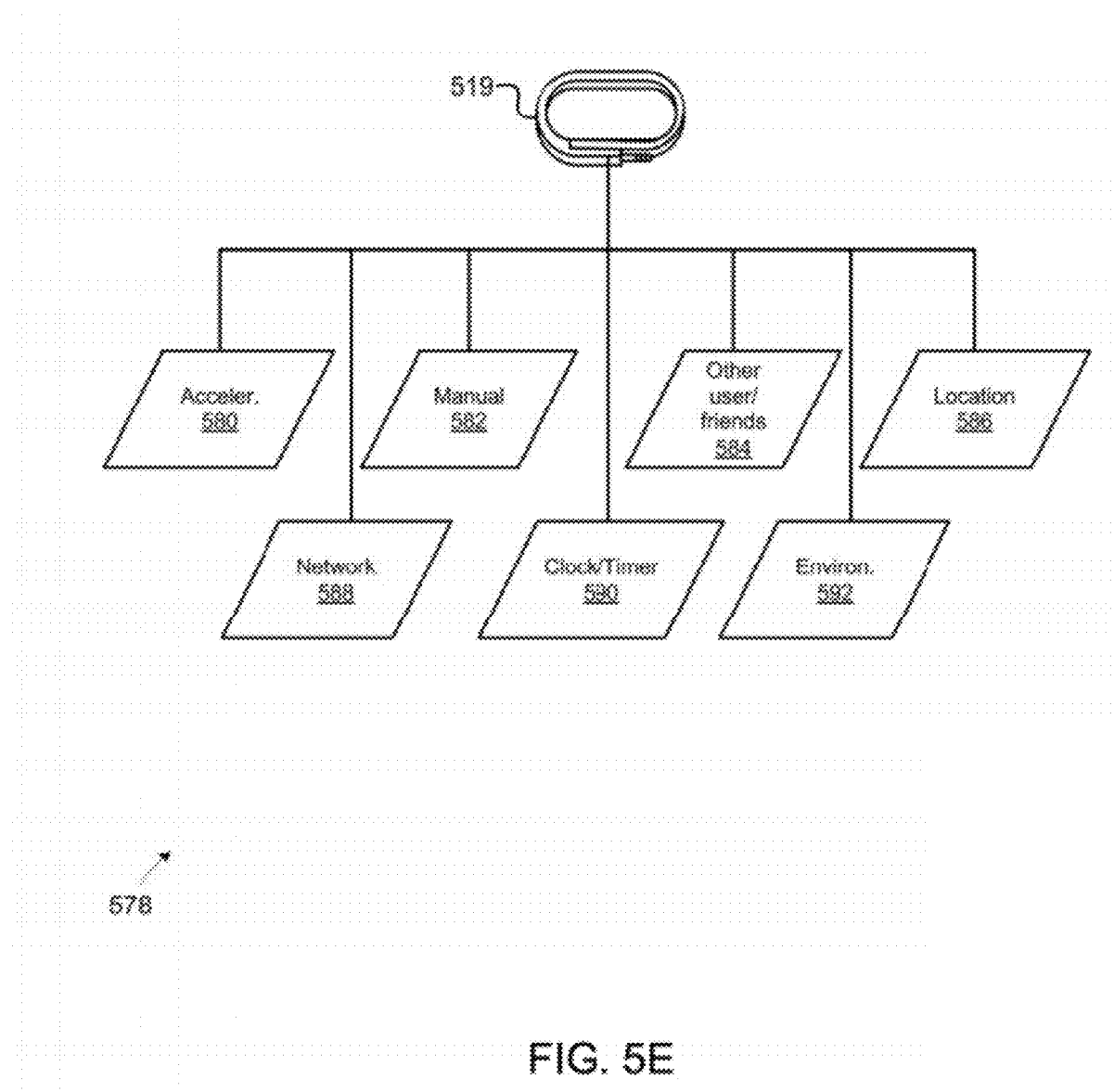
FIG. 5E illustrates representative data types for use with an exemplary data-capable strapband in social media/networking-related activities.

FIG. 5E illustrates representative data types for use with an exemplary data-capable strapband in social media/networking-related activities. Examples of social media/networking-related activities include related to Internet-based Social Networking Services ("SNS"), such as Facebook®, Twitter®, etc. Here, band 519, shown with an audio data plug, may be configured to capture data for use with various types of social media and networking-related services, websites, and activities. Accelerometer data 580, manual data 582, other user/friends data 584, location data 586, network data 588, clock/timer data 590, and environmental data 592 are examples of data that may be gathered and shared by, for example, uploading data from band 519 using, for example, an audio plug such as those described herein. As another example, accelerometer data 580 may be captured and shared with other users to share motion, activity, or other movement-oriented data. Manual data 582 may be data that a given user also wishes to share with other users. Likewise, other user/friends data 584 may be from other bands (not shown) that can be shared or aggregated with data captured by band 519. Location data 586 for band 519 may also be shared with other users. In other examples, a user may also enter manual data 582 to prevent other users or friends from receiving updated location data from band 519. Additionally, network data 588 and clock/timer data may be captured and shared with other users to indicate, for example, activities or events that a given user (i.e., wearing band 519) was engaged at certain locations. Further, if a user of band 519 has friends who are not geographically located in close or near proximity (e.g., the user of band 519 is located in San Francisco and her friend is located in Rome), environmental data can be captured by band 519 (e.g., weather, temperature, humidity, sunny or overcast (as interpreted from data captured by a light sensor and combined with captured data for humidity and temperature), among others). In other examples, more, fewer, or different types of data may be captured for medical-related activities.

Figure 6:
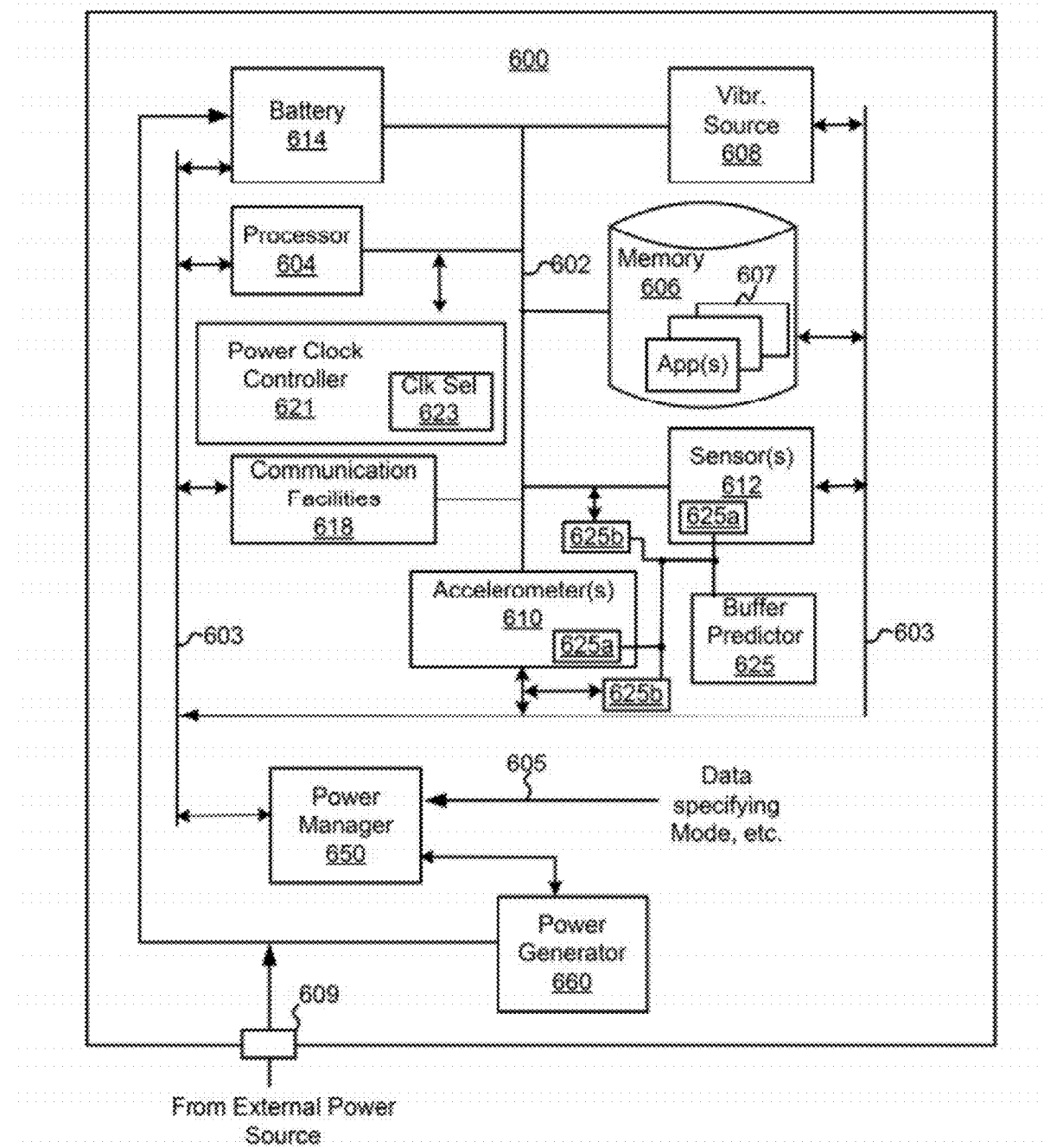
FIG. 6 illustrates a band configured to manage power in accordance with various embodiments.

FIG. 6 illustrates a strapband configured to manage power in accordance with various embodiments. As shown, FIG. 6 depicts a strapband 600 including one or more of the following: a processor 604, a memory 606, a vibration source 608, one or more accelerometers 610, one or more sensors 612 and one or more communication facilities 618, or any other equivalent variant or component. Strapband 600 also includes a power manager 650 and a power generator 660, which can reside in-situ or within an interior of strapband 600. Power manager 650 is coupled via paths 603 to processor 604, memory 606, vibration source 608, one or more accelerometers 610, one or more sensors 612 and one or more communication facilities 618, and is configured to monitor, for example, power output from energy storage devices, such as battery 614, and power consumed by processor 604, memory 606, vibration source 608, one or more accelerometers 610, one or more sensors 612 and one or more communication facilities 618. Communication facilities 618 are configured to either receive or transmit data, or both, in accordance with various communication protocols and infrastructures. Further, power manager 650 can be configured to operate one or more components, including processor 604, memory 606, vibration source 608, one or more accelerometers 610, one or more sensors 612, battery 614, and one or more communication facilities 618 as a function of, for example, of one or more of the following: the power consumption of a component (e.g., when a component exceeds a threshold, the power to that component can be reduced or shut off), a mode of operation of strapband 600 (e.g., power manager 650 can modify power consumption based on whether strapband 600 is in a mode associated with a range of detected amounts of motion, such when a user is sleeping), an activity being performed (e.g., walking, sitting, running, swimming, jumping, etc.), a state of a user (e.g., based on user characteristics detected or derived from a subset of sensors 612), an environmental characteristic or factor in which the strapband is disposed (e.g., time of day, amount of light, etc.), and other like factors or parameters with which power management can be implemented.

Figure 17A:
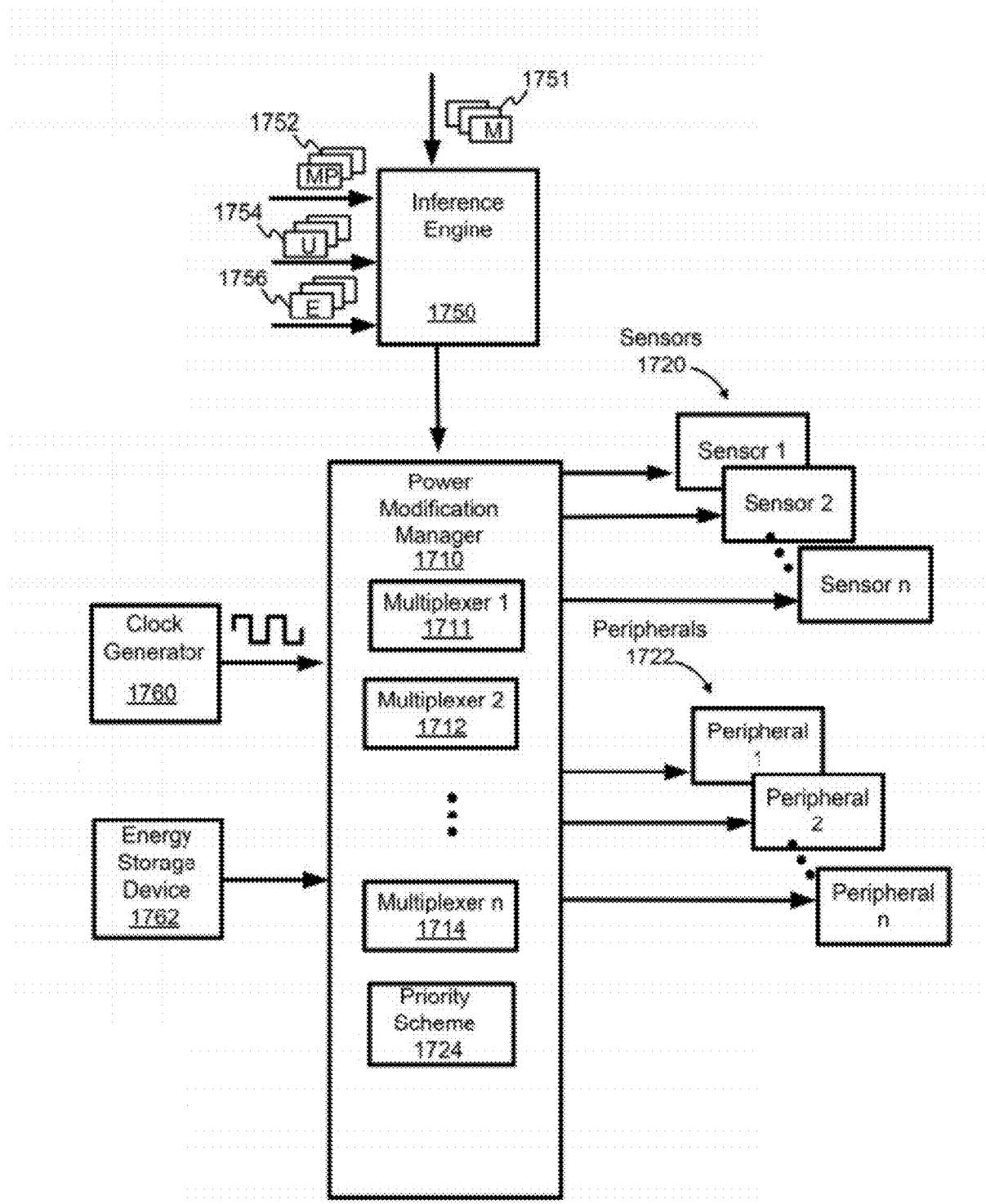
FIG. 17A depicts a power modification manager configured to modify the application of power to one or more components, according to some embodiments.

Also, power manager 650 can disable operation of components 604 to 618 in accordance with a priority scheme that seeks to prolong operation of strapband 600 at the expense of disabling lower priority functions and/or components. For example, when communication facilities 618 is of least importance, based on a priority scheme, communication facilities 618 may be disabled prior to other components with an aim to conserve power. FIG. 17A depicts an example of an implementation in which a power modification manager—or equivalent structure and/or array—can be used to optimize power distribution and related signals by selectively applying power signals, clock signals, and/or other signals, according to some embodiments. As shown, power manager 650 is configured to receive data via path 605 to determine its functionality, thereby receiving data specifying mode, user state, etc. In some embodiments, power manager can modify the operation of one or more applications 607 stored as executable instructions in, for example, memory 606. For example, an application 607 can be prioritized to either be implemented or not implement relative to other applications as a function of one or more factors, such as the power currently stored in a battery, the activity or motion in which a user is engaged, the user's characteristics (e.g., based on biometric data and the like), environmental characteristics (e.g., ambient air temperature, pressure, etc.), communications received from other strapbands or other communication devices, and other like factors.

Power generator 660 is configured to source charge or power (in any suitable form) to an energy storage component for strapband 600, such as battery 614, regardless whether the power is generated internally or externally, or both. Power generator 660 can be an electro-mechanical device that converts motion of strapband 600 (e.g., along a path of motion) into electrical energy. For example, a solenoid can be used to convert motion of a mechanical part through a coil into electrical energy, which, in turn, can be used to charge battery 614. In some embodiments, power generator 660, or a portion thereof, can be disposed external to strapband 600. For example, power generator 660 can include a receiver configured to receive energy (e.g., radio frequency, or RF, energy) from an external source. Power also can also be applied via port 609 to battery 614, such as from an AC-to-DC power converter, or from a mobile computing device (e.g., a mobile communication device, such as a mobile/smart phone). Power generator 660 can include any structure and/or function that produce electricity to charge battery 614. As used herein, the term "power manager" can be used interchangeably with the term "power management module." A power manager can be implemented in hardware or software, or a combination thereof, collectively or distributed throughout or among a strapband structure.

FIG. 6 is a block diagram further depicting a structure of a strapband including a power clock controller 621 and a buffer predictor 625. According to some embodiments, power clock control 621 is configured to adapt a clock frequency and/or waveform shape to operate at least processor 604 sufficiently to process data generated by sensors and perform other functions for the activity a user is engaged (e.g., sleeping, walking, running, swimming, working, sitting, etc.) or mode of operation (e.g., sleep mode or other modes of associated with relatively low motion, active mode or other modes of associated with relatively high motion, etc.). Each activity and/or mode may use different combinations of sensors 612, accelerometers 610, and other components. As such, power clock controller 621 can modify one or more clock signals to place processor 604 in an optimally low power consumption state while operating sufficiently to, for example, process inputs from sensors 612 and other components. In one embodiments, power clock controller 621 can optionally include, or operate in with, a clock selector ("Clk Sel") 623, which is configured to select a clock or a characteristic of the clock (e.g., a clock frequency) with which the clock signal operates. Clock selector 623 is configured to determine a clock frequency to apply to processor 604 for servicing a specific "sensor load" based on data generated by selected sensors during any activity or mode. The term "sensor load" can refer to, at least in some embodiments, to an amount of data generated by a subset of sensors selected during an activity or mode at a certain rate. For example, the number of sensors 612 used during sleep mode can be fewer than used during an active mode, and, as such, sleep mode can have a lighter sensor load than during the active mode. Power clock controller 621 is configured to operate a clock at a rate sufficiently fast enough to service an amount of data, but sufficiently slow enough to conserve power that otherwise might be expended if processor 604 operates at the maximum clock rate. Clock selector 623 can also be configured to select which component or peripheral in strapband 600 can receive a modified clock signal.

Buffer predictor 625 is configured to dynamically size a buffer for receiving or transmitting sensor data as a function of whether a certain event is occurring or is likely to occur. In operation, buffer predictor 625 can size buffers 625a and/or 625b as a function of the rate at which one or more sensors are likely to generate sensor data for processing by processor 604. Buffers 625a represent buffers internal to components of strapband 600, such as internal to sensor(s) 612 and accelerometer(s) 610, and buffers 625b represent external to the components. By dynamically sizing a buffer 625a or buffer 625b, processor 604 need not operate (e.g., awake) or enter a higher-level of power consumptive activity and need not introduce latency as might be the case when the sizes of buffers 625a and 625b have static sizes. Static buffer sizes can include unused allocated memory locations that otherwise are processed. Buffers 625a and 625b can be implemented in any memory within strapband 600. Power clock controller 621 and/or buffer predictor 625 can be formed in power manger 650 or can be distributed in or about any other component in strapband 600. Note, too, that one or more components in strapband 600 can be implemented in software or hardware, or a combination thereof.

Figure 7A:
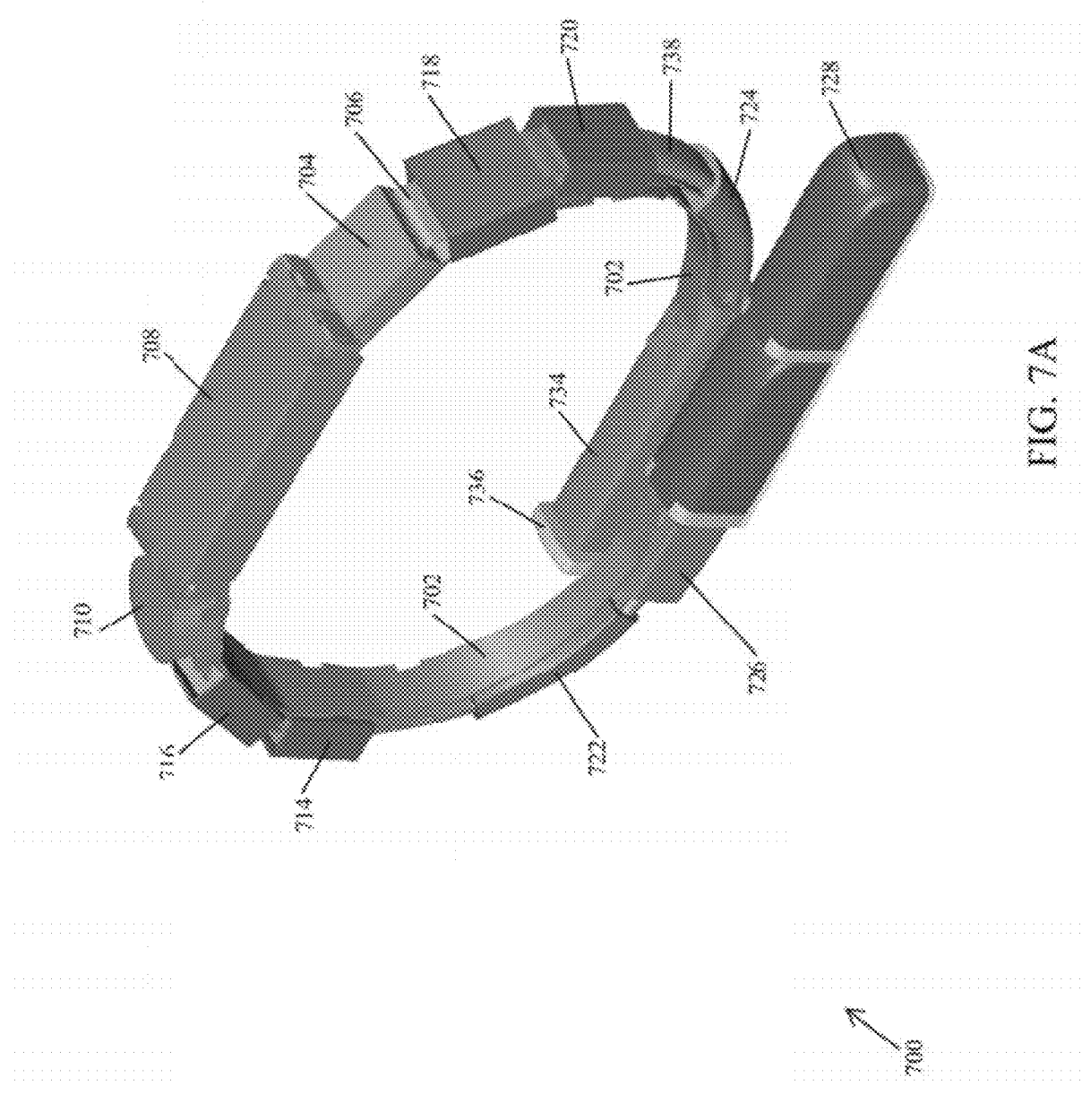
FIG. 7A illustrates a perspective view of an exemplary data-capable strapband.

FIG. 7A illustrates a perspective view of an exemplary data-capable strapband configured to receive overmolding. Here, band 700 includes framework 702, covering 704, flexible circuit 706, covering 708, motor 710, coverings 714-724, plug 726, accessory 728, control housing 734, control 736, and flexible circuits 737-738. In some examples, band 700 is shown with various elements (i.e., covering 704, flexible circuit 706, covering 708, motor 710, coverings 714-724, plug 726, accessory 728, control housing 734, control 736, and flexible circuits 737-738) coupled to framework 702. Coverings 708, 714-724 and control housing 734 may be configured to protect various types of elements, which may be electrical, electronic, mechanical, structural, or of another type, without limitation. For example, covering 708 may be used to protect a battery and power management module from protective material formed around band 700 during an injection molding operation. As another example, housing 704 may be used to protect a printed circuit board assembly ("PCBA") from similar damage. Further, control housing 734 may be used to protect various types of user interfaces (e.g., switches, buttons (e.g., control 736), lights, light-emitting diodes, or other control features and functionality) from damage. In other examples, the elements shown may be varied in quantity, type, manufacturer, specification, function, structure, or other aspects in order to provide data capture, communication, analysis, usage, and other capabilities to band 700, which may be worn by a user around a wrist, arm, leg, ankle, neck or other protrusion or aperture, without restriction. Band 700, in some examples, illustrates an initial unlayered device that may be protected using the techniques for protective overmolding as described above. Alternatively, the number, type, function, configuration, ornamental appearance, or other aspects shown may be varied without limitation.

FIG. 7B illustrates a side view of an exemplary data-capable strapband. Here, band 740 includes framework 702, covering 704, flexible circuit 706, covering 708, motor 710, battery 712, coverings 714-724, plug 726, accessory 728, button/switch/LED 730-732, control housing 734, control 736, and flexible circuits 737-738 and is shown as a side view of band 700. In other examples, the number, type, function, configuration, ornamental appearance, or other aspects shown may be varied without limitation.

FIG. 7C illustrates another side view of an exemplary data-capable strapband. Here, band 750 includes framework 702, covering 704, flexible circuit 706, covering 708, motor 710, battery 712, coverings 714-724, accessory 728, button/switch/LED 730-732, control housing 734, control 736, and flexible circuits 737-738 and is shown as an opposite side view of band 740. In some examples, button/switch/LED 730-732 may be implemented using different types of switches, including multiple position switches that may be manually turned to indicate a given function or command. Further, underlighting provided by light emitting diodes ("LED") or other types of low power lights or lighting systems may be used to provide a visual status for band 750. In other examples, the number, type, function, configuration, ornamental appearance, or other aspects shown may be varied without limitation.

FIG. 7D illustrates a top view of an exemplary data-capable strapband. Here, band 760 includes framework 702, coverings 714-716 and 722-724, plug 726, accessory 728, control housing 734, control 736, flexible circuits 737-738, and PCBA 762. In other examples, the number, type, function, configuration, ornamental appearance, or other aspects shown may be varied without limitation.

FIG. 7E illustrates a bottom view of an exemplary data-capable strapband. Here, band 770 includes framework 702, covering 704, flexible circuit 706, covering 708, motor 710, coverings 714-720, plug 726, accessory 728, control housing 734, control 736, and PCBA 772. In some examples, PCBA 772 may be implemented as any type of electrical or electronic circuit board element or component, without restriction. In other examples, the number, type, function, configuration, ornamental appearance, or other aspects shown may be varied without limitation.

FIG. 7F illustrates a front view of an exemplary data-capable strapband. Here, band 780 includes framework 702, flexible circuit 706, covering 708, motor 710, coverings 714-718 and 722, accessory 728, button/switch/LED 730, control housing 734, control 736, and flexible circuit 737. In other examples, the number, type, function, configuration, ornamental appearance, or other aspects shown may be varied without limitation.

FIG. 7G illustrates a rear view of an exemplary data-capable strapband. Here, band 790 includes framework 702, covering 708, motor 710, coverings 714-722, analog audio plug 726, accessory 728, control 736, and flexible circuit 737. In some examples, control 736 may be a button configured for depression in order to activate or initiate other functionality of band 790. In other examples, the number, type, function, configuration, ornamental appearance, or other aspects shown may be varied without limitation.

Figure 8A:
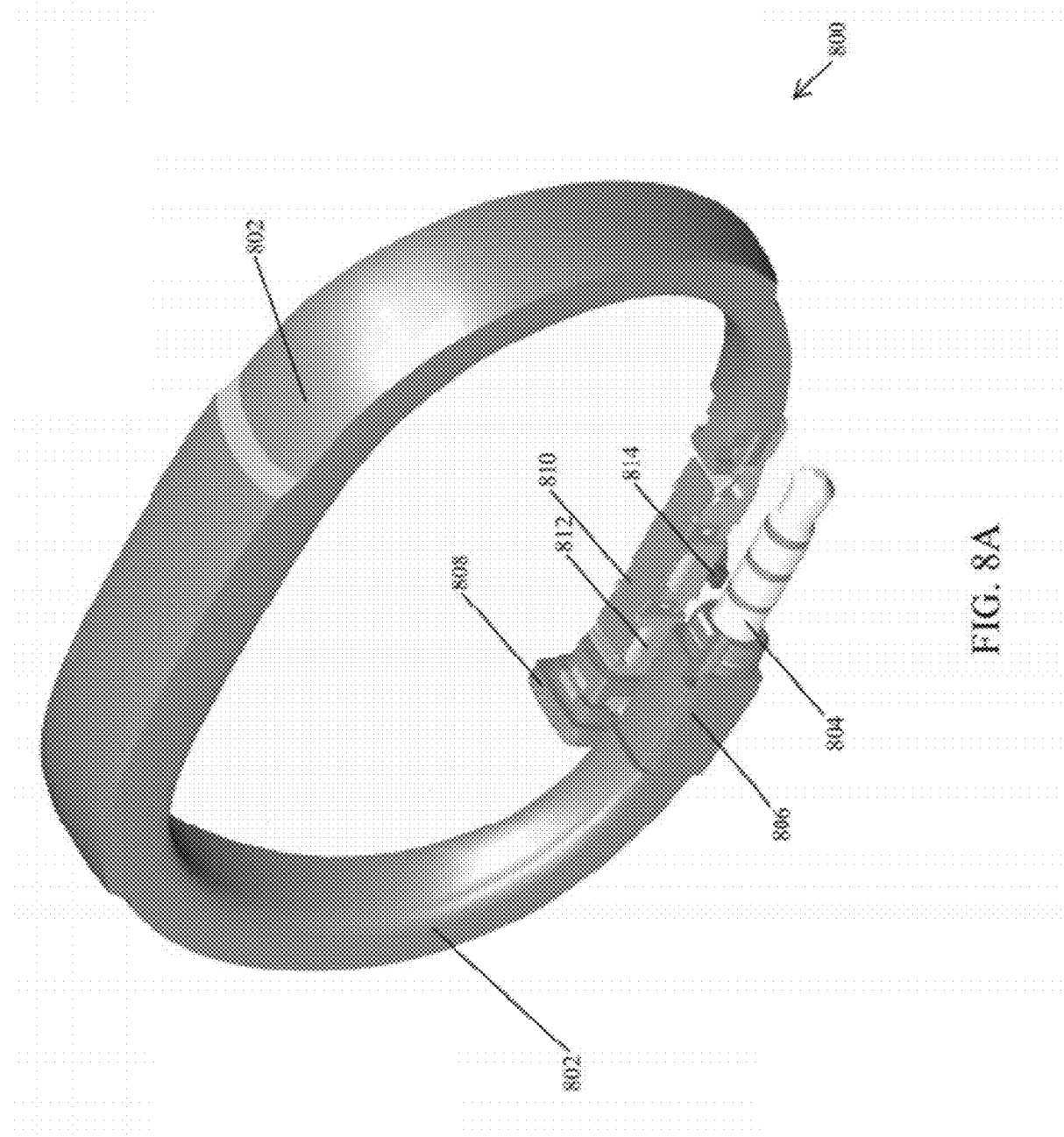
FIG. 8A illustrates a perspective view of an exemplary data-capable strapband.

FIG. 8A illustrates a perspective of an exemplary data-capable strapband having a first molding. Here, an alternative band (i.e., band 800) includes molding 802, analog audio TRRS-type plug (hereafter "plug") 804, plug housing 806, button 808, framework 810, control housing 812, and indicator light 814. In some examples, a first protective overmolding (i.e., molding 802) has been applied over band 700 (FIG. 7) and the above-described elements (e.g., covering 704, flexible circuit 706, covering 708, motor 710, coverings 714-724, plug 726, accessory 728, control housing 734, control 736, and flexible circuit 738) leaving some elements partially exposed (e.g., plug 804, plug housing 806, button 808, framework 810, control housing 812, and indicator light 814). However, internal PCBAs, flexible connectors, circuitry, and other sensitive elements have been protectively covered with a first or inner molding that can be configured to further protect band 800 from subsequent moldings formed over band 800 using the above-described techniques. In other examples, the type, configuration, location, shape, design, layout, or other aspects of band 800 may be varied and are not limited to those shown and described. For example, TRRS plug 804 may be removed if a wireless communication facility is instead attached to framework 810, thus having a transceiver, logic, and antenna instead being protected by molding 802. As another example, button 808 may be removed and replaced by another control mechanism (e.g., an accelerometer that provides motion data to a processor that, using firmware and/or an application, can identify and resolve different types of motion that band 800 is undergoing), thus enabling molding 802 to be extended more fully, if not completely, over band 800. In other examples, the number, type, function, configuration, ornamental appearance, or other aspects shown may be varied without limitation.

Figure 8B:
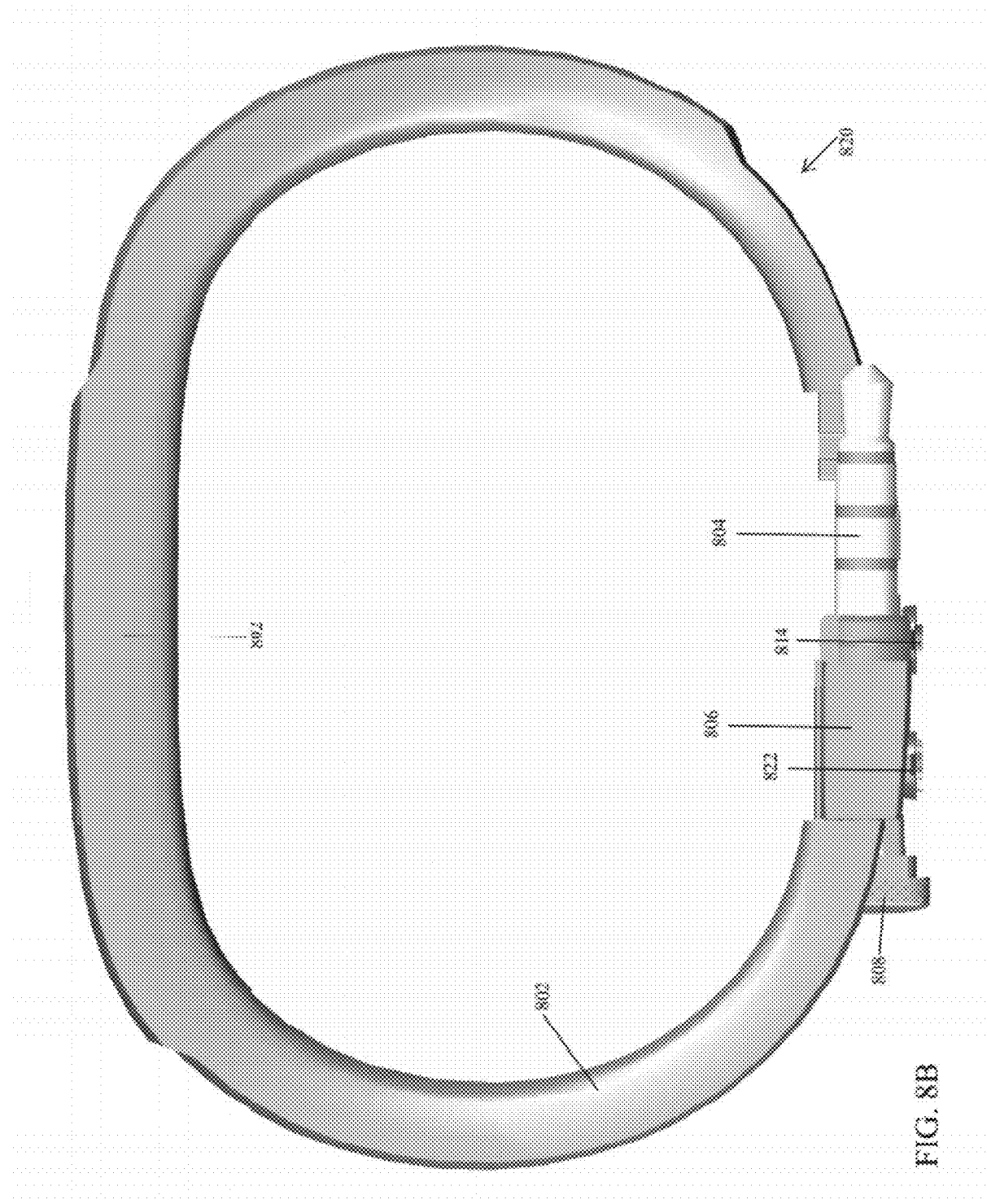
FIG. 8B illustrates a side view of an exemplary data-capable strapband.

FIG. 8B illustrates a side view of an exemplary data-capable strapband. Here, band 820 includes molding 802, plug 804, plug housing 806, button 808, control housing 812, and indicator lights 814 and 822. In other examples, the number, type, function, configuration, ornamental appearance, or other aspects shown may be varied without limitation.

Figure 8C:
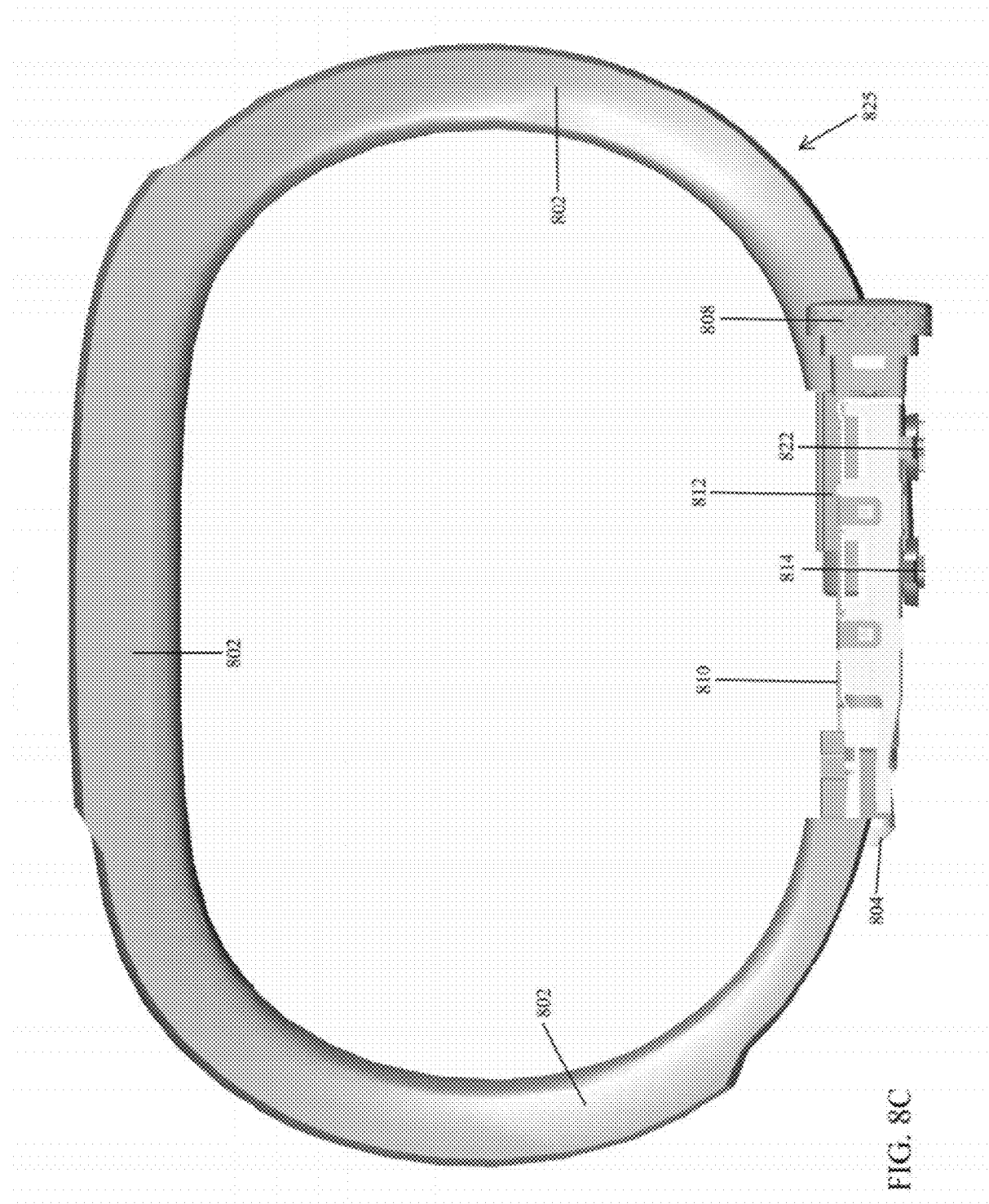
FIG. 8C illustrates another side view of an exemplary data-capable strapband.

FIG. 8C illustrates another side view of an exemplary data-capable strapband. Here, band 825 includes molding 802, plug 804, button 808, framework 810, control housing 812, and indicator lights 814 and 822. The view shown is an opposite view of that presented in FIG. 8B. In other examples, the number, type, function, configuration, ornamental appearance, or other aspects shown may be varied without limitation.

FIG. 8D illustrates a top view of an exemplary data-capable strapband. Here, band 830 includes molding 802, plug 804, plug housing 806, button 808, control housing 812, and indicator lights 814 and 822. In other examples, the number, type, function, configuration, ornamental appearance, or other aspects shown may be varied without limitation.

Figure 8E:
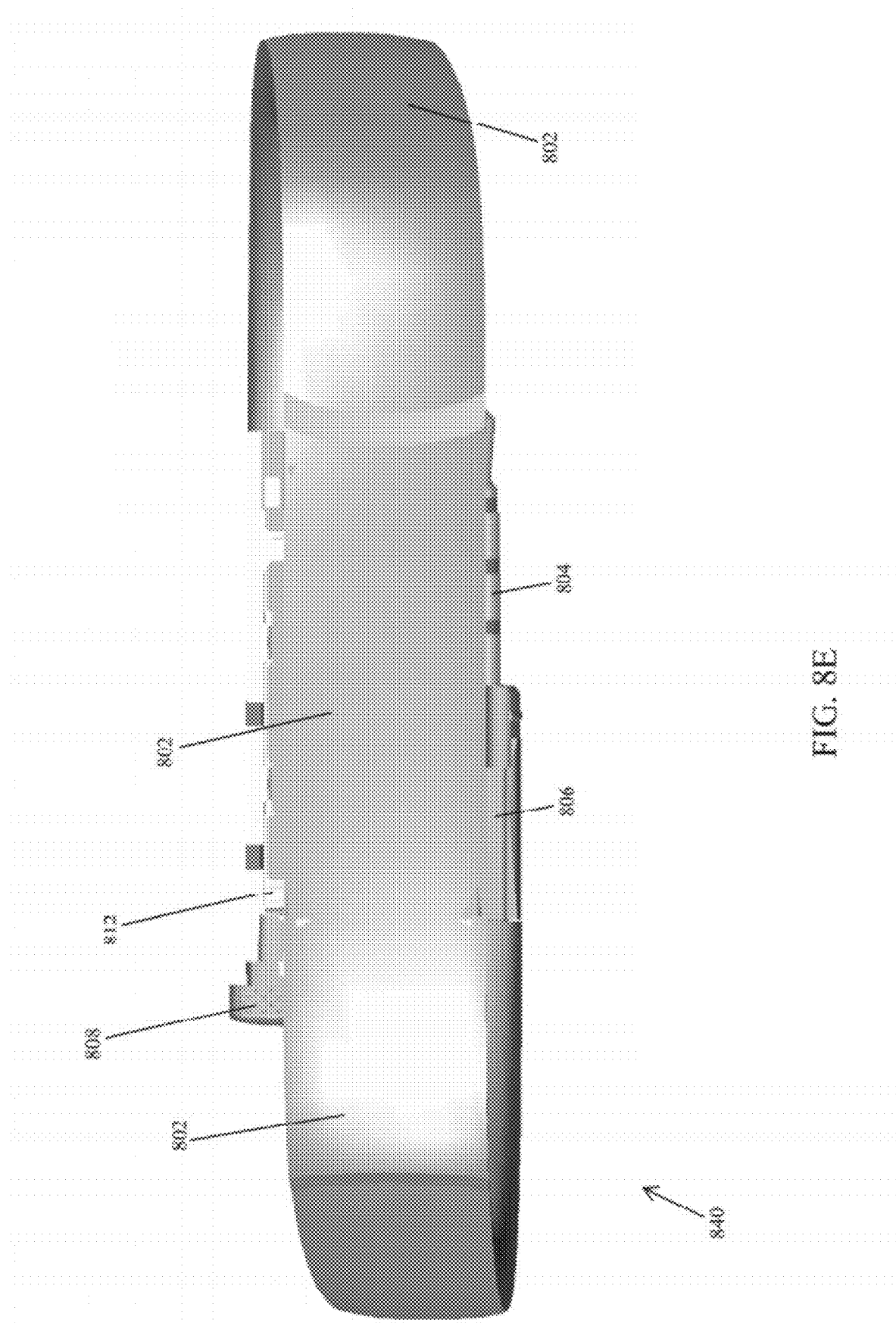
FIG. 8E illustrates a bottom view of an exemplary data-capable strapband.

FIG. 8E illustrates a bottom view of an exemplary data-capable strapband. Here, band 840 includes molding 802, plug 804, plug housing 806, button 808, control housing 812, and indicator lights 814 and 822. In other examples, the number, type, function, configuration, ornamental appearance, or other aspects shown may be varied without limitation.

FIG. 8F illustrates a front view of an exemplary data-capable strapband. Here, band 850 includes molding 802, plug 804, plug housing 806, button 808, control housing 812, and indicator light 814. In other examples, the number, type, function, configuration, ornamental appearance, or other aspects shown may be varied without limitation.

Figure 8G:
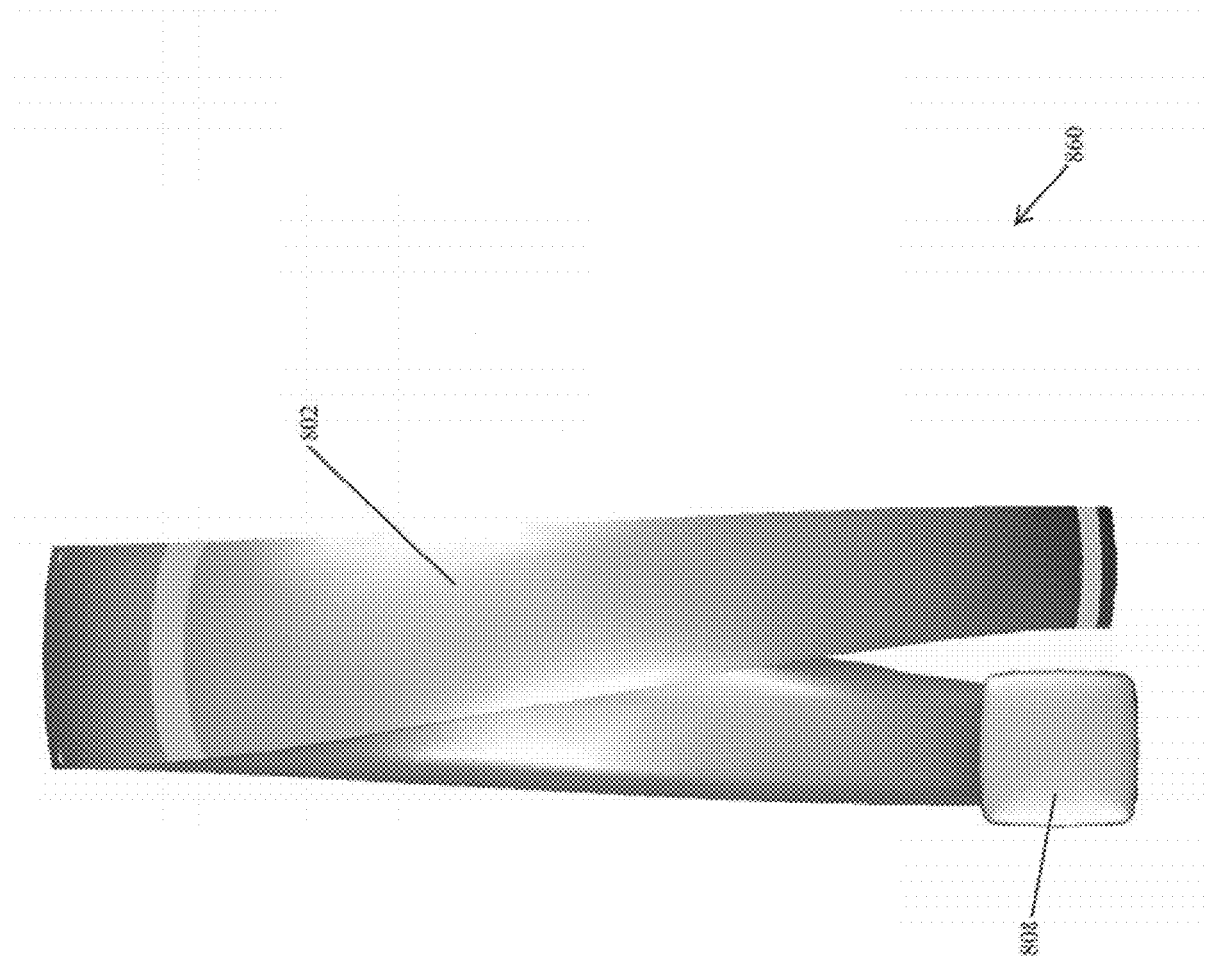
FIG. 8G illustrates a rear view of an exemplary data-capable strapband.

FIG. 8G illustrates a rear view of an exemplary data-capable strapband. Here, band 860 includes molding 802 and button 808. In other examples, the number, type, function, configuration, ornamental appearance, or other aspects shown may be varied without limitation.

Figure 9A:
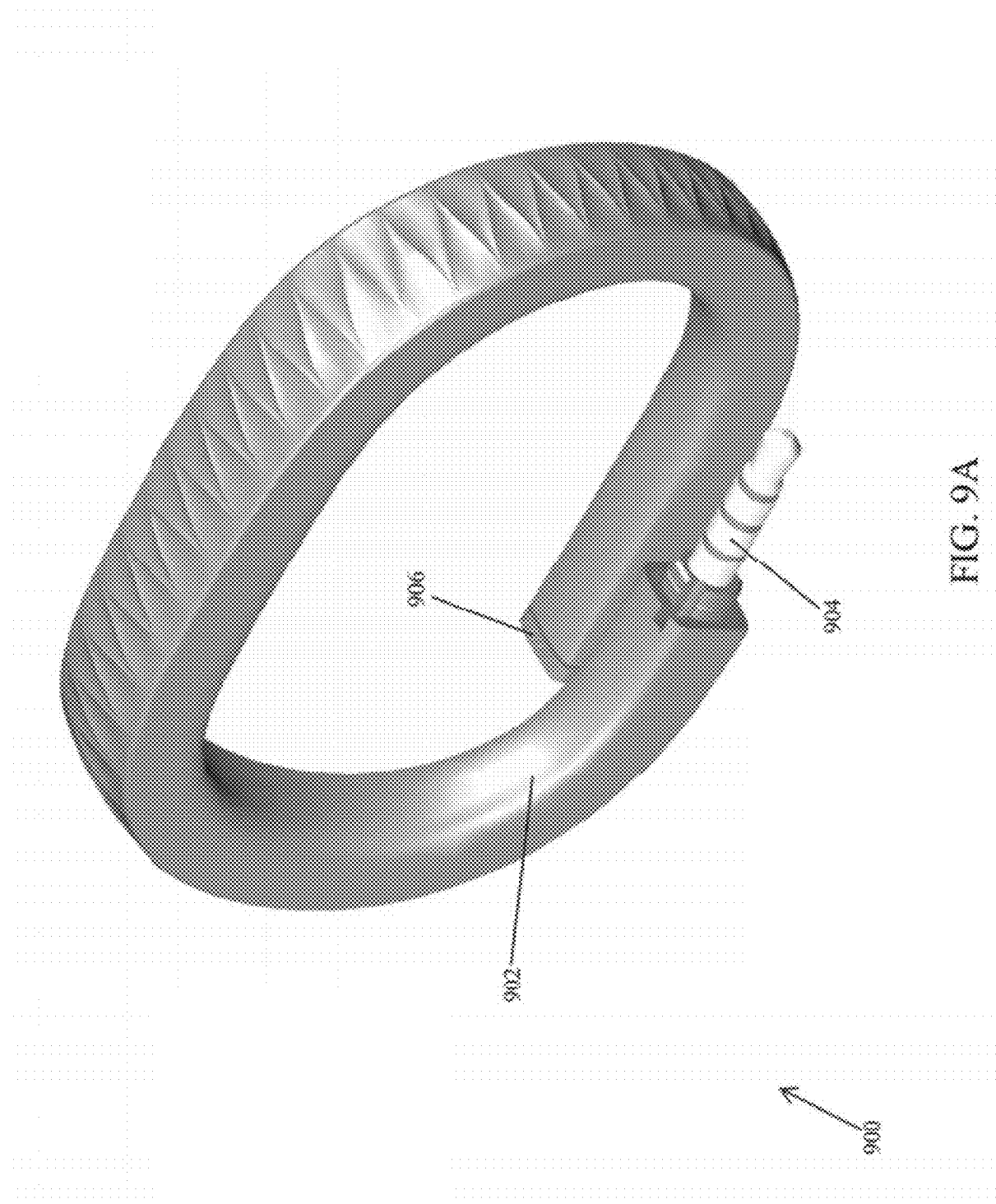
FIG. 9A illustrates a perspective view of an exemplary data-capable strapband.

FIG. 9A illustrates a perspective view of an exemplary data-capable strapband having a second molding. Here, band 900 includes molding 902, plug 904, and button 906. As shown another overmolding or protective material has been formed by injection molding, for example, molding 902 over band 900. As another molding or covering layer, molding 902 may also be configured to receive surface designs, raised textures, or patterns, which may be used to add to the commercial appeal of band 900. In some examples, band 900 may be illustrative of a finished data-capable strapband (i.e., band 700 (FIG. 7), 800 (FIG. 8) or 900) that may be configured to provide a wide range of electrical, electronic, mechanical, structural, photonic, or other capabilities.

Here, band 900 may be configured to perform data communication with one or more other data-capable devices (e.g., other bands, computers, networked computers, clients, servers, peers, and the like) using wired or wireless features. For example, plug 900 may be used, in connection with firmware and software that allow for the transmission of audio tones to send or receive encoded data, which may be performed using a variety of encoded waveforms and protocols, without limitation. In other examples, plug 904 may be removed and instead replaced with a wireless communication facility that is protected by molding 902. If using a wireless communication facility and protocol, band 900 may communicate with other data-capable devices such as cell phones, smart phones, computers (e.g., desktop, laptop, notebook, tablet, and the like), computing networks and clouds, and other types of data-capable devices, without limitation. In still other examples, band 900 and the elements described above in connection with FIGS. 1-9, may be varied in type, configuration, function, structure, or other aspects, without limitation to any of the examples shown and described.

FIG. 9B illustrates a side view of an exemplary data-capable strapband. Here, band 910 includes molding 902, plug 904, and button 906. In other examples, the number, type, function, configuration, ornamental appearance, or other aspects shown may be varied without limitation.

Figure 9C:
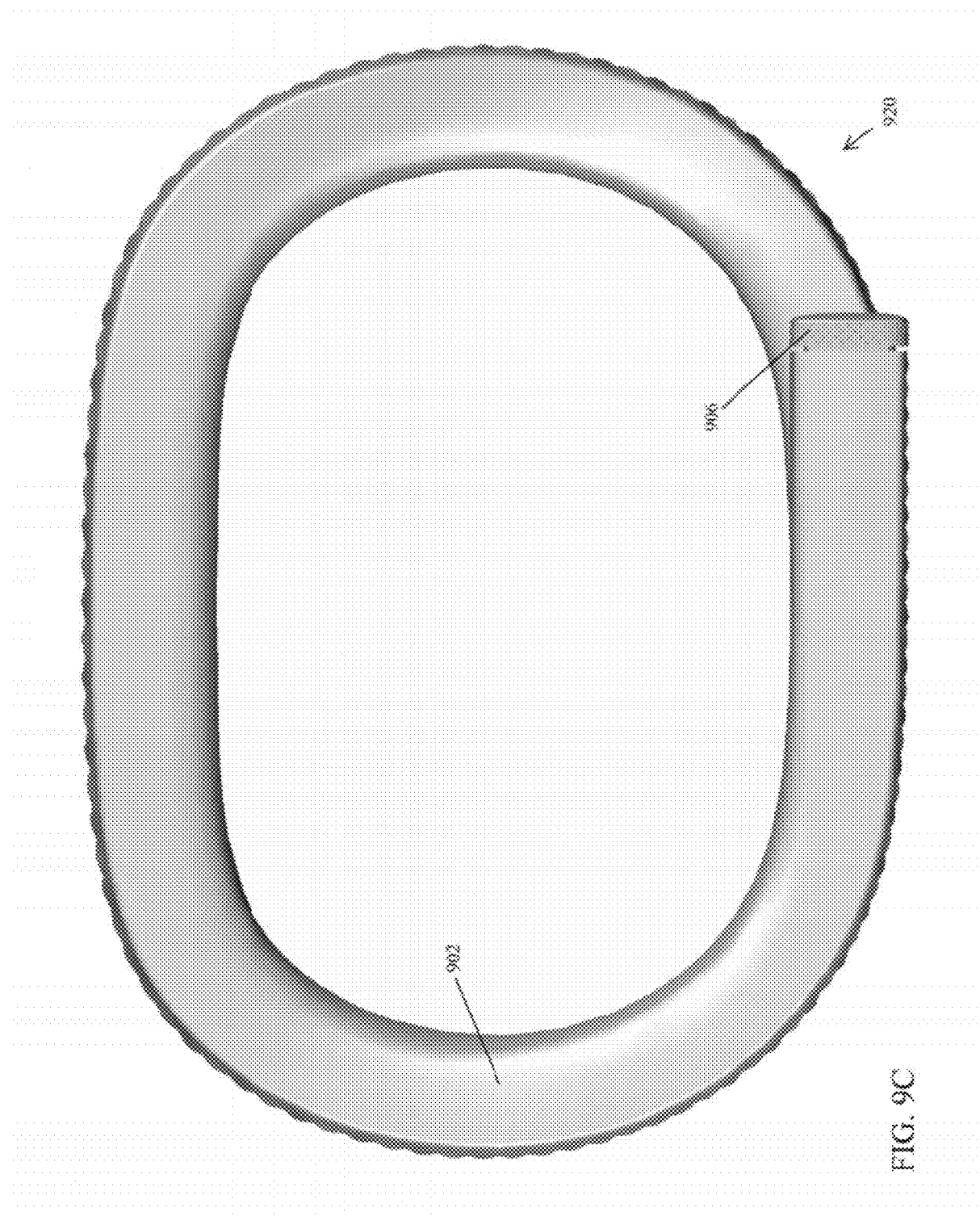
FIG. 9C illustrates another side view of an exemplary data-capable strapband.

FIG. 9C illustrates another side view of an exemplary data-capable strapband. Here, band 920 includes molding 902 and button 906. In other examples, the number, type, function, configuration, ornamental appearance, or other aspects shown may be varied without limitation.

Figure 9D:
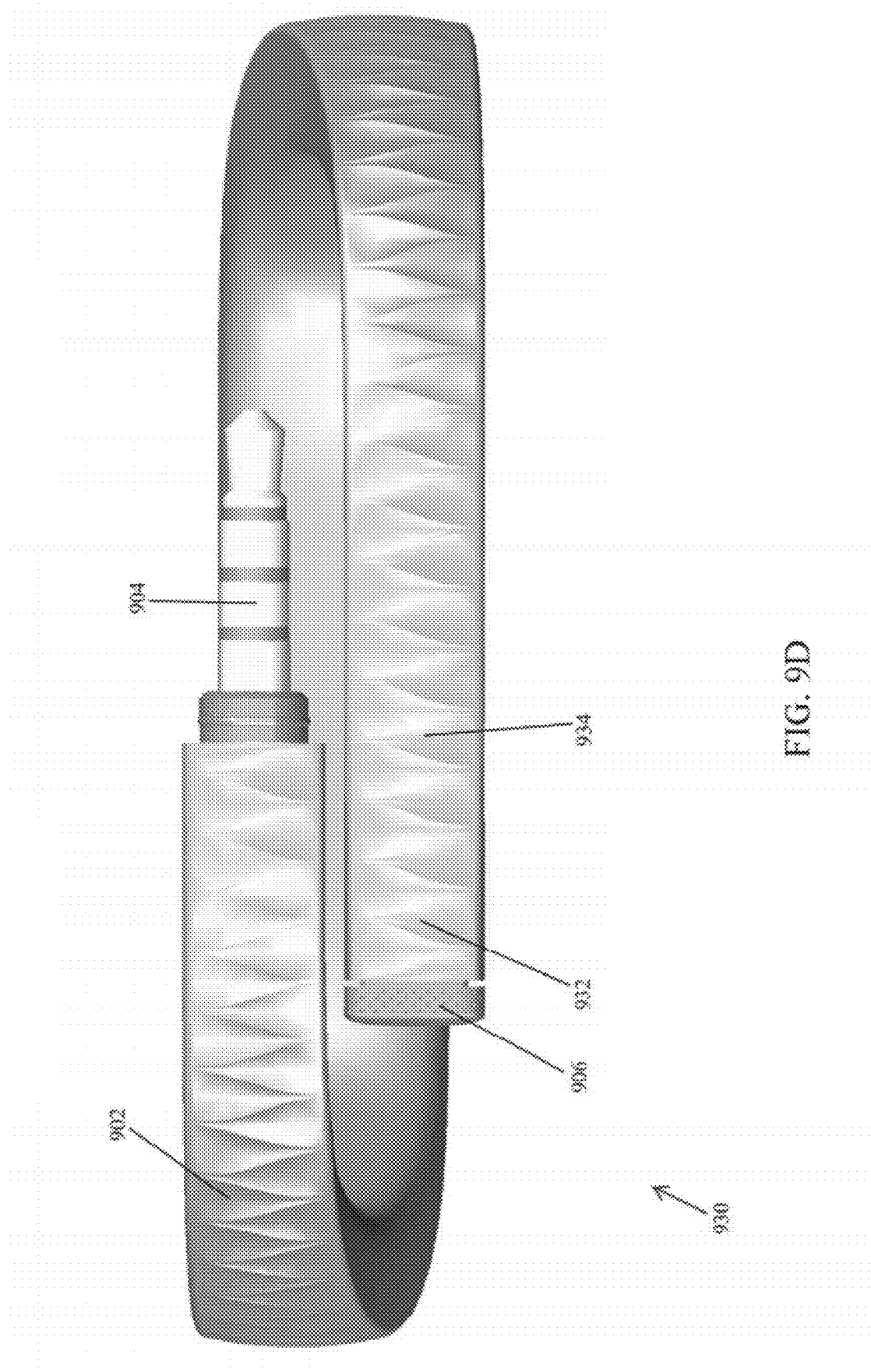
FIG. 9D illustrates a top view of an exemplary data-capable strapband.

FIG. 9D illustrates a top view of an exemplary data-capable strapband. Here, band 930 includes molding 902, plug 904, button 906, and textures 932-934. In some examples, textures 932-934 may be applied to the external surface of molding 902. As an example, textured surfaces may be molded into the exterior surface of molding 902 to aid with handling or to provide ornamental or aesthetic designs. The type, shape, and repetitive nature of textures 932-934 are not limiting and designs may be either two or three-dimensional relative to the planar surface of molding 902. In other examples, the number, type, function, configuration, ornamental appearance, or other aspects shown may be varied without limitation.

Figure 9E:
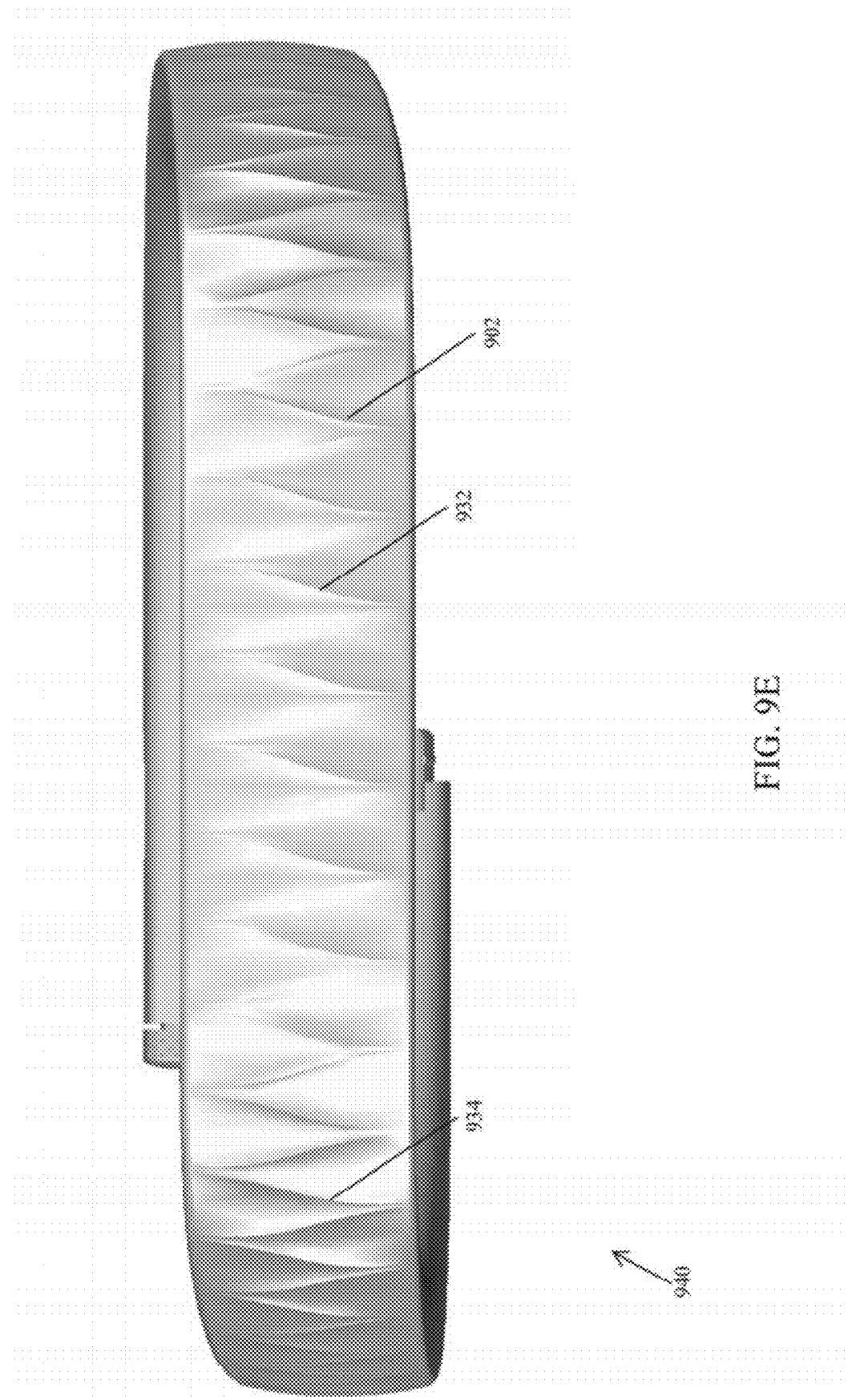
FIG. 9E illustrates a bottom view of an exemplary data-capable strapband.

FIG. 9E illustrates a bottom view of an exemplary data-capable strapband. Here, band 940 includes molding 902 and textures 932-934, as described above. In other examples, the number, type, function, configuration, ornamental appearance, or other aspects shown may be varied without limitation.

Figure 9F:
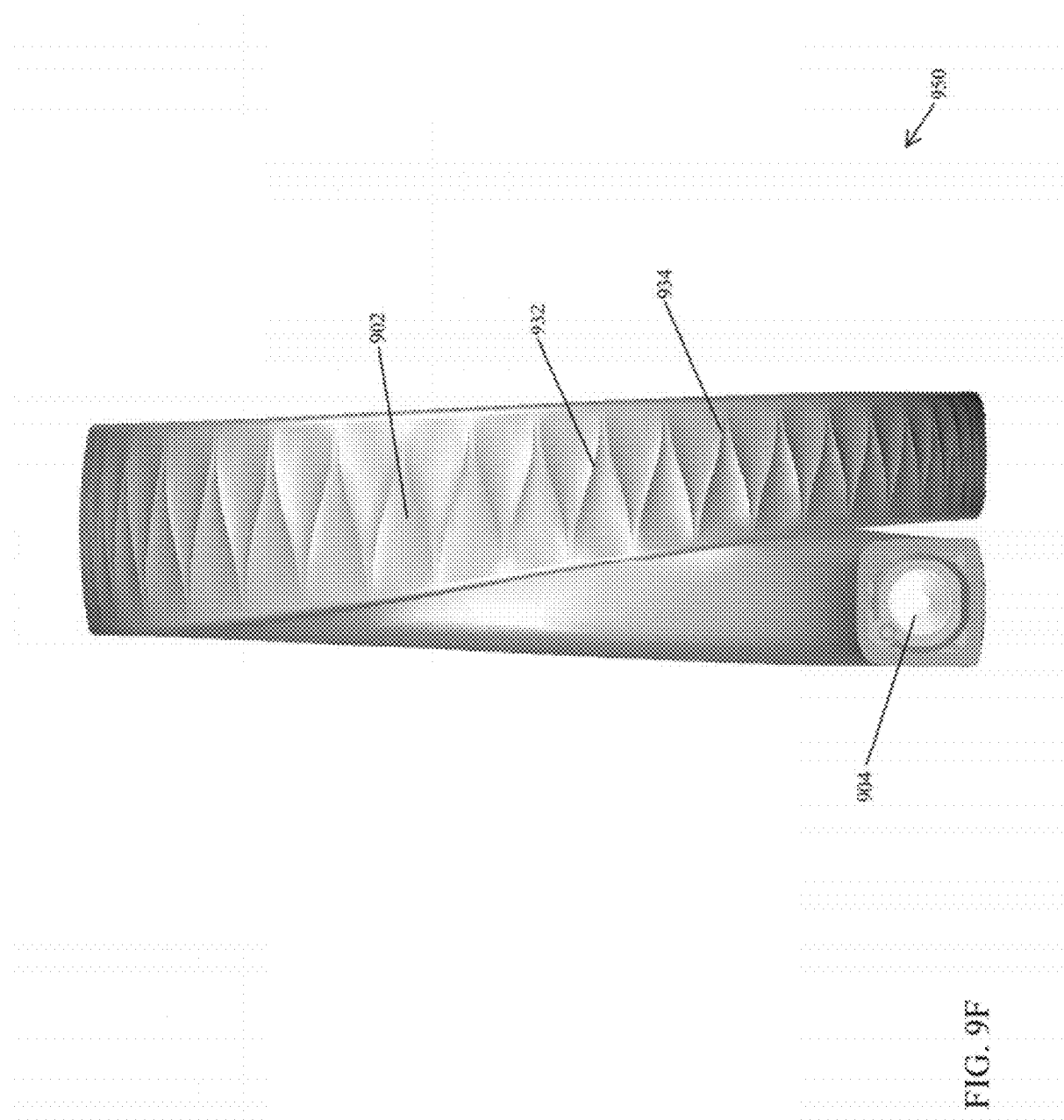
FIG. 9F illustrates a front view of an exemplary data-capable strapband.

FIG. 9F illustrates a front view of an exemplary data-capable strapband. Here, band 950 includes molding 902, plug 904, and textures 932-934. In other examples, the number, type, function, configuration, ornamental appearance, or other aspects shown may be varied without limitation.

Figure 9G:
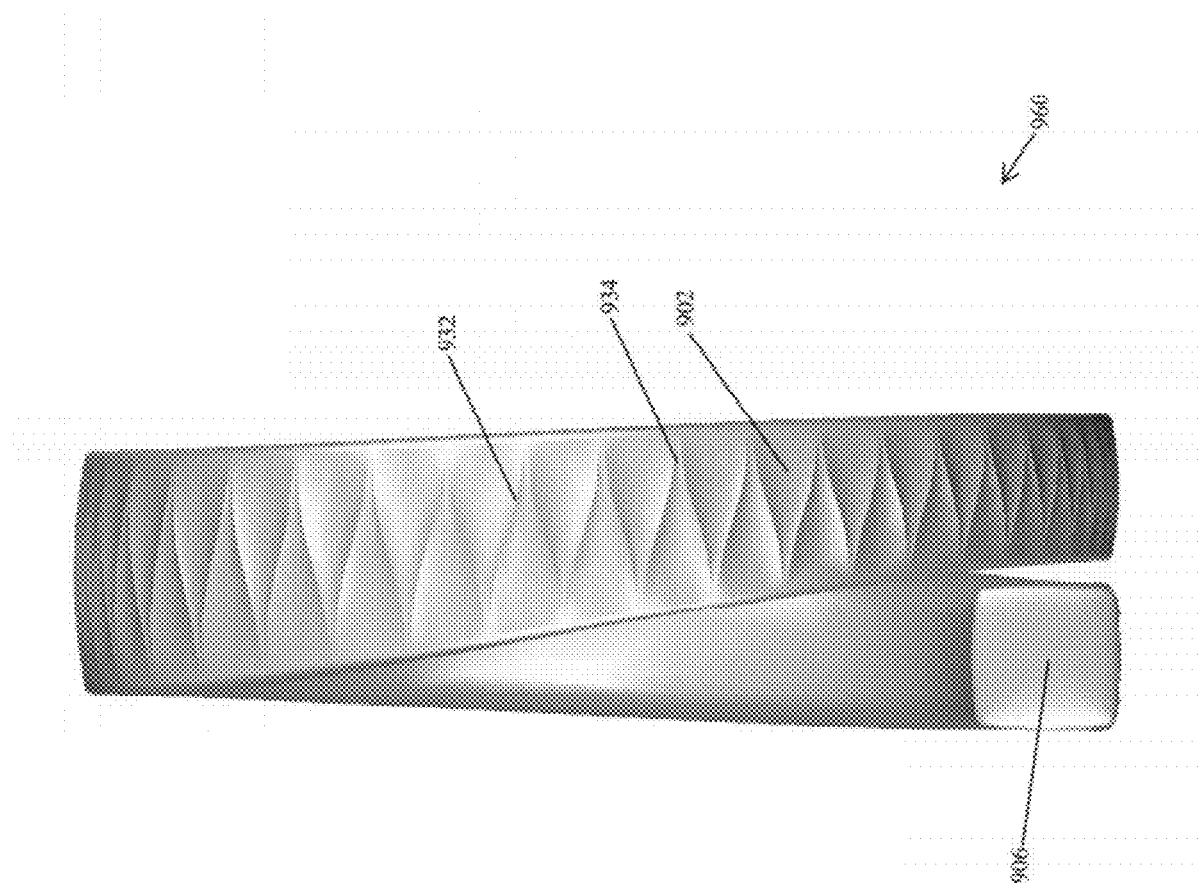
FIG. 9G illustrates a rear view of an exemplary data-capable strapband.

FIG. 9G illustrates a rear view of an exemplary data-capable strapband. Here, band 960 includes molding 902, button 906, and textures 932-934. In other examples, the number, type, function, configuration, ornamental appearance, or other aspects shown may be varied without limitation.

Figure 10:
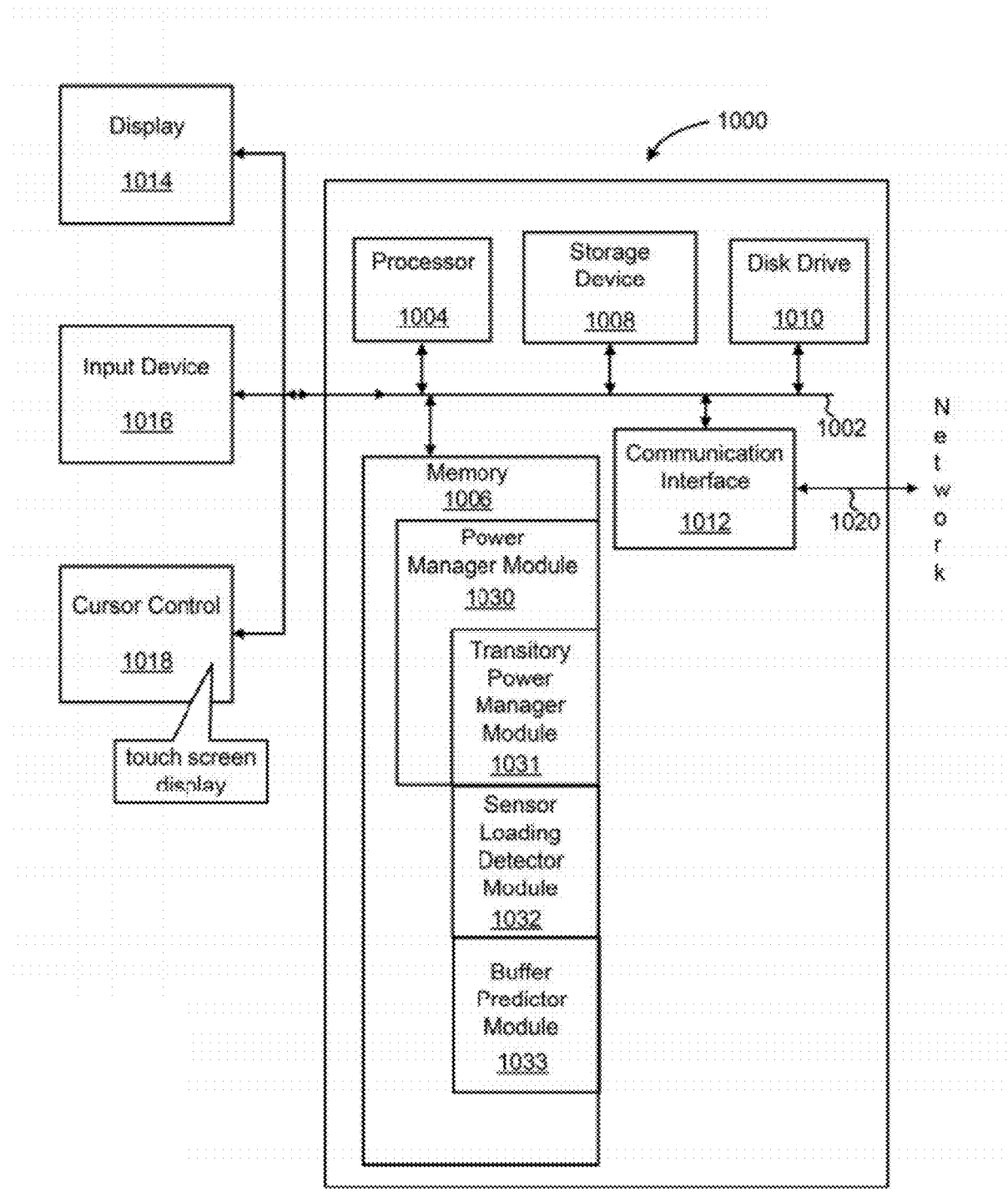
FIG. 10 illustrates an exemplary computer system suitable liar use with a data-capable strapband.

FIG. 10 illustrates an exemplary computer system suitable for use with a data-capable strapband. In some examples, computer system 1000 may be used to implement computer programs, applications, methods, processes, or other software to perform the above-described techniques. Computer system 1000 includes a bus 1002 or other communication mechanism for communicating information, which interconnects subsystems and devices, such as processor 1004, system memory 1006 (e.g., RAM), storage device 1008 (e.g., ROM), disk drive 1010 (e.g., magnetic or optical), communication interface 1012 (e.g., modem or Ethernet card), display 1014 (e.g., CRT or LCD), input device 1016 (e.g., keyboard), and cursor control 1018 (e.g., mouse or trackball).

According to some examples, computer system 1000 performs specific operations by processor 1004 executing one or more sequences of one or more instructions stored in system memory 1006. Such instructions may be read into system memory 1006 from another computer readable medium, such as static storage device 1008 or disk drive 1010. In some examples, hard-wired circuitry may be used in place of or in combination with software instructions for implementation.

The term "computer readable medium" refers to any tangible medium that participates in providing instructions to processor 1004 for execution. Such a medium may take many forms, including but not limited to, non-volatile media and volatile media. Non-volatile media includes, for example, optical or magnetic disks, such as disk drive 1010. Volatile media includes dynamic memory, such as system memory 1006.

Common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer can read.

Instructions may further be transmitted or received using a transmission medium. The term "transmission medium" may include any tangible or intangible medium that is capable of storing, encoding or carrying instructions for execution by the machine, and includes digital or analog communications signals or other intangible medium to facilitate communication of such instructions. Transmission media includes coaxial cables, copper wire, and fiber optics, including wires that comprise bus 1002 for transmitting a computer data signal.

In some examples, execution of the sequences of instructions may be performed by a single computer system 1000. According to some examples, two or more computer systems 1000 coupled by communication link 1020 (e.g., LAN, PSTN, or wireless network) may perform the sequence of instructions in coordination with one another. Computer system 1000 may transmit and receive messages, data, and instructions, including program, i.e., application code, through communication link 1020 and communication interface 1012. Received program code may be executed by processor 1004 as it is received, and/or stored in disk drive 1010, or other non-volatile storage for later execution.

In the example shown, system memory 1006 can include various modules that include executable instructions to implement functionalities described herein. In the example shown, system memory 1006 includes a power management module 1030, which can include a transistor power management module 1031. According to some embodiments, power management module 1030 and transistor power management module 1031 are described herein as examples of a power manager and a transistor power manager. According to some embodiments, system memory 1006 can also include a sensor loading detection module 1032 and a buffer predictor module 1033 are examples of a sensor loading detector and a buffer predictor as are described herein.

Figure 11:
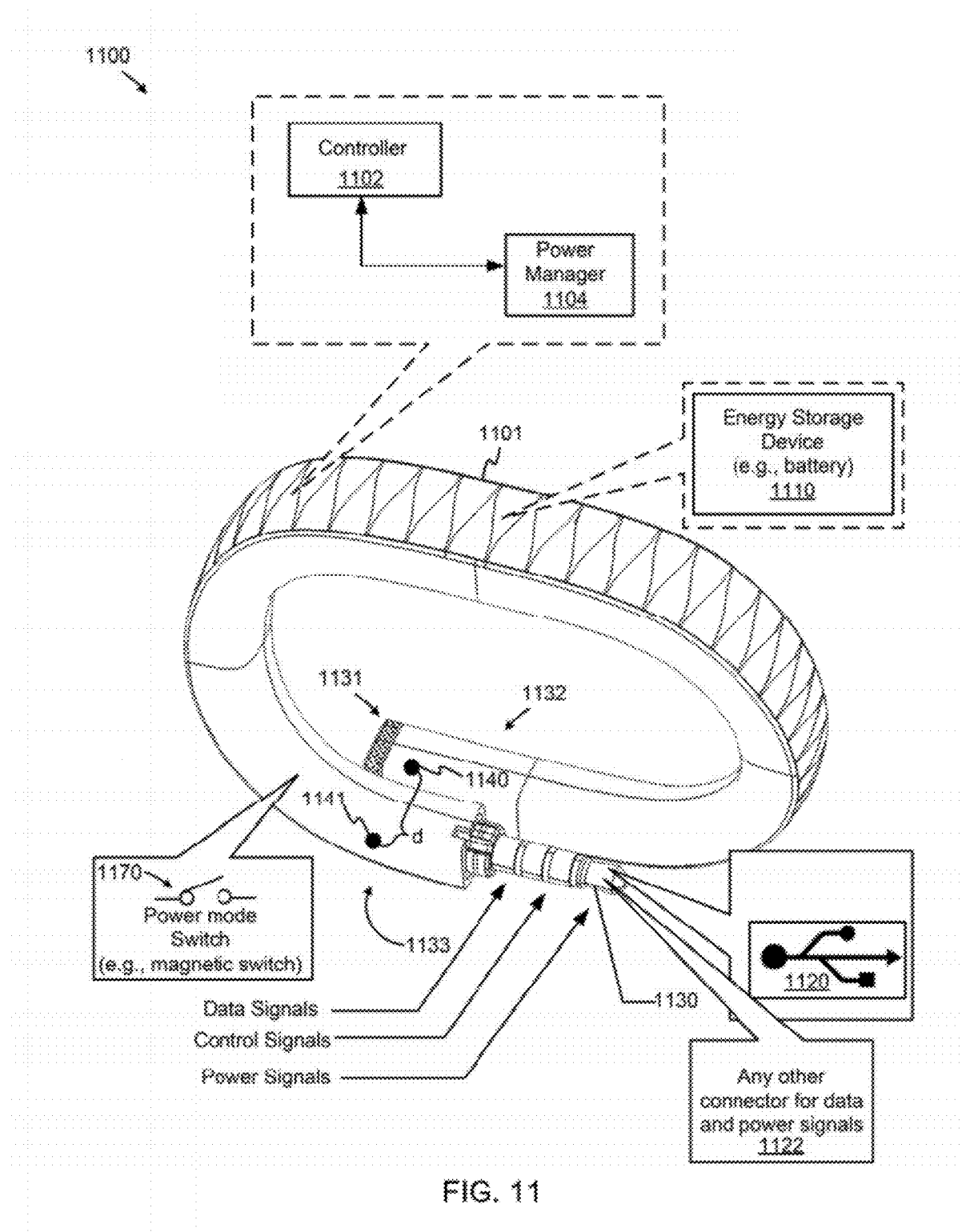
FIG. 11 depicts a power manager in a specific example of a strapband, such as a data-capable strapband, according to various embodiments.

FIG. 11 depicts a power manager in a specific example of a strapband, such as a data-capable strapband, according to various embodiments. In diagram 1100, strapband 1101 includes a controller 1102, a power manager 1104 and an energy storage device 1110, such as a battery, two or more of which are coupled to each other. Controller 1102 includes logic for controlling operation of at least some aspects of strapband 1101, and can be implemented as a processor, such as processor 604 of FIG. 6, a CPU, or the like. Further, strapband 1101 includes an example of a power port to provide at least power signals to the interior of strapband 1101 and/or to energy storage device 1110 for purposes of charging energy storage device 1110. In the example shown, the power port can be a connector 1130 (or a portion thereof). Connector 1130 also can be configured to facilitate the exchange of data and control signals between the exterior and the interior of strapband 1101. Connector 1130 can be, for example, a tip, ring, ring, sleeve ("TRRS") connector or the like (e.g., with 3 or more conductors to carry at least 3 or more signals). Connector 1130 can be configured to communicate analog signals, such as analog audio signals. In other examples, connector 1130 can be any type of connector 1122 that is suitable to exchange data, control, and/or power signals with, for example, controller 1102. In one instance, connector 1130 can be a universal serial bus ("USB")-compliant connector 1120, such as a four terminal USB® connector. Examples of connector 1120 include a mini USB connector and a micro USB connector. Note that in some embodiments, connector 1130 is configured to convey audio-encoded data and control signals (e.g., encoded in audio waveforms). Therefore, communications to controller 1102 can be via data and control signals encoded in analog signals. Note that power manager 1104 can be implemented in or as part of controller 1102. Or power manager 1104 can be implemented as executable instructions that can be executed by controller 1102.

In some embodiments, strapband 1101 can include a power mode switch 1170 configured to transition strapband 1101 between two or more power modes, which are described below, for example, in relation to FIGS. 12A, 12B and 13. Power mode switch 1170 is configured to be set in a first state (e.g., set during a test mode or prior to shipping) in which negligible or no power is being consumed. Power mode switch 1170 is configured further to be set in a second state whereby one or more (or all) components in strapband 1101 are configured to receive current from energy storage device 1110. Power mode switch 1170 can be configured to change states (e.g., between open or closed) as function of the relative distance between an end portion 1132 and an end portion 1133. For example, when a user displaces one of end portion 1132 and end portion 1133 from the other, power mode switch 1170 can change state (e.g., switch from an open state to a closed state) to switch strapband 1101 from a first mode in which there is negligible or no power consumption to a second mode in which there is power consumption by one or more components. In one embodiment, power mode switch 1170 can be implemented as a magnetic switch or relay that has one state in the presence of a magnetic field and another state in the absence of such a magnetic field. A magnetic switch can detect the displacement between points 1140 and 1141 in which a displacement greater than distance, "d," causes a change in state. In some embodiments, power mode switch 1170 can be implemented as a software switch or a mechanical switch under control of software (e.g., executable instructions processed by power manager 1104). Thus, power manager 1104 can determine whether end portion 1132 is displace from end portion 1133 and control the operation of power mode switch 1170. For example, connector 1130 can be inserted into and removed from a connector port (not shown) at end 1131. Power manager 1104 can operate to detect that connector 1130 is not coupled to the connector port (e.g., by detecting no current flow or high resistance) and place power mode switch 1170 in first state (e.g., an open state), and can operate further to detect that connector 1130 is coupled to the connector port (e.g., by detecting current flow or low resistance) and place power mode switch 1170 in second state (e.g., an second state). Note that power modes (e.g., test mode or intermediate mode) that provides for less functionality in a "shipping mode" with reduce power consumption than in an "operational mode."

Figure 12A:
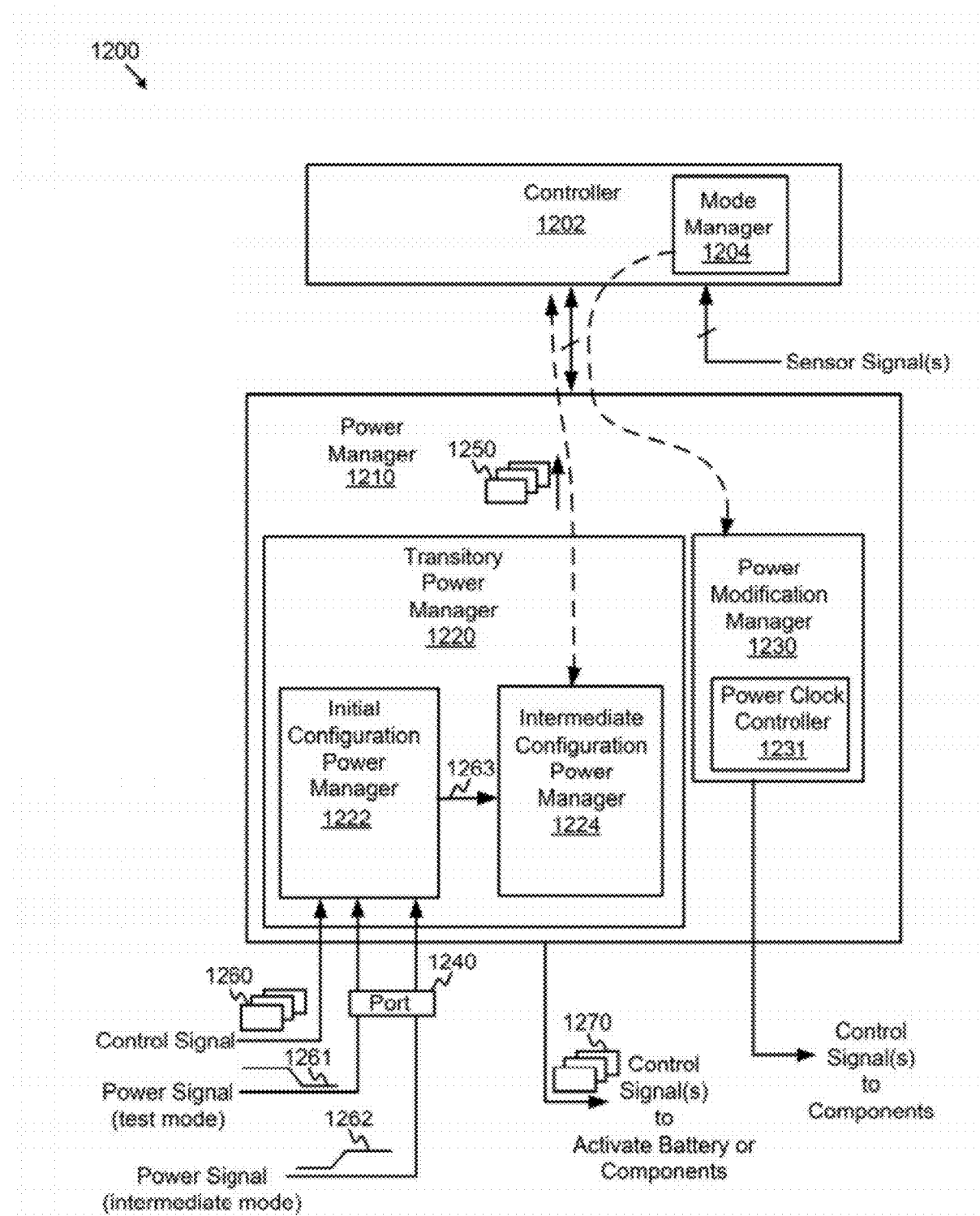
FIG. 12A is a detailed diagram of an example of a power manager including a transitory power manager, according to various embodiments.

FIG. 12A is a detailed diagram of an example of a power manager including a transitory power manager, according to various embodiments. Diagram 1200 depicts a controller 1202 coupled to a power manager 1210, which, in turn, includes a transitory power manager 1220 and a power modification manager 1230. Transitory power manager 1220 is configured to operate a strapband in one or more power modes in which little (i.e., negligible) or no current is drawn during one or more of these type of power modes. Transitory power manager 1220 includes an initial configuration power manager 1222 to control power for a first power mode and an intermediate configuration power manager 1224 to control power for a second power mode. Power manager 1210 is configured to generate signals 1270 (e.g., control and/or power signals) to modify the application of power to one or more component, including a power mode switch, such as power mode switch 1170 of FIGS. 11 and 12B, and one or more applications or sets of executable instructions. For example, in a first power mode, initial configuration power manager 1222 configures the strapband and its components (not shown) to draw essentially no power (e.g., the components are in hibernation or are operationally inactive). The first power mode can be used, for example, during relatively long periods of inactivity, such as when being shipped from a manufacturer (e.g., a first geographic location) to a retailer or a waypoint (e.g., a second geographic location) prior to arriving at the retailer. When a strapband is loaded into a cargo ship, it will remain in the first power mode until such time when that mode is terminated (e.g., after removal from a shipping container and power is applied thereto). Typically during transit, the orientation of a band is shared with other hands (i.e., they share one orientation when arranged in a shipping crate). In some examples, the band in the first power mode is in a configuration in which no power is applied to the subset of sensors, and, as such the sensors are inoperable. In some cases, negligible or no power is applied to the processor (e.g., a controller) or peripheral components. Therefore, power manager 1210 is configured to electrically isolate sensors from a battery during transit from a first geographic location to a second geographic location to preserve power.

In a second power mode, initial configuration power manager 1222 configures the strapband and its components (not shown) to draw a limited amount of power (e.g., certain components are selected to become operationally active). The second power mode can be used, for example, during relatively shorter periods of inactivity prior to pairing with a user or purchaser, such as in transit from a warehouse to a retailer or from a retailer to a waypoint to a user. When a strapband is on display at the retailer, it will remain in the second power mode until such time when that mode is terminated (e.g., after purchase, such as when power is again applied thereto). The second power mode is a low power mode and will activate, for example, when a sensor (e.g., an accelerometer) indicates movement of the device (e.g., when a prospective buyer picks up the packaged strapband to inspect it prior to purchase, or when a button or input device to the device is actuated). During this mode, the orientation of a band is independent of the other hands as they have been unpacked from a shipping crate and each can be individually inspected (and oriented) by a consumer. In some cases, the second power mode is a mode in which power is applied to a subset of sensors, with the second power mode being subsequent to the first power mode. The transitory power manager 1220 can be configured to detect an application of power to the connector, and, responsive to the application of power, the transitory power manager switches the band from the first power mode to the second power mode. Therefore, these power modes permit charge to remain on the battery so that a user will purchase a charged device, thereby having experienced the strapband unencumbered by a requirement to charge the device when is the package is first opened. In some embodiments, the second power mode can be described as an intermediate mode in which a strapband is configured to consume an intermediate amount of power relative to a first power mode (e.g., negligible or no power consumption) or an operational mode (e.g., components of a strapband can receive power in response to requests or implementations by a user).

Initial configuration power manager 1222 includes port(s) 1240 configured to accept control signals (and/or power signals) to either place the strapband into the first power mode or to deactivate the first power mode. At an initial point in time, a battery is charged for the strapband and then an initiation control signal is applied to initial configuration power manager 1222, which, in turn, activates the first power mode. The initiation control signal can include control data 1260 (e.g., a command). Or, the initiation control signal to initiate the first power mode can be signal 1261, which is the removal of a power signal during a certain mode of operating the strapband (e.g., during test mode at the manufacturer). Initial configuration power manager 1222 detects the removal of power, and then configures the strapband to enter the first power mode. Upon receiving an exit control signal to exit the first power mode, the strapband can optionally enter a second power mode, whereby one or more components of the strapband (e.g., controller 1202) are operationally activated as power is selectively applied. An example of an exit control signal for exiting the first power mode is signal 1262, which is the application of power to the strapband (and power manager 1210). Optionally, initial configuration power manager 1222 can transmit a signal via path 1263 to intermediate configuration power manager 1224, whereby the signal indicates the termination of the first power mode. Upon receiving this signal, intermediate configuration power manager 1224 the strapband enters the second power mode. In some cases, intermediate configuration power manager 1224 transmits data 1250 to controller 1202 indicating that the second power mode is activated. In this mode, controller 1202 can control a subset of components. For example, controller 1202 can apply power to activate an accelerometer for detecting motion. In some embodiments, the second power mode can remain active until a certain event (e.g., a date, a threshold activity level is reached, thereby indicating the device was purchased, etc.). A register, for example, in transitory power manger 1220 can maintain a data value representing whether the strapband is in either the first power mode or the second power mode, according to some embodiments.

Controller 1202 can include a mode manager 1204 to manage and activate other modes of operation, for example, when the first and second power modes are not selected or have expired. For example, mode manager 1204 can determine whether to place the strapband into a "normal mode" of operation, an "active mode" of operation, a "sleep mode" of operation, or the like. In one or more of these modes, power management may be implemented by, for example, a power modification manager 1230. Power modification manager 1230 is configured to modify the application of power to one or more components based on the mode of operation determined by mode manager 1204. According to some embodiments, power modification manager 1230 can include a power clock controller 1231 configured to modify power consumption by generating a variable clock to drive, for example, a processor implemented as controller 1202. Note that controller 1202 and power manager 1210 can have their structures and functionalities combined, or can have them distributed into additional, separate entities (e.g., separate hardware components or software modules). In at least one example, either initial configuration power manager 1222 or transitory power manager 1220, or both, can be implemented in hardware (e.g., as part of a batter pack), and intermediate configuration power manager 1224 can be implemented as a processor-based low power mode.

Figure 12B:
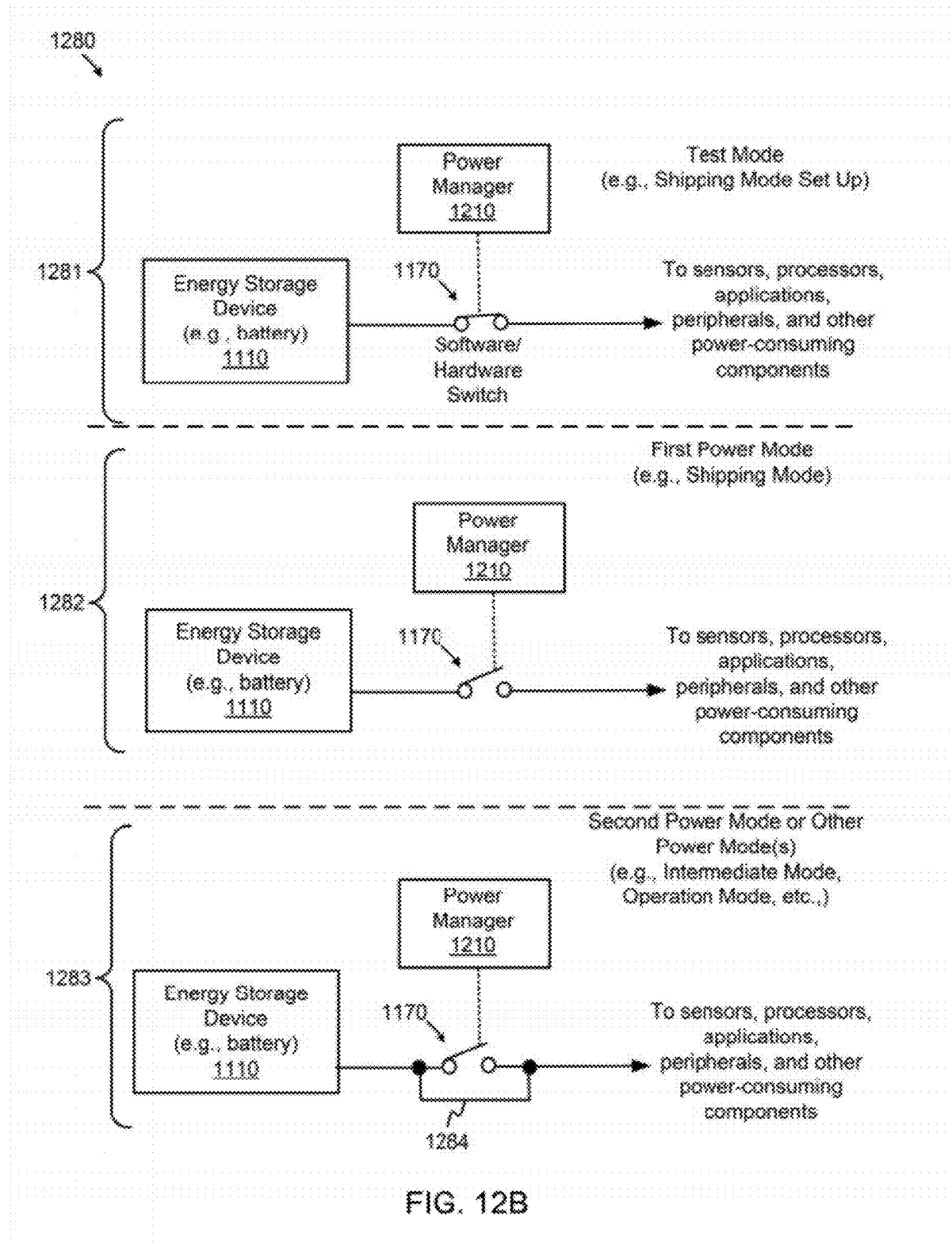
FIG. 12B is a diagram representing examples of the operation of a power mode switch in association with a strapband, according to some embodiments.

FIG. 12B is a diagram 1280 representing examples of the operation of a power mode switch in association with a strapband, according to some embodiments. During a setup operation 1281 of a power mode switch, such as power mode switch 1170 of FIG. 11, in which power mode switch 1170 is set into a first state. An example of such a setup operation can occur during test mode or any operation prior to shipping (or any other duration of time deemed to be long enough to configure the strapband into a first power mode state). Power in setup operation 1281 can be applied from energy storage device 1110 to any sensor, processor, application, peripheral, or other power-consuming component for purposes of testing. In one embodiment, power manager 1210 can operate to set power mode switch 1170 in a closed state. In other embodiments, a magnetic switch can be implemented as power mode switch 1170 in a closed state. After setup operation 1281, power mode switch 1170 is set in a first state 1282 in which negligible or no power is applied from energy storage device 1110 to sensors, processors, applications, peripherals, or any other power-consuming component (e.g., in an intermediate mode or a shipping mode). In one embodiment, power manager 1210 can operate to set power mode switch 1170 in an open state. In other embodiments, a magnetic switch can be implemented as power mode switch 1170 in an open state, for example, in the presence of a magnetic field. Power mode switch 1170 is switched into a second state 1283 in which power is applied from energy storage device 1110 to one or more sensors, processors, applications, peripherals, or any other power-consuming component (e.g., in an intermediate mode or an operational mode). In one embodiment, power manager 1210 can operate to set power mode switch 1170 in a closed state. In other embodiments, a magnetic switch can be implemented as power mode switch 1170 in a closed state, for example, in the absence of a magnetic field, such as when end portions of a strapband are displaced from each other. According to some embodiments, power mode switch 1170 in second state 1283 can be configured to be formed irreversibly into a closed circuit path 1284 to prevent reverting from operational mode to a shipping mode (e.g., either test mode or an intermediate mode).

Figure 12C:
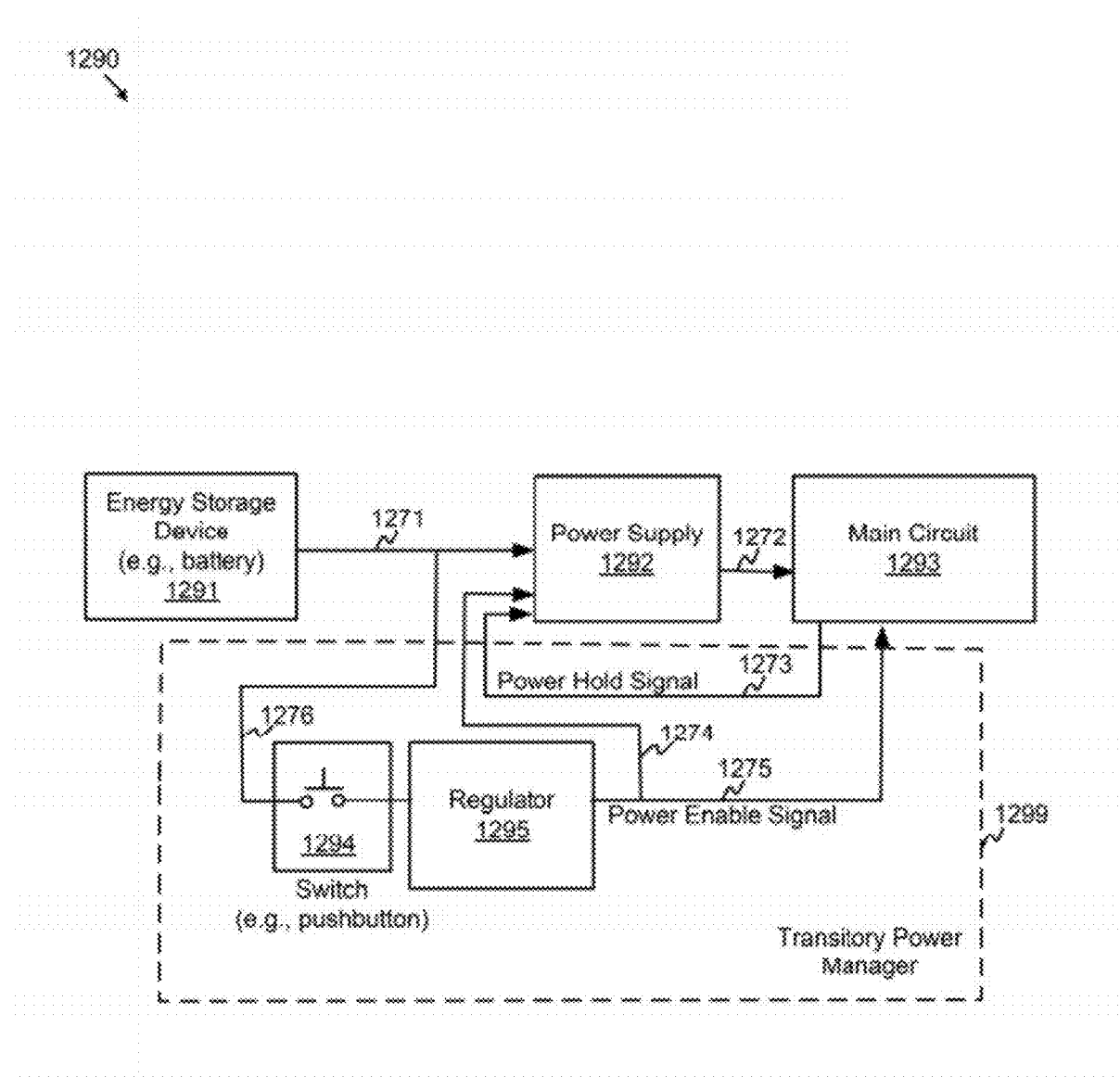
FIG. 12C is a diagram representing an example of a circuit for transitioning between power modes, according to some embodiments.

FIG. 12C is a diagram representing an example of a circuit for transitioning between power modes, according to some embodiments. Diagram 1290 depicts an energy storage device 1291, such as a battery, configured to deliver power (e.g., voltage and current) over path 1271 via a power supply 1292 to a main circuit 1293. Power supply 1292 is configured to deliver one or more voltages via path(s) 1272 to circuitry in main circuit 1293 of a strapband. In some embodiments, a transitory power manager 1299 is configured to include a switch 1294 coupled to a regulator 1295, which is optional, and operates to control transitions between power modes, according to some embodiments. Transitory power manager 1299 is configured to operate a strapband in one or more power modes in which little (i.e., negligible) or no current is drawn during one or more of these type of power modes. To illustrate operation of transitory power manager 1299, consider that a strapband including the components in diagram 1290 is in a first power mode such that little or no power is drawn by main circuit 1293. In the first power mode, power supply 1292 is disabled, thereby providing little to no power to main circuit 1293. To initiate a transition from the first power mode to a second power mode, switch 1294 can generate a signal to initiate the transition. For example, a user can depress button 1294 to supply a battery power signal via path 1276 to regulator 1295. In turn, regulator 1295 receives the battery power signal to generate power enable signals 1274 and 1275. In response to receiving power enable signal 1274, power supply 1292 generates and transmits one or more power (or voltage) signals via path 1272(*s*) to power main circuit. In response to receiving power enable signal 1275 and power via path(s) 1272, logic in main circuit 1293 generates (e.g., under software control) a power hold signal configured to maintain the strapband in a different power mode than the first power mode subsequent to activation of switch 1294. The different power mode can be a second power mode, such as an intermediate or operational power mode. Logic in main circuit 1293 transmits the power hold signal via path 1273 to power supply 1292. According to some embodiments, the generations of the power hold signal irreversibly facilitates the exit from the first power mode.

Figure 13:
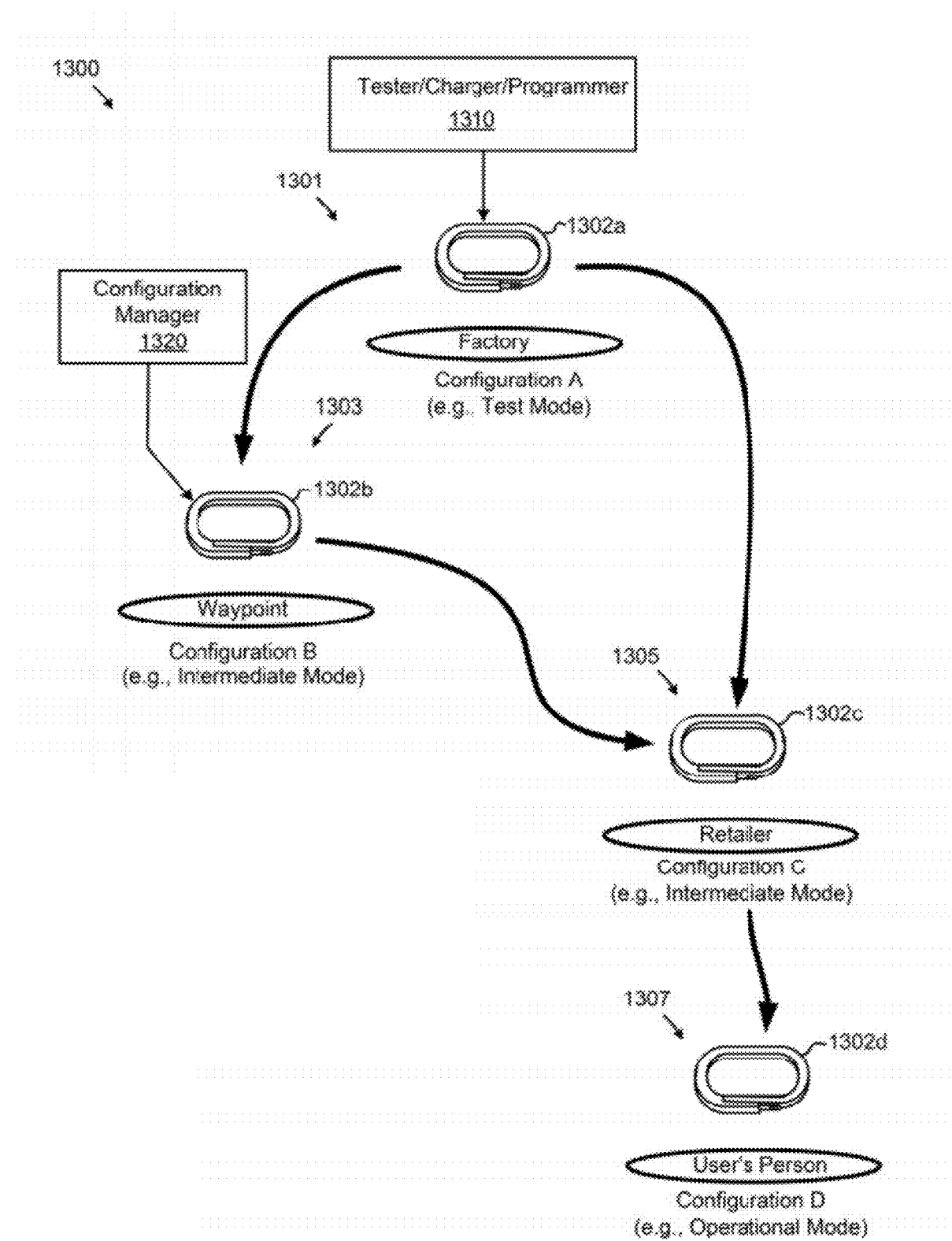
FIG. 13 is a diagram representing examples of power modes for a strapband, according to some embodiments.

FIG. 13 is a diagram representing examples of power modes for a strapband, according to some embodiments. Diagram 1300 depicts an example of four instances or configurations of a strapband and the implementation of power modes thereof. At 1301, a strapband 1302*a* is coupled to a tester, a charger, and/or a programmer ("tester/charger/programmer") 1310, or one or more devices that can test, charge and program strapband 1302*a*. This may occur at the factory. Tester/charger/programmer 1310 performs a functional test and then charges the strapband 1302*a*. At 1301, tester/charger/programmer 1310 can also program (e.g., "reflash") a memory or firmware in strapband 1302*a*. Then, the strapband can be shipped, under a first power mode, to a waypoint, and, at 1303, can be subject to the operation of a configuration manager 1320. Configuration manager 1320 can program or "reflash" the memory of strapband 1302*b* to include modifications since manufacture. Once power is applied to strapband 1302*b*, the strapband detects the application of power, and, in response, exits the first power mode and enters the second power mode. The strapband is shipped to a retailer at 1305. In the second power mode, strapband 1302*c* is in a low power mode and is able to detect motion so that, for example, a prospective buyer can interact with strapband 1302*c*. Or, in some embodiments, the strapband can detect a button event (or any other input) when in the low power mode so that the prospective buyer can interact with strapband 1302*c*. During transit from the retailer to the users' person at 1307, the strapband remains in the second power mode until an event occurs, the event being indicative of ownership of strapband 1302*d*. Thus, the transitory power modes may no longer be needed during, for example, normal modes of operation. In some cases, strapband 1302*a* can be shipped from the manufacturer to the retailer. In this case, tester/charger/programmer 1310 programs a countdown value associated with an expected date of arrival at the retailer. The strapband uses power only for a timer to effect the countdown. At expiration of the countdown, the strapband can enter the second power mode. Note that power modes for strapbands 1302*a*, 1302*b*, and 1302*c* can be described as being in a "shipping mode," which provides for less functionality than in an "operational mode" for a user.

Figure 14:
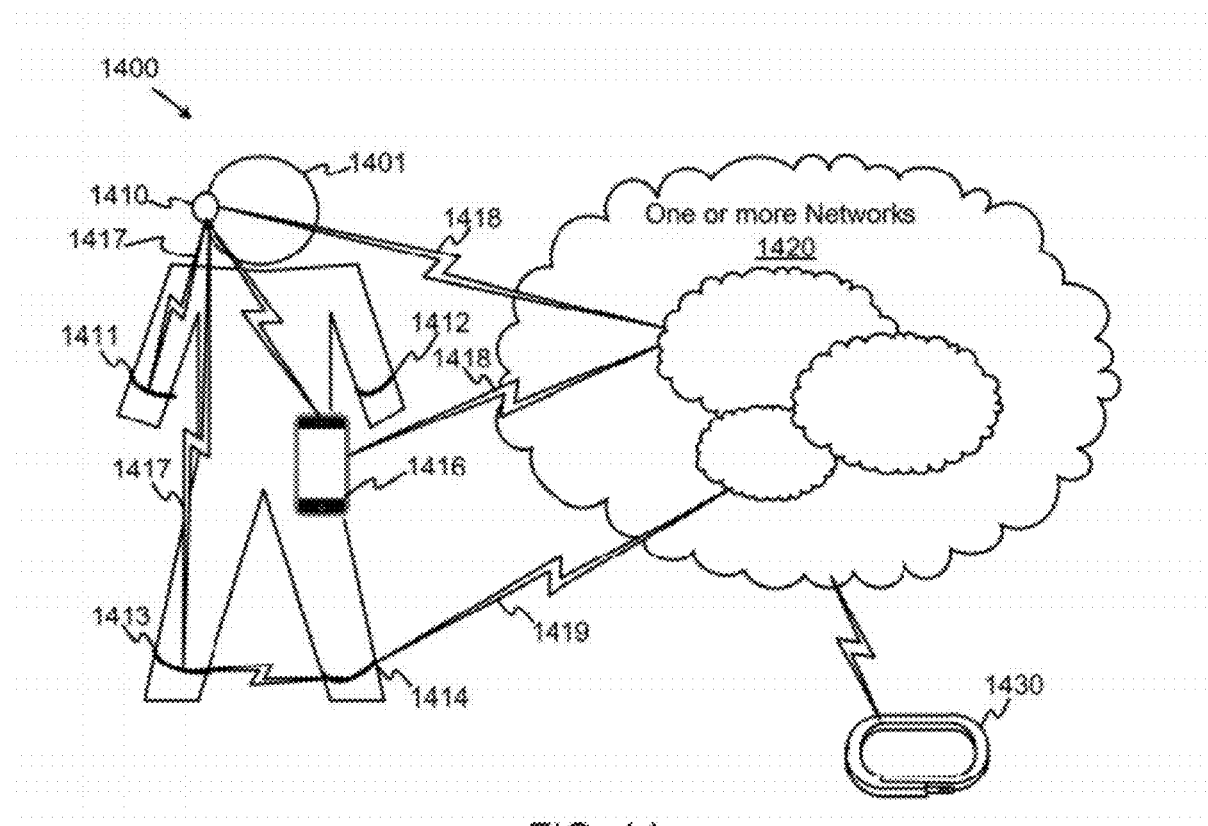
FIGS. 14 and 15 are diagrams representing examples of networks formed using one, or more strapbands, according to some embodiments.
Figure 15:
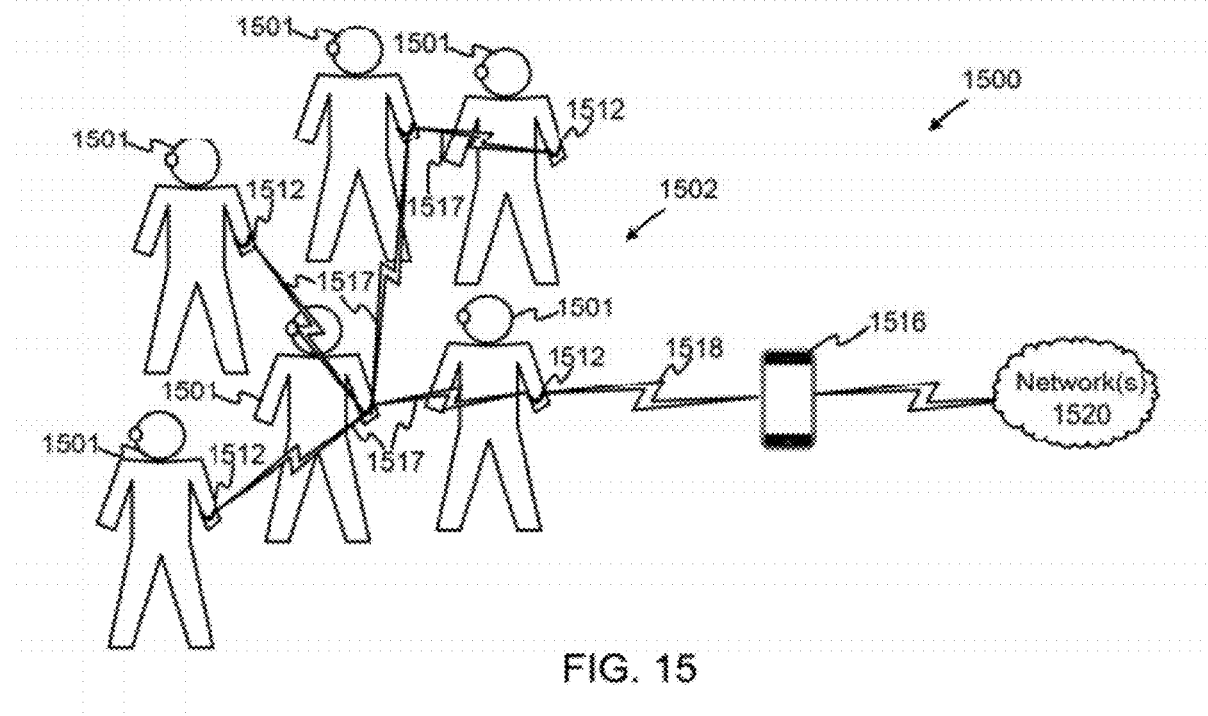

FIGS. 14 and 15 are diagrams representing examples of networks formed using one or more strapbands, according to some embodiments. Diagram 1400 of FIG. 14 depicts a personal, wearable network including a number of strapbands 1411, 1412, 1413, and 1414 (more or less) disposed on locomotive bodily members of a user or an entity (e.g., a human, an animal, such as a pet, etc.), according to one example. In some embodiments, strapbands 1411, 1412, 1413, and 1414 can communicate with each other via, for example, Bluetooth® to form a peer-to-peer network. Further, a wearable communication device 1410 configured for aural communication, such as a headset, can communicate with strapbands 1411, 1412, 1413, and 1414, and can serve as a router to route data among strapbands 1411, 1412, 1413, and 1414, and with a mobile communications device 1416 (e.g., a mobile phone). As shown, wearable communication device 1410 forms communication links 1417 with one or more strapbands 1411, 1412, 1413, and 1414. Any of strapbands 1411, 1412, 1413, and 1414 can communicate on communication link 1419 via networks 1420 to a remote strapband 1430. Or, strapbands 1411, 1412, 1413, and 1414 can communicate via communication links 1418 and networks 1420 to a remote strapband 1430. Note that in some embodiments, strapbands 1411, 1412, 1413, and 1414 form a secured personal, wearable network based on security keys that consider, for example, motion (e.g., all strapbands 1411, 1412, 1413, and 1414 are moving in the same direction and can be indicative of a single person using strapbands 1411, 1412, 1413, and 1414).

Diagram 1500 of FIG. 15 depicts a number of strapbands that form a local network between the strapbands, according to one example. A strapband 1512 is associated with a user 1501. Strapbands 1512 can communicate via communication links 1517 and 1518 to communication device 1516, and, in turn, to one or more network 1520. Note that group 1502 of users 1501 may be engaging in a common event, such as a yoga class or a marathon. Given this common activity, and some other optional activity or information, a secured (or unsecured) local network can be established, for example, without explicit request by users 1501. Rather, the common activity and general permissions can facilitate establishment of an ad hoc network among strapband 1512, which, for example, can cease to operate as network once users cease to participate in the common activity.

Figure 16:
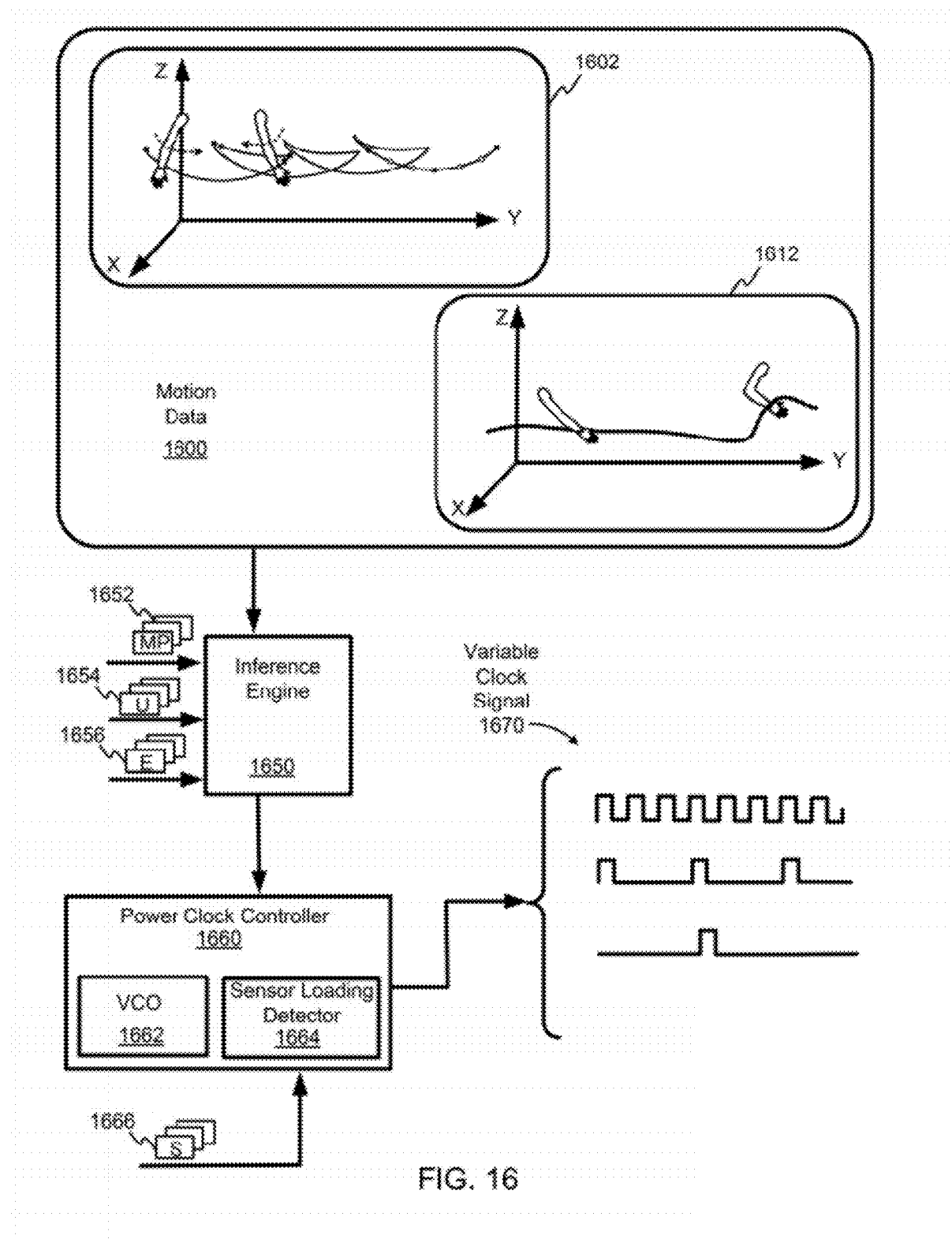
FIG. 16 depicts a power clock controller configured to modify clock signals, according to some embodiments.

FIG. 16 depicts a power clock controller configured to modify clock signals, according to some embodiments. A power clock controller 1660 is configured to adapt a clock frequency and/or waveform shape to operate a processor at a sufficient rate to process data generated by sensors and perform other functions for the activity a user is engaged or mode of operation. In some cases, power clock controller 1660 generates a clock signal that is at a lower frequency than the maximum frequency. Power clock controller 1660 ramps a clock up or down in frequency to operate a processor and other circuitry with negligible or no errors. Power clock controller 1660 can modify one or more clock signals to place a processor in an optimally lock, power consumption state while operating sufficiently to, for example, process inputs from a variety of sensors and other peripheral components. As shown, power clock controller 1660 can include a voltage-controlled oscillator ("VCO") to vary the frequency of the clock signal to generate, for example, a variable clock signal, as represented by the different waveforms of variable clock signal 1670.

Further to FIG. 16, power clock controller 1660 can be coupled to an inference engine 1650. Inference engine 1650 is configured to receive motion data 1600 to determine whether motion associated with the band worn by a user is related to one activity, such as depicted by walking motion data 1602, or to another activity, such as depicted by sleeping motion data 1612. Inference engine 1650 operates to infer the activity in which a band is engaged by also receiving motion pattern data ("MP") 1652 that describes motion patterns or template against which motion data 1600 is compared to determine an activity (e.g., the motion data 1600 is matched to a "best fitting" motion pattern). Inference engine 1650 also receives data about the user ("U") 1654, such as heart rate, skin temperature, or other user-specific information about the user, and data about the environment ("E") 1656, such as ambient air temperature, atmospheric pressure, amount of light, etc. Based on the foregoing, inference engine 1650 can determine the likelihood that a user is engaged in a specific activity. One example of an inference engine is disclosed in U.S. Provisional Pat. App. No. 61/495,997, filed Jun. 11, 2011 and entitled "Data Capable Strapband."

Power clock controller 1660 can also include a sensor loading detector 1664 that is configured to detect the sensor loading, or the amount of data generated by a collection of sensors during an activity or mode at a certain rate. By analyzing the sensor load data, motion data, and data describing the activity, clock power generator 1660 can be configured to generate a variable clock signal adapted to operate a processor or a controller at rate at which a subset of sensors generate data. As such, the processor can then operate a rate that is sufficient to match the sensor data throughput, thereby sampling the sensor data at a sufficient rate to conserve power and capture the data.

FIG. 17A depicts a power modification manager configured to modify the application of power to one or more components, according to some embodiments. In the example shown, power modification manager 1710 can be configure receive either one or more clock signals (e.g., from clock generator 1760) or power from one or more power sources (e.g., from energy storage device 1762), or both. Power modification manager 1710 can include a number of multiplexers 1711, 1712, and 1714 that are configured to multiplex certain clock signals, if applicable, and power signals to sensors 1720 and peripheral components 1722. According to some embodiments, power modification manager 1710 can make its determinations based on data representing a priority scheme 1724, as well as an activity derived from inference engine 1750. As was the case in FIG. 16, inference engine 1750 can receive motion data ("M") 1751, data about the user ("U") 1754, data about the environment ("E") 1756, and motion pattern data 1752.

Figure 17B:
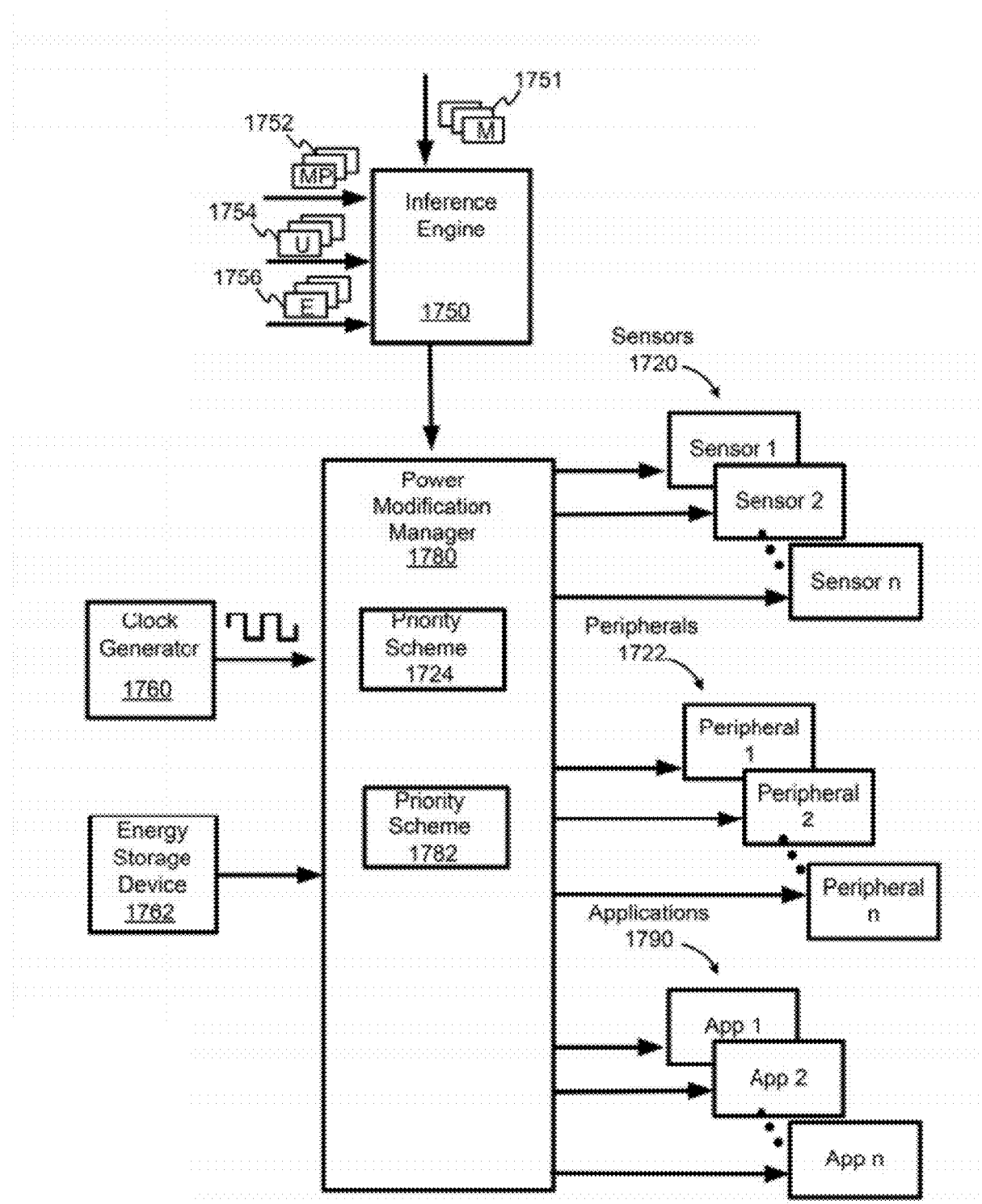
FIG. 17B depicts a power modification manager configured to modify the application of power to one or more components that include one or more applications (or "apps"), according to some embodiments.

FIG. 17B depicts a power modification manager configured to modify the application of power to one or more components that include one or more applications (or "apps"), according to some embodiments. In the example shown, power modification manager 1780 can be configured to receive or otherwise control either a variable clock signal or power from one or more power sources, or both. As discussed in FIG. 17A, power modification manager 1780 can multiplex certain clock signals, if applicable, and power signals to sensors 1720 and peripheral components 1722. Further, power modification manager 1780 can multiplex certain clock signals and power signals to or responsive to executable instructions, such as applications 1790. Therefore, power modification manager 1780 can manage power applied to applications 1790, for example, responsive to a priority scheme 1782. For example, the priority of an application 1790 can be based on the rate at which an application is updated or modified, the duration or amount of time that the application is used, the number of sensors used by the application, the amount of CPU processor cycles required by the application, and other characteristics of the application. Further, power modification manager 1780 can manage or vary a certain clock rate to operation a processor (or CPU) at a rate to preserve battery life. Power modification manager 1780 can then adjust the clock rate as generated by a power clock controller of FIG. 16 to accommodate any number of applications 790 during which their instructions are being executed. As such, power modification manager 1780 can permit power to be applied to those components under control of high-power applications, and can reduce power consumption in a strapband when low-power applications are being executed. Therefore, a processor or CPU can be clocked at a rate that performs a number of applications while preserving power consumption that otherwise might occur with higher clock rates, at least in some cases. In some embodiments, an application 790 can be referred to or implemented as an "applet" or any relatively small amount of executable instructions that can be executed in cooperation with other instructions. As was the case in FIG. 17A, inference engine 1750 can receive motion data ("M") 1751, data about the user ("U") 1754, data about the environment ("E") 1756, and motion pattern data 1752, and an application 1790 can be selected or deselected as a function of data received from inference engine 1750.

Figure 18:
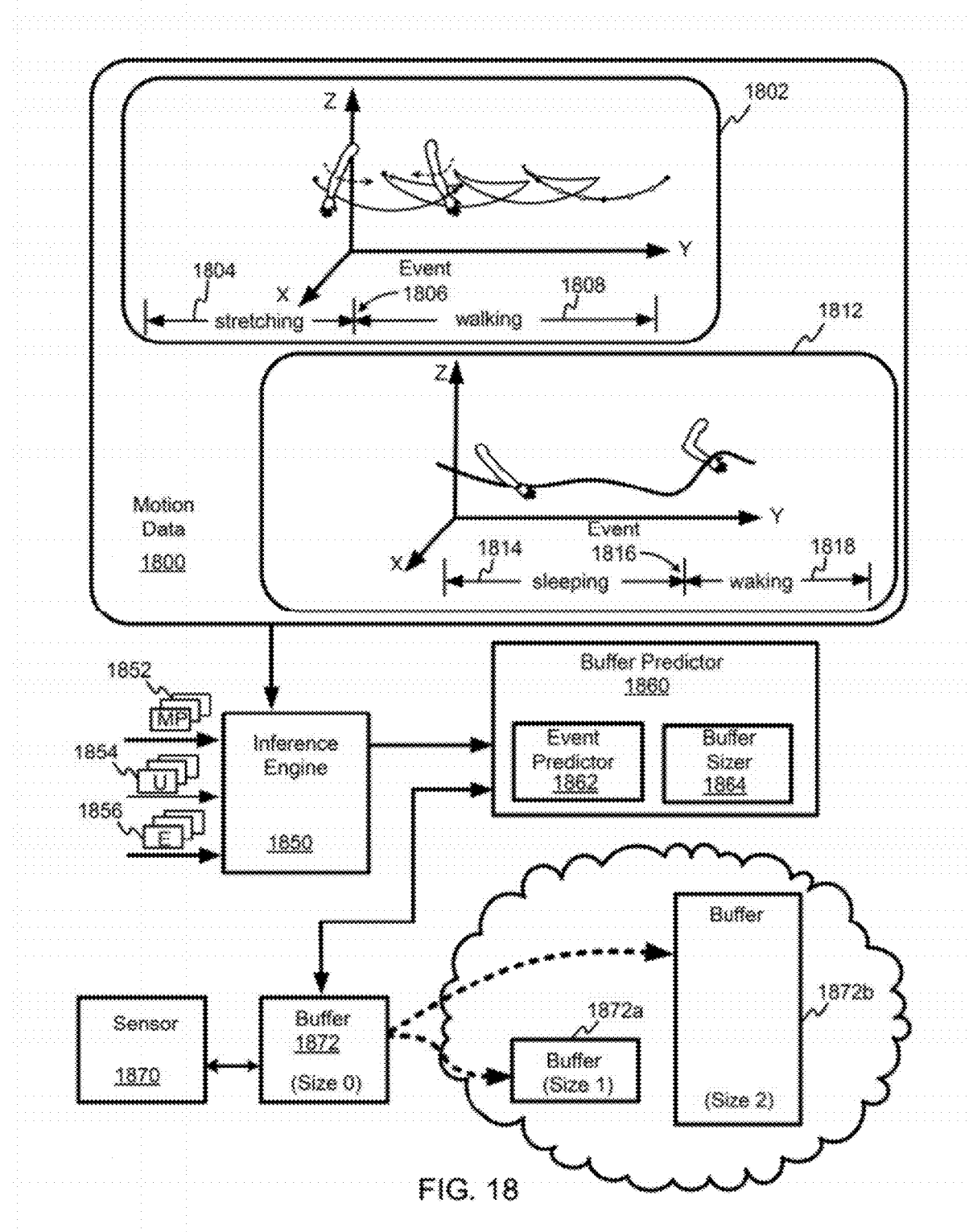
FIG. 18 depicts a buffer predictor configured to modify a size of one or more buffers associated with one or more components, according to some embodiments.

FIG. 18 depicts a buffer predictor configured to modify a size of one or more buffers associated with one or more components, according to some embodiments. Buffer predictor 1860 includes an event predictor 1862 and a buffer sizer 1864, and is configured to dynamically size a buffer for receiving or transmitting sensor data as a function of whether a certain event is occurring or is likely to occur. The buffers are used typically to store data from sensors. In the context of buffer prediction, the term "event" can refer to a change in between different activities or modes that might require different processing capabilities. Event predictor 1862 is configured to predict an event in which data processing requirements either go up or go down, such as when a user transitions from an activity with a relatively low amount of motion to an activity with a relatively high amount of motion, or vice versa. While event predictor 1862 may use inference engine 1850 to predict events, event predictor 1862 need not be limited to the use of inference engine 1850. In this example, inference engine 1850 can receive motion data ("M") 1800, data about the user ("U") 1854, data about the environment ("E") 1856, and motion pattern data ("MP") 1852. In some cases, an event can be predicted by monitoring motion associated with an activity in which a user wearing the band is engaged, comparing the motion associated with the activity to motion pattern data to identify precursor motion associated with a subsequent motion, and establishing the size of the buffer for the amount of sensor data generated by the subsequent motion.

Buffer sizer 1864 is configured to modify a size of buffer 1872, which is associated with sensor 1870, to allocate memory for buffer 1872 as butler 1872a or buffer 1872b. By dynamically sizing a buffer 1872, a processor need not operate at a higher power level without introducing latency, as might be the case when the sizes of buffers have static sizes. Static buffer sizes can include unused allocated memory locations that otherwise might be processed.

To illustrate operation of the event predictor 1862, consider that motion pattern data 1852 includes motion profiles or template against which data 1802 representing a first set of motion, and data 1812 representing a second set of motion can be compared. Data 1802 depicts a user stretching during a period of time 1804 (e.g., in the Y-axis) and transitioning at event 1806 to begin walking at 1808. Similarly, data 1812 depicts a user sleeping during a period of time 1814 (e.g., in the Y-axis) and transitioning at event 1816 to begin waking at 1818. It is at these events, that the data processing requirements might increase, for example, as the sampling rate increases to capture motion data over short periods of time. In some embodiments, stretching during a period of time 1804 and sleeping at 1814 can be modeled as precursor activities, which are detectable activities that signal an impending event 1806 or 1816. By predicting subsequent activities, such as walking at 1808 and waking at 1818, buffer sizer 1864 can operate to effectively size buffers rather than using a buffer size that may be a maximum size. Note that events 1806 and 1816 are merely examples and the term "event" need not be limited to changes in motion and an event can be described broadly in relation to the operation of a strapband.

In at least some examples, the structures and/or functions of any of the above-described features can be implemented in software, hardware, firmware, circuitry, or a combination thereof. Note that the structures and constituent elements above, as well as their functionality, may be aggregated with one or more other structures or elements. Alternatively, the elements and their functionality may be subdivided into constituent sub-elements, if any. As software, the above-described techniques may be implemented using various types of programming or formatting languages, frameworks, syntax, applications, protocols, objects, or techniques. As hardware and/or firmware, the above-described techniques may be implemented using various types of programming or integrated circuit design languages, including hardware description languages, such as any register transfer language ("RTL") configured to design field-programmable gate arrays ("FPGAs"), application-specific integrated circuits ("ASICs"), or any other type of integrated circuit. These can be varied and are not limited to the examples or descriptions provided.

Although the foregoing examples have been described in some detail for purposes of clarity of understanding, the above-described inventive techniques are not limited to the details provided. There are many alternative ways of implementing the above-described invention techniques. The disclosed examples are illustrative and not restrictive.

The invention claimed is:

1. A band comprising:
    a subset of sensors;
    a controller coupled to the subset of sensors;
    an energy storage device;
    a connector configured to receive power and control signals, the connector coupled to the energy storage device;
    a power manager comprising:
        a transitory power manager configured to manage power consumption of the band during a first power mode in which no power is applied to the subset of sensors; and
        a power clock controller configured to modify a clock rate of a clock signal for application to the controller as a function of a mode of operation of the band
        wherein the transitory power manager is configured further to manage the power consumption of the band during a second power mode in which power is applied to the subset of sensors, the second power mode being subsequent to the first power mode,
        wherein the transitory power manager is configured to detect an application of power to the connector, and, responsive to the application of power, the transitory power manager switches the band from the first power mode to the second power mode;
        wherein the first power mode and the second power mode coincide with a first interval of time and a second interval of time, respectively; and
        wherein the first interval of time comprises an amount of time during which the orientation of the band is shared with other bands in one orientation and the second interval of time comprises another amount of time during which the orientation of the band is independent of the other bands.

2. A band comprising:
    a subset of sensors;
    a controller coupled to the subset of sensors;
    an energy storage device;
    a connector configured to receive power and control signals, the connector coupled to the energy storage device;
    a power manager comprising:
        a transitory power manager configured to manage power consumption of the band during a first power mode in which no power is applied to the subset of sensors; and
        a power clock controller configured to modify a clock rate of a clock signal for application to the controller as a function of a mode of operation of the band
        wherein the transitory power manager is configured further to manage the power consumption of the band during a second power mode in which power is applied to the subset of sensors, the second power mode being subsequent to the first power mode,
        wherein the transitory power manager is configured to detect an application of power to the connector, and, responsive to the application of power, the transitory power manager switches the band from the first power mode to the second power mode;
        wherein the first power mode and the second power mode coincide with a first interval of time and a second interval of time, respectively; and wherein the first interval of time comprises an amount of time during which the band is shipped from a first geographic location to a second geographic location with the subset of sensors in an inoperable state and the second interval of time comprises another amount of time during which the subset of sensors in an operable state.

3. A method comprising:
receiving a first signal to enter a first power mode for a band including a subset of sensors including one or more accelerometers, the first power mode electrically isolating the subset of sensors from a battery during transit from a first geographic location to a second geographic location;
receiving a second signal into the band to exit the first power mode;
coupling internal to the band the battery to the subset of sensors responsive to receiving the second signal; and
entering a second power mode responsive to coupling the battery to the subset of sensors.

4. The method of claim 3, wherein entering the second power mode comprises:
maintaining electrical isolation between the battery and a sensor not within the subset of sensors; and
detecting whether to enter an operation power mode; and
coupling internal to the band the battery to the sensor upon detecting to enter the operation power mode.

5. The method of claim 3, wherein entering the second power mode comprises:
coupling internal to the band the battery to other sensors.

6. The method of claim 3, wherein receiving the second signal further comprises:
receiving a power signal via a connector; and
detecting the power signal at a power manager.

7. The method of claim 3 further comprising:
determining an activity in which a user wearing the band is engaged;
receiving data from the subset of sensors associated with the activity; and
adjusting a frequency of a clock signal to achieve a threshold amount of throughput for the data received from the subset of sensors.

8. The method of claim 7, wherein adjusting the frequency of the clock signal comprises:
modifying operation of a voltage controlled oscillator ("VCO") to generate the frequency.

9. The method of claim 8, wherein modifying the operation of the voltage controlled oscillator comprises:
determining a priority of one or more of the subset of sensors relative to other priorities of other sensors.

10. The method of claim 8, wherein modifying the operation of the voltage controlled oscillator comprises:
determining a priority of an application that is executing relative to other priorities of other applications.

11. The method of claim 3, further comprising:
detecting an event after which a sensor in the subset of sensors produces an amount of sensor data in a unit of time; and
adjusting a size of a buffer to match the amount of the sensor data.

12. The method of claim 11, wherein detecting the event comprises:
monitoring motion associated with an activity in which a user wearing the band is engaged;
comparing the motion associated with the activity to motion pattern data to identify precursor motion associated with a subsequent motion; and
establishing the size of the buffer for the amount of sensor data generated by the subsequent motion.

13. The method of claim 3, further comprising initially entering the first power mode.

14. The method of claim 3, further comprising generating the second signal in response to detecting a physical displacement between a first end portion of the band and a second end portion of the band.

15. The method of claim 3, further comprising generating the second signal in response to a user depressing a button on the band.

16. The method of claim 3, further comprising generating the second signal in response to a change in location-related data received from the subset of sensors.

17. The method of claim 3, further comprising generating the second signal in response to a change in movement-related data received from the subset of sensors.

18. The method of claim 3, further comprising generating the second signal in response to a change in medical-related data received from the subset of sensors.

19. The method of claim 6, further comprising recharging the energy storage device with the power signal.

20. The method of claim 7, wherein adjusting the frequency of the clock signal comprises multiplexing one of a plurality of oscillating signals of varying frequency onto the clock signal.

* * * * *